(12) United States Patent
Takahashi et al.

(10) Patent No.: US 8,568,725 B2
(45) Date of Patent: Oct. 29, 2013

(54) METHOD OF TREATING TRANSPLANT REJECTION WITH AN ANTI-CD40 ANTIBODY

(75) Inventors: Nobuaki Takahashi, Gunma (JP); Toru Miura, Gunma (JP); Yoshinori Kitagawa, Gunma (JP); Aki Hirano, Gunma (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 827 days.

(21) Appl. No.: 10/584,345

(22) PCT Filed: Dec. 24, 2004

(86) PCT No.: PCT/JP2004/019750
§ 371 (c)(1),
(2), (4) Date: Feb. 26, 2007

(87) PCT Pub. No.: WO2005/063981
PCT Pub. Date: Jul. 14, 2005

(65) Prior Publication Data
US 2007/0148163 A1    Jun. 28, 2007

(30) Foreign Application Priority Data
Dec. 25, 2003    (JP) ................. 2003-431408

(51) Int. Cl.
*A61K 39/395*    (2006.01)
*C07K 16/28*    (2006.01)

(52) U.S. Cl.
USPC .................. 424/153.1; 424/130.1; 424/133.1; 424/141.1; 424/143.1; 424/144.1; 424/152.1; 424/173.1; 530/387.1; 530/387.3; 530/388.1; 530/388.2; 530/388.22; 530/388.7; 530/388.73

(58) Field of Classification Search
None
See application file for complete search history.

(56) References Cited

U.S. PATENT DOCUMENTS

| | | | |
|---|---|---|---|
| 6,376,653 B1 * | 4/2002 | Holmes et al. | 530/388.22 |
| 6,936,698 B2 * | 8/2005 | Taylor | 530/387.3 |
| 6,998,124 B1 * | 2/2006 | Erickson-Miller et al. | 424/143.1 |
| 7,193,064 B2 | 3/2007 | Mikayama et al. | |
| 7,262,278 B2 | 8/2007 | Tawara et al. | |
| 7,537,763 B2 | 5/2009 | Mikayama et al. | |
| 2003/0059427 A1 | 3/2003 | Force et al. | |
| 2003/0211100 A1 | 11/2003 | Bedian et al. | |
| 2009/0123466 A1 | 5/2009 | Mikayama et al. | |

FOREIGN PATENT DOCUMENTS

| | | |
|---|---|---|
| EP | 0 314 161 A1 | 5/1989 |
| EP | 1 369 431 A1 | 12/2003 |
| EP | 1391464 A1 | 2/2004 |
| JP | 3101690 | 8/2000 |
| JP | 2003-519470 T | 6/2003 |
| WO | WO 88/07089 | 9/1988 |
| WO | WO 95/26403 | 10/1995 |
| WO | WO 99/55369 | 11/1999 |
| WO | WO 00/18437 | 4/2000 |
| WO | WO 00/18804 | 4/2000 |
| WO | WO 00/61637 | 10/2000 |
| WO | WO 00/75348 A1 | 12/2000 |
| WO | WO 02/088186 A1 | 11/2002 |
| WO | WO 03/033538 A1 | 4/2003 |
| WO | WO 2005/063981 A1 | 7/2005 |

OTHER PUBLICATIONS

Sharma et al., Pharmacol Expo Ther 293: 33-41, 2000.*
Chinese Office Action 200480042107.7 issued Jan. 9, 2009.
English Translation of Applicants' Response to Japanese Office Action JP 2005-516724 issued Sep. 9, 2008.
Hepburn, et al., "Antibody-mediated Stripping of CD4 from Lymphocyte Cell Surface in Patients with Rheumatoid Arthritis," *Rheumatology*, 42: 54-61 (Jan. 2003).
Subauste, C., "CD154 and Type-1 Cytokine Response: From Hyper IgM Syndrome to Human Immunodeficiency Virus Infection," *Journal of Infectious Diseases*, 185 (Suppl. 1): S83-89 (2002).
Tong AW et al., "Anti-CD40 antibody binding modulates human multiple myeloma clonogenicity in vitro", Blood, vol. 84, Issue 9, pp. 3026-3033, Nov. 1, 1994.
M. Urashima et al., "CD40 ligand triggered interleukin-6 secretion in multiple myeloma", BLOOD, vol. 85, Issue 7, pp. 1903-1912, Apr. 1, 1995.
Yu-Tzu Tai et al., "CD40 induces human multiple myeloma cell migration via phosphatidylinositol 3-kinase/AKT/$NF_{\kappa}B$ signaling", BLOOD, Apr. 1, 2004, vol. 101, No. 7, pp. 2762-2769.
T. Hayashi et al., "Recombinant humanized anti-CD40 monoclonal antibody triggers autologous antibody-dependent cell mediated cytotoxicity against multiple myeloma cells", Br J. Haematol. May 2003, 121(4), pp. 592-596.
Russian Office Action 2006126979 w/Translation.
Japanese Office Action JP 2005-516724 dated Sep. 9, 2008.
Supplementary Partial European Search Report EP 04 80 8100 dated Jul. 24, 2008.
L.G. Presta et al., "Engineering Therapeutic Antibodies for Improved Function", Biochemical Society Transactions (2002), vol. 30, part 4, 2002, pp. 487-490.
Leonard G. Presta, "Engineering Antibodies for Therapy", Current Pharmaceutical Biotechnology 2002, 3, 237-256.
Ole Henrik Brekke et al., "Human IgG isotype-specific amino acid residues affecting complement-mediated cell lysis and phagocytes", Eur. J. Immunol.1994, 24: 2542-2547.

(Continued)

*Primary Examiner* — Phillip Gambel
(74) *Attorney, Agent, or Firm* — Foley & Lardner LLP

(57) ABSTRACT

A mutant of a potentially therapeutic anti-CD40 antibody is provided which mutant has reduced ADCC and CDC activities designed to be optimized as a pharmaceutical agent. A mutant of an agonistic anti-CD40 antibody, comprising mutation and/or substitution of at least one amino acid in the constant region to reduce the ADCC and/or CDC activities therein, and a mutant of an antagonistic anti-CD40 antibody, comprising at least one mutation or substitution in the constant region to reduce the ADCC and/or CDC activities therein, both mutants having at least a hinge region derived from a human IgG2.

1 Claim, 46 Drawing Sheets
(1 of 46 Drawing Sheet(s) Filed in Color)

(56) References Cited

OTHER PUBLICATIONS

EP Office Action 04 808 100.4-2402 dated Nov. 11, 2008.
Idusogie et al., "Mapping of the C1q Binding Ste on Rituxan, a Chimeric Antibody with a Human IgG1 Fc", 2000, *J. Immunol*, 164(8), pp. 4178-4184.
Tao et al., "Structural Features of Human Immunoglobulin G that Determine Isotype-specific Differences in Complement Activation", 1993, *J. Exp. Med.*, 178(2), pp. 661-667.
Morgan et al., "The N-terminal End of the $C_H2$ domain of Chimeric Human IgG1 anti-HLA-DR is Necessary for C1q, Fc gamma RI and Fc gamma RIII binding", 1995, *Immunology*, 86(2), pp. 319-324.
Reddy, et al., "Elimination of Fc Receptor-Dependent Effector Functions of a Modified IgG4 Monoclonal Antibody to Human CD4", 2000, *J. Immunol.*, 164, pp. 1925-1933.
Angal et al., "A Single Amino Acid Substitution Abolishes the Heterogeneity of Chimeric Mouse/Human (IgG4) Antibody", 1993, *Mol. Immunol*. 30(1), pp. 105-108.
Xu et al., "Residue at Position 331 in the IgG1 and IgG4 $C_H2$ Domains Contributes to their Differential Ability to Bind and Activate Complement", 1994, *J. Biol. Chem.*, 269(5), pp. 3469-3474.
Tao et al., "The Differential Ability of Human IgG1 and IgG4 to Activate Complement is Determined by the COOH-terminal Sequence of the $C_H2$ domain", 1991, *J. Exp. Med.*, 173(4), pp. 1025-1028.
Idusogie et al., "Engineered Antibodies with Increased Activity to Recruit Complement", 2001, *J. Immunol.*, 166(4), pp. 2571-2575.
Aalberse et al., "IgG4 Breaking the Rules", 2002, *Immunology*, 105(1), pp. 9-19.
Newman et al., "Modification of the Fc Region of a Primatized IgG Antibody to Human CD4 Retains Its Ability to Modulate CD4 Receptors but Does Not Deplete CD4+ T Cells in Chimpanzees", 2001, *Clinical Immunology*, 98(2), pp. 164-174.
Summons to attend oral proceedings pursuant to Rulte 115(1) EPC, for European patent application 04808100.4-2406 dated Sep. 23, 2011.
Korean office action application No. 10-2006-7014685 dated Sep. 19, 2011.
Roland Newman et al., "Modification of the Fc Region of a Primatized IgG Antibody to Human CD4 Retains Its Ability to Modulate CD4 Receptors but Does Not Deplete CD4+ T Cells in Chimpanzees", Clinical Immunology, vol. 98, No. 2, Feb. 2001, pp. 164-174.
Frigault, M. J. et al., "Predicting Cytokine Storms: IT'S About Density", Blood, 118:6724-26(2011).
Goldwater, R., et al., "A Phase 1, Randomized Ascending Single-Dose Study of Antagonist Anti-Human CD40 ASKP1240 in Healthy Subjects,", Am. J. Transplant 2013; 13:1040-1046.
Suntharalingam, G.et al., "Cytokine Storm in a Phase 1 Trial of the Anti-CD28 Monoclonal Antiibody TGN1412", N. Engl., J.Med. 355:1018-28(2006).
Thomas Hunig, The Storm Has Cleared: Lessons From the CD28 Superagonist TGN1412 Trial, Nature Rev. Immunology 12:317-318(2012).
Vonderheide, R.H. et al., "Agonistic CD40 Antibodies and Cancertherapy", Clin. Cancer Res; 19(5):1035-43, 1040, (2013).
Vonderheide, R.H., et al., "Phase I Study of TE CD40 Agonist Antibody CP-870,893 Combined With Carboplatin and Paclitaxel in Patients With Advanced Solid Tumors", Oncoimmunology 2:1, e23033; Jan. 2013; pp. 1-10.

* cited by examiner

Fig. 1A-1

| Sequence | 2105 | KM643-4-11 | F2-103 | 110 | KM341-1-19 |
|---|---|---|---|---|---|
| 1. EPPTACREKQYLI | 16353 | 13220 | 31427 | 13403 | 14108 |
| 2. PTACREKQYLINS | 17358 | 13220 | 39202 | 13575 | 14194 |
| 3. ACREKQYLINSQC | 20267 | 13212 | 35911 | 13681 | 14013 |
| 4. REKQYLINSQCCS | 17096 | 13305 | 43762 | 13685 | 13952 |
| 5. KQYLINSQCCSLC | 23249 | 13292 | 36839 | 13894 | 13779 |
| 6. YLINSQCCSLCQP | 16140 | 13470 | 44975 | 13964 | 13909 |
| 7. INSQCCSLCQPGQ | 15918 | 13390 | 54811 | 13652 | 13751 |
| 8. SQCCSLCQPGQKL | 18804 | 13271 | 60441 | 13872 | 13819 |
| 9. CCSLCQPGQKLVS | 16534 | 13436 | 56601 | 13821 | 13851 |
| 10. SLCQPGQKLVSDC | 18155 | 13314 | 54718 | 13705 | 13965 |
| 11. CQPGQKLVSDCTE | 17614 | 13460 | 52073 | 13699 | 13781 |
| 12. PGQKLVSDCTEFT | 91270 | 13334 | 58177 | 13464 | 13725 |
| 13. QKLVSDCTEFTET | 96926 | 13465 | 49003 | 14916 | 13875 |
| 14. LVSDCTEFTETEC | 141877 | 13634 | 62580 | 13394 | 13783 |
| 15. SDCTEFTETECLP | 148692 | 13213 | 42916 | 13571 | 13696 |
| 16. CTEFTETECLPCG | 145926 | 13591 | 38170 | 13220 | 13824 |
| 17. EFTETECLPCGES | 136350 | 13593 | 56597 | 13434 | 13638 |
| 18. TETECLPCGESEF | 77805 | 13298 | 33201 | 13398 | 13723 |
| 19. TECLPCGESEFLD | 50648 | 13544 | 29781 | 13488 | 13685 |
| 20. CLPCGESEFLDTW | 79246 | 13736 | 26075 | 13599 | 13807 |
| 21. PCGESEFLDTWNR | 93482 | 13626 | 44337 | 16142 | 13830 |
| 22. GESEFLDTWNRET | 68932 | 14815 | 45811 | 13777 | 13832 |
| 23. SEFLDTWNRETHC | 105899 | 13777 | 40462 | 14023 | 13898 |
| 24. FLDTWNRETHCHQ | 55803 | 15498 | 79990 | 40210 | 13937 |
| 25. DTWNRETHCHQHK | 19237 | 13367 | 34525 | 13995 | 13737 |
| 26. WNRETHCHQHKYC | 22963 | 13843 | 32912 | 15601 | 13595 |
| 27. RETHCHQHKYCDP | 16522 | 13282 | 41600 | 13644 | 13595 |
| 28. THCHQHKYCDPNL | 25181 | 13211 | 32264 | 13567 | 13621 |
| 29. CHQHKYCDPNLGL | 16455 | 13300 | 34480 | 13684 | 13671 |
| 30. QHKYCDPNLGLRV | 16627 | 13541 | 39057 | 13461 | 13670 |
| 31. KYCDPNLGLRVQQ | 16429 | 13491 | 46485 | 13452 | 13779 |
| 32. CDPNLGLRVQQKG | 16877 | 13454 | 90926 | 13293 | 13799 |
| 33. PNLGLRVQQKGTS | 18117 | 13611 | 123330 | 13358 | 13917 |
| 34. LGLRVQQKGTSET | 22898 | 13512 | 237353 | 13381 | 15032 |
| 35. LRVQQKGTSETDT | 24787 | 13599 | 250401 | 13364 | 13774 |
| 36. VQQKGTSETDTIC | 28492 | 13372 | 35303 | 13124 | 13686 |
| 37. QKGTSETDTICTC | 27724 | 13490 | 35334 | 13298 | 13569 |
| 38. GTSETDTICTCEE | 18834 | 13340 | 29905 | 13289 | 13525 |
| 39. SETDTICTCEEGW | 16914 | 13340 | 24871 | 13315 | 13486 |
| 40. TDTICTCEEGWHC | 17866 | 13568 | 24475 | 13481 | 13631 |

Fig. 1A-2

| Sequence | 2105 | KM643-4-11 | F2-103 | 110 | KM341-1-19 |
|---|---|---|---|---|---|
| 41. TICTCEEGWHCTS | 18122 | 13767 | 24169 | 13564 | 68670 |
| 42. CTCEEGWHCTSEA | 17485 | 18955 | 28190 | 13736 | 75214 |
| 43. CEEGWHCTSEACE | 16859 | 41843 | 32056 | 13525 | 16033 |
| 44. EGWHCTSEACESC | 17735 | 13381 | 35518 | 13771 | 13867 |
| 45. WHCTSEACESCVL | 64890 | 13444 | 38190 | 13708 | 13687 |
| 46. CTSEACESCVLHR | 16788 | 13446 | 39497 | 13859 | 13636 |
| 47. SEACESCVLHRSC | 16421 | 13555 | 40206 | 13482 | 13584 |
| 48. ACESCVLHRSCSP | 15795 | 13183 | 36735 | 13503 | 13575 |
| 49. ESCVLHRSCSPGF | 47038 | 13504 | 41251 | 14500 | 13637 |
| 50. CVLHRSCSPGFGV | 17469 | 13279 | 45795 | 13484 | 13573 |
| 51. LHRSCSPGFGVKQ | 16635 | 13382 | 88644 | 13187 | 13567 |
| 52. RSCSPGFGVKQIA | 16642 | 13339 | 114128 | 13368 | 13623 |
| 53. CSPGFGVKQIATG | 17457 | 13485 | 110624 | 13323 | 13703 |
| 54. PGFGVKQIATGVS | 18818 | 13577 | 253876 | 13234 | 13769 |
| 55. FGVKQIATGVSDT | 20521 | 13429 | 697242 | 13178 | 13903 |
| 56. VKQIATGVSDTIC | 20855 | 13510 | 91544 | 13176 | 13681 |
| 57. QIATGVSDTICEP | 19014 | 13523 | 40193 | 13154 | 13575 |
| 58. ATGVSDTICEPCP | 17139 | 13526 | 38012 | 13127 | 13599 |
| 59. GVSDTICEPCPVG | 16515 | 13508 | 31118 | 13376 | 13571 |
| 60. SDTICEPCPVGFF | 42762 | 13590 | 25542 | 13392 | 13534 |
| 61. TICEPCPVGFFSN | 25039 | 13366 | 27921 | 13524 | 13783 |
| 62. CEPCPVGFFSNVS | 18141 | 13429 | 31377 | 14364 | 13717 |
| 63. PCPVGFFSNVSSA | 20806 | 13343 | 51411 | 19243 | 13979 |
| 64. PVGFFSNVSSAFE | 95541 | 14553 | 128669 | 158203 | 14523 |
| 65. GFFSNVSSAFEKC | 67908 | 13506 | 94016 | 14323 | 13831 |
| 66. FSNVSSAFEKCHP | 22379 | 13350 | 124184 | 14057 | 13699 |
| 67. NVSSAFEKCHPWT | 18703 | 13298 | 44966 | 13518 | 13676 |
| 68. SSAFEKCHPWTSC | 19809 | 13459 | 37784 | 13433 | 13553 |
| 69. AFEKCHPWTSCET | 16212 | 13387 | 38013 | 13279 | 13683 |
| 70. EKCHPWTSCETKD | 15198 | 13423 | 39248 | 13315 | 13494 |
| 71. CHPWTSCETKDLV | 15754 | 13383 | 40627 | 13228 | 13673 |
| 72. PWTSCETKDLVVQ | 15609 | 13426 | 46662 | 13247 | 13613 |
| 73. TSCETKDLVVQQA | 16454 | 13377 | 46750 | 13228 | 13670 |
| 74. CETKDLVVQQAGT | 16875 | 13544 | 42504 | 13185 | 13700 |
| 75. TKDLVVQQAGTNK | 17357 | 14026 | 83860 | 13184 | 13674 |
| 76. DLVVQQAGTNKTD | 17735 | 13434 | 34853 | 13154 | 13776 |
| 77. VVQQAGTNKTDVV | 17176 | 13805 | 51573 | 13166 | 13651 |
| 78. QQAGTNKTDVVCG | 15794 | 13261 | 27337 | 13103 | 13398 |
| 79. AGTNKTDVVCGPQ | 15793 | 13448 | 25989 | 13304 | 13658 |
| 80. TNKTDVVCGPQDR | 15114 | 13481 | 24807 | 13199 | 13767 |
| 81. KTDVVCGPQDRLR | 15782 | 13328 | 35951 | 13548 | 14112 |
| 82. DVVCGPQDRLRAL | 16644 | 13255 | 33393 | 13756 | 14104 |

Fig. 1B-1

| Sequence | F4-465 | 281-1-10 | 2B11 | F72 | F76 | 4D11 |
|---|---|---|---|---|---|---|
| 1. EPPTACREKQYLI | 20561 | 4194 | 14158 | 3965 | 3348 | 14138 |
| 2. PTACREKQYLINS | 19249 | 4141 | 14276 | 3906 | 3420 | 14387 |
| 3. ACREKQYLINSQC | 20418 | 4221 | 14276 | 3884 | 3300 | 14044 |
| 4. REKQYLINSQCCS | 20278 | 4080 | 14214 | 3849 | 3546 | 13956 |
| 5. KQYLINSQCCSLC | 19642 | 4169 | 14082 | 3806 | 3378 | 14443 |
| 6. YLINSQCCSLCQP | 19658 | 4184 | 14231 | 4082 | 3464 | 14432 |
| 7. INSQCCSLCQPGQ | 18482 | 4603 | 13927 | 3986 | 3157 | 13783 |
| 8. SQCCSLCQPGQKL | 19075 | 4326 | 13748 | 3934 | 3675 | 13471 |
| 9. CCSLCQPGQKLVS | 20282 | 4349 | 13578 | 4046 | 3336 | 13431 |
| 10. SLCQPGQKLVSDC | 20175 | 4841 | 13522 | 3948 | 3222 | 13387 |
| 11. CQPGQKLVSDCTE | 22520 | 4576 | 13441 | 4115 | 3566 | 13339 |
| 12. PGQKLVSDCTEFT | 23688 | 4499 | 13618 | 4012 | 3525 | 13290 |
| 13. QKLVSDCTEFTET | 22029 | 4771 | 13528 | 4294 | 3539 | 13450 |
| 14. LVSDCTEFTETEC | 23692 | 5212 | 13439 | 4177 | 3601 | 14898 |
| 15. SDCTEFTETECLP | 25950 | 4864 | 13359 | 4095 | 3362 | 13277 |
| 16. CTEFTETECLPCG | 20943 | 4906 | 13496 | 4121 | 3582 | 13874 |
| 17. EFTETECLPCGES | 37123 | 4748 | 13570 | 3960 | 3402 | 16583 |
| 18. TETECLPCGESEF | 23400 | 4807 | 13444 | 3811 | 3407 | 13808 |
| 19. TECLPCGESEFLD | 21427 | 4649 | 13352 | 3970 | 3288 | 13566 |
| 20. CLPCGESEFLDTW | 18021 | 4794 | 19449 | 3940 | 5926 | 47209 |
| 21. PCGESEFLDTWNR | 26480 | 7656 | 86887 | 5478 | 16438 | 165895 |
| 22. GESEFLDTWNRET | 25229 | 4906 | 24124 | 4337 | 4362 | 32083 |
| 23. SEFLDTWNRETHC | 23274 | 5979 | 30344 | 4138 | 4083 | 72724 |
| 24. FLDTWNRETHCHQ | 28280 | 19544 | 120439 | 4636 | 6401 | 336496 |
| 25. DTWNRETHCHQHK | 20114 | 4107 | 14285 | 4029 | 3459 | 14028 |
| 26. WNRETHCHQHKYC | 21110 | 4714 | 16070 | 4111 | 3819 | 25715 |
| 27. RETHCHQHKYCDP | 19452 | 4075 | 13942 | 4000 | 3252 | 13812 |
| 28. THCHQHKYCDPNL | 18412 | 4221 | 14203 | 3912 | 3459 | 14295 |
| 29. CHQHKYCDPNLGL | 18890 | 4288 | 16566 | 4025 | 3473 | 13886 |
| 30. QHKYCDPNLGLRV | 19296 | 4313 | 13580 | 4132 | 3383 | 13355 |
| 31. KYCDPNLGLRVQQ | 20430 | 4460 | 13469 | 4254 | 3651 | 13357 |
| 32. CDPNLGLRVQQKG | 28700 | 4570 | 13568 | 5394 | 4575 | 13336 |
| 33. PNLGLRVQQKGTS | 39822 | 5229 | 13590 | 24278 | 6996 | 13404 |
| 34. LGLRVQQKGTSET | 52908 | 4681 | 13651 | 7042 | 4112 | 13400 |
| 35. LRVQQKGTSETDT | 56985 | 4376 | 13514 | 4839 | 16679 | 13557 |
| 36. VQQKGTSETDTIC | 21684 | 4531 | 13423 | 3960 | 3258 | 13355 |
| 37. QKGTSETDTICTC | 21838 | 4509 | 13507 | 3975 | 3355 | 13365 |
| 38. GTSETDTICTCEE | 21896 | 4074 | 13348 | 3856 | 3298 | 13453 |
| 39. SETDTICTCEEGW | 18789 | 4082 | 13377 | 3687 | 3297 | 13606 |
| 40. TDTICTCEEGWHC | 17729 | 4187 | 13485 | 3756 | 3638 | 19679 |

Fig. 1B-2

| Sequence | F4-465 | 281-1-10 | 2B11 | F72 | F76 | 4D11 |
|---|---|---|---|---|---|---|
| 41. TICTCEEGWHCTS | 22932 | 4207 | 14559 | 4151 | 3992 | 46128 |
| 42. CTCEEGWHCTSEA | 22823 | 4167 | 14428 | 4077 | 3394 | 14309 |
| 43. CEEGWHCTSEACE | 25545 | 4071 | 14192 | 4118 | 3375 | 14162 |
| 44. EGWHCTSEACESC | 23461 | 4272 | 14290 | 4171 | 3393 | 14029 |
| 45. WHCTSEACESCVL | 20999 | 4198 | 14136 | 4318 | 3465 | 14065 |
| 46. CTSEACESCVLHR | 20553 | 4273 | 14301 | 4152 | 3396 | 14337 |
| 47. SEACESCVLHRSC | 20792 | 4234 | 13900 | 4122 | 3439 | 13877 |
| 48. ACESCVLHRSCSP | 21816 | 4179 | 13741 | 3934 | 3525 | 13539 |
| 49. ESCVLHRSCSPGF | 20599 | 4725 | 13758 | 4141 | 3514 | 13658 |
| 50. CVLHRSCSPGFGV | 19851 | 4393 | 13533 | 4127 | 3526 | 13320 |
| 51. LHRSCSPGFGVKQ | 23160 | 4317 | 13486 | 4851 | 18376 | 13355 |
| 52. RSCSPGFGVKQIA | 24797 | 4495 | 13728 | 5568 | 15564 | 13375 |
| 53. CSPGFGVKQIATG | 30890 | 4962 | 13400 | 8711 | 3383 | 13340 |
| 54. PGFGVKQIATGVS | 82448 | 5027 | 13415 | 11404 | 4102 | 13378 |
| 55. FGVKQIATGVSDT | 126309 | 4541 | 13423 | 4896 | 3515 | 13474 |
| 56. VKQIATGVSDTIC | 32389 | 4361 | 13454 | 4040 | 3278 | 13305 |
| 57. QIATGVSDTICEP | 28554 | 4308 | 13325 | 3807 | 3318 | 13350 |
| 58. ATGVSDTICEPCP | 22484 | 4176 | 13463 | 3868 | 3241 | 13399 |
| 59. GVSDTICEPCPVG | 21417 | 4277 | 13329 | 3584 | 3259 | 13475 |
| 60. SDTICEPCPVGFF | 20192 | 4360 | 13337 | 3725 | 3358 | 14425 |
| 61. TICEPCPVGFFSN | 25475 | 4390 | 14453 | 4101 | 3446 | 15502 |
| 62. CEPCPVGFFSNVS | 26387 | 4419 | 14370 | 4434 | 3538 | 14441 |
| 63. PCPVGFFSNVSSA | 40241 | 4468 | 14425 | 4363 | 3409 | 14664 |
| 64. PVGFFSNVSSAFE | 27432 | 11225 | 85432 | 4772 | 5735 | 49493 |
| 65. GFFSNVSSAFEKC | 77408 | 4483 | 14462 | 4173 | 3489 | 14521 |
| 66. FSNVSSAFEKCHP | 57923 | 4088 | 14050 | 4230 | 3296 | 13989 |
| 67. NVSSAFEKCHPWT | 23154 | 4031 | 13752 | 4025 | 3343 | 13619 |
| 68. SSAFEKCHPWTSC | 20994 | 4170 | 13512 | 4006 | 3419 | 13466 |
| 69. AFEKCHPWTSCET | 21390 | 4498 | 13629 | 4028 | 3413 | 13518 |
| 70. EKCHPWTSCETKD | 19639 | 4186 | 13571 | 3911 | 3403 | 16038 |
| 71. CHPWTSCETKDLV | 20967 | 4216 | 13608 | 4177 | 3489 | 13283 |
| 72. PWTSCETKDLVVQ | 23271 | 4300 | 13420 | 4459 | 3316 | 13507 |
| 73. TSCETKDLVVQQA | 26353 | 4690 | 13457 | 4411 | 3496 | 13462 |
| 74. CETKDLVVQQAGT | 26955 | 4517 | 13389 | 4600 | 3403 | 13433 |
| 75. TKDLVVQQAGTNK | 63164 | 6695 | 13475 | 60382 | 7609 | 13271 |
| 76. DLVVQQAGTNKTD | 25820 | 4567 | 13537 | 4057 | 3585 | 13328 |
| 77. VVQQAGTNKTDVV | 28426 | 4587 | 13372 | 4179 | 3418 | 13309 |
| 78. QQAGTNKTDVVCG | 19474 | 4111 | 13455 | 3709 | 3809 | 13332 |
| 79. AGTNKTDVVCGPQ | 18988 | 4186 | 13517 | 3868 | 3231 | 13436 |
| 80. TNKTDVVCGPQDR | 18178 | 4662 | 13423 | 3654 | 4897 | 13350 |
| 81. KTDVVCGPQDRLR | 27431 | 4208 | 13879 | 4242 | 4238 | 13779 |
| 82. DVVCGPQDRLRAL | 28872 | 4127 | 14128 | 4179 | 3459 | 13855 |

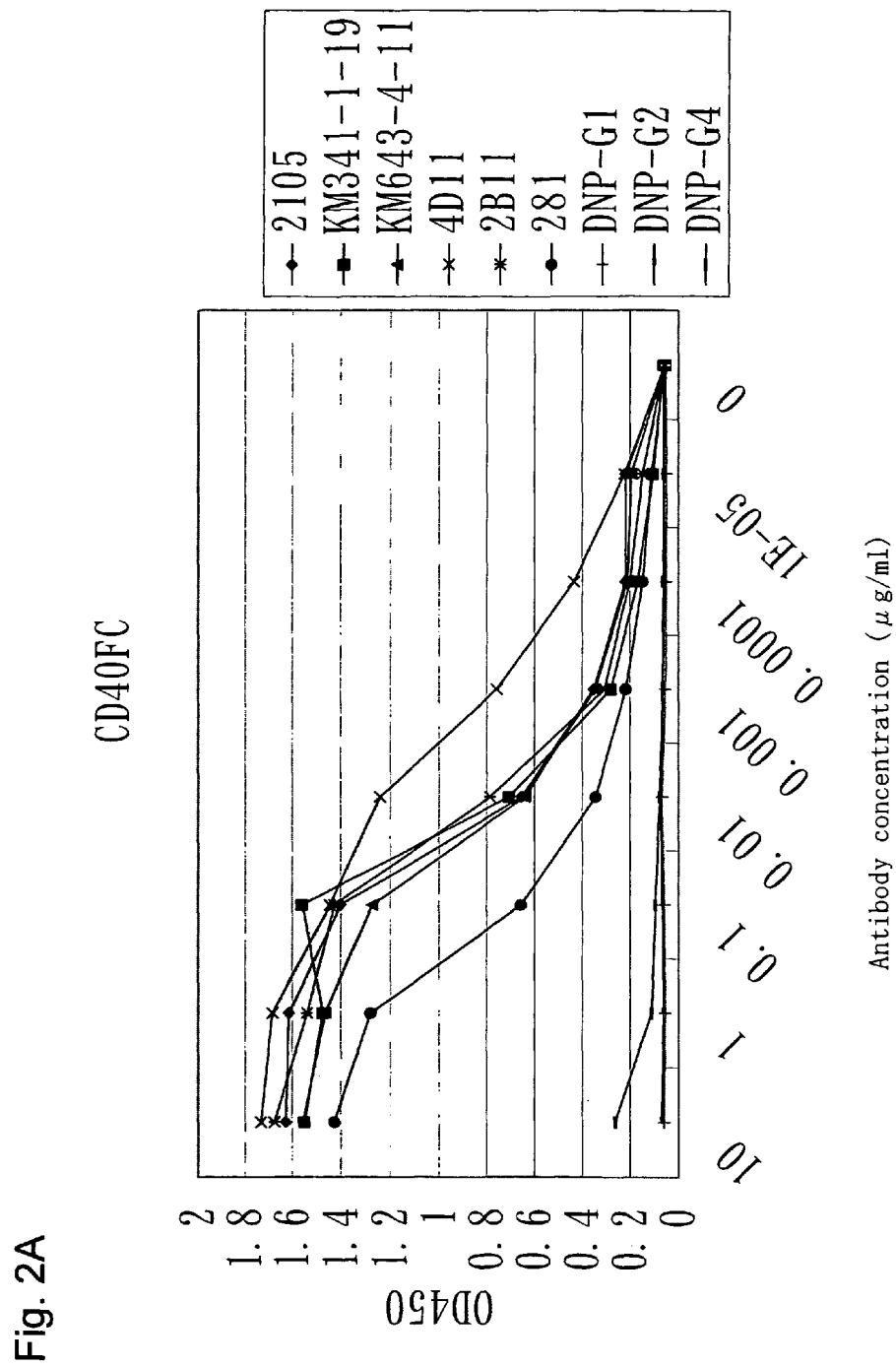

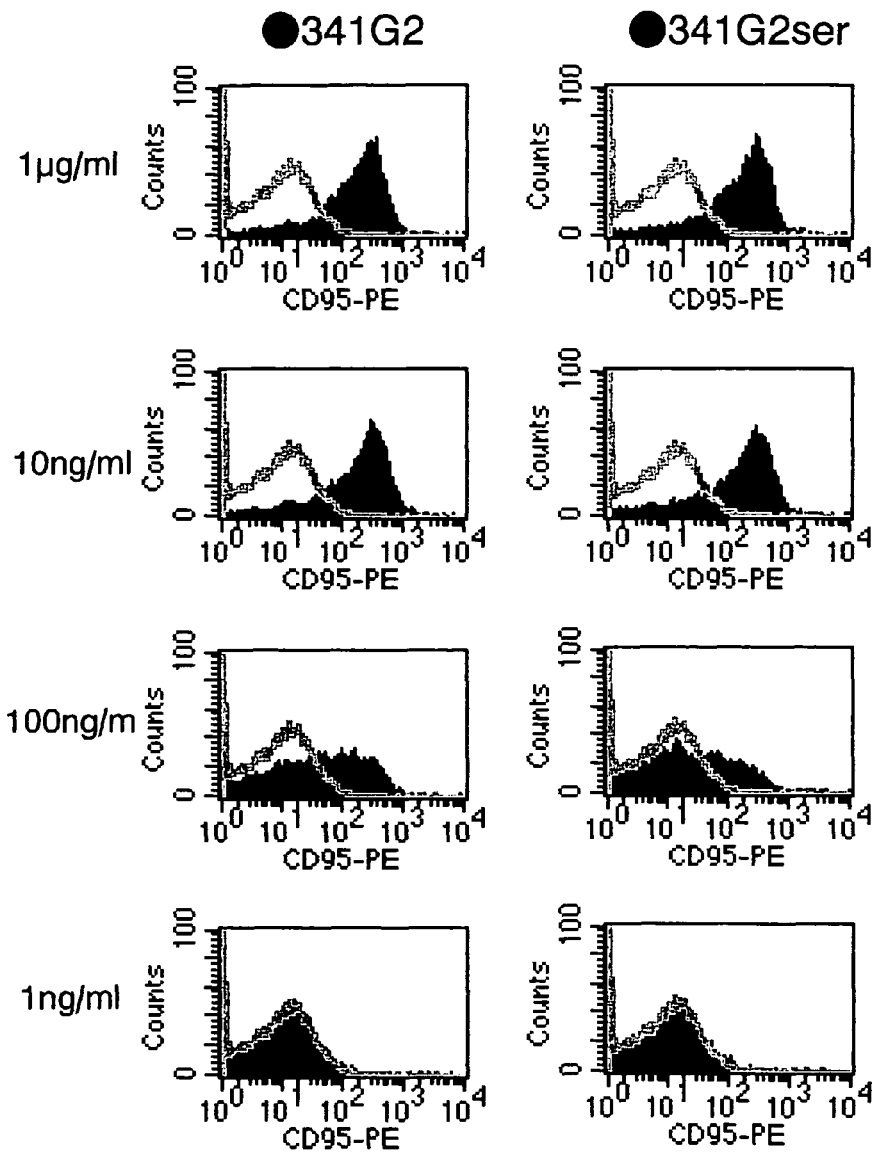

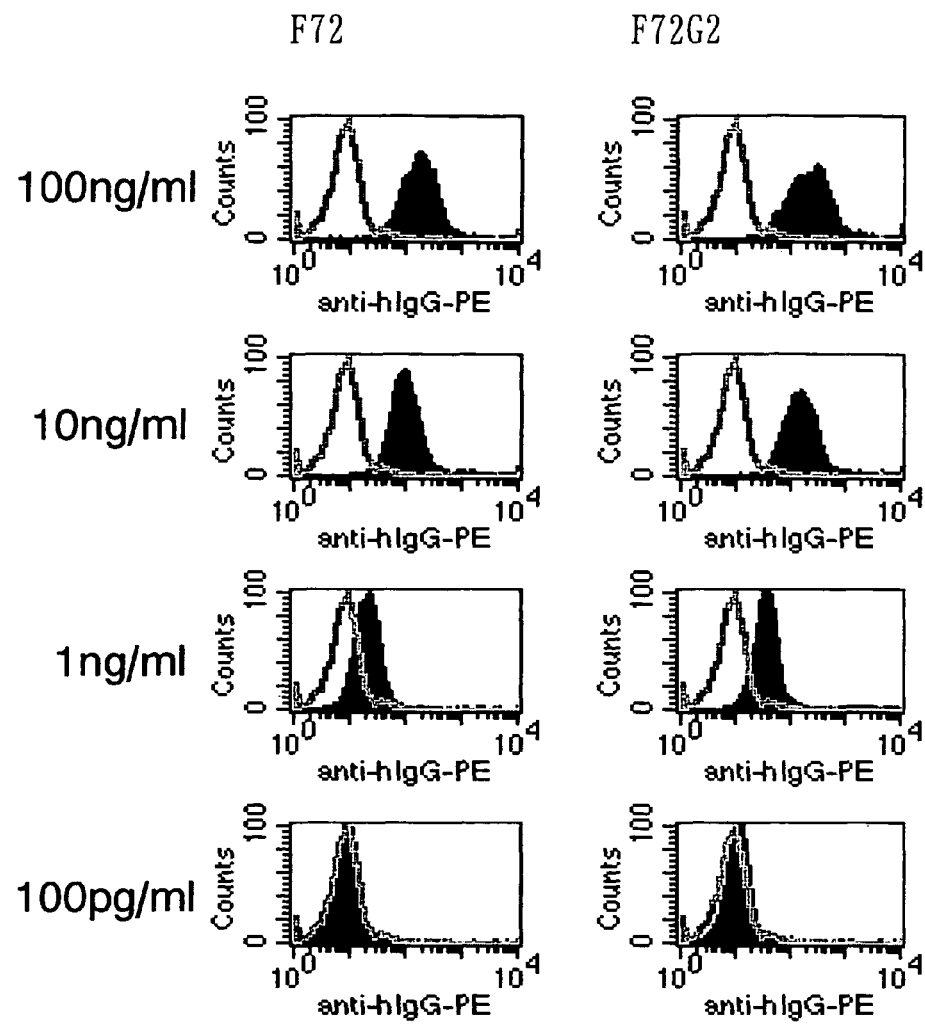

Fig. 17

| Group (mg/kg) | Treatment | | | Average score* | |
|---|---|---|---|---|---|
| | Tetanus toxoid | | | | |
| | Sensitization Dorsal intradermal | Intramuscular | Abdominal intradermal challenge | 24 hrs** | 48 hrs** |
| Control | 10 µL/site x 12 sites | 0.6 mL/animal | 0 Lf/mL | 0.00 | 0.00 |
| | | | 1 Lf/mL | 1.67 | 1.00 |
| | | | 3 Lf/mL | 3.00 | 2.67 |
| | | | 10 Lf/mL | 3.33 | 3.00 |
| 4D11 1 (mg/kg) | 10 µL/site x 12 sites | 0.6 mL/animal | 0 Lf/mL | 0.00 | 0.00 |
| | | | 1 Lf/mL | 0.67 | 0.67 |
| | | | 3 Lf/mL | 1.00 | 0.67 |
| | | | 10 Lf/mL | 1.00 | 1.00 |
| 4D11 10 (mg/kg) | 10 µL/site x 12 sites | 0.6 mL/animal | 0 Lf/mL | 0.00 | 0.00 |
| | | | 1 Lf/mL | 0.00 | 0.00 |
| | | | 3 Lf/mL | 0.67 | 0.33 |
| | | | 10 Lf/mL | 1.00 | 0.67 |

Remarks:
\* Response score
formation of erythema and/or eschar
no erythema : 0
very slight erythema (barely perceptible) : 1
well-defined erythema : 2
moderate to severe erythema : 3
from severe erythema to slight crust (deep injury) : 4 formation of edema
no edema : 0
very slight edema (barely perceptible) : 1
slight edema (edges of area well defined by definite raising) : 2
moderate edema (raised about 1 mm) : 3
severe edema (raised 1 mm or more and extending beyond area of exposure) : 4

\*\* time after challenge

Fig. 18

(Maximum dilution rate for positive effect)

| Group | Animal No. | pre | 4 | 7 | Days after the 1st dose 11 | 14 | 18 | 21 | 23 |
|---|---|---|---|---|---|---|---|---|---|
| Control | 1 | 0 | 200 | 0 | 12800 | 102400 | 204800 | 204800 | 204800 |
|  | 2 | 0 | 0 | 0 | 6400 | 25600 | 51200 | 51200 | 51200 |
|  | 3 | 0 | 0 | 0 | 6400 | 12800 | 25600 | 25600 | 25600 |
|  | Mean | 0 | 67 | 0 | 8533 | 46933 | 93867 | 93867 | 93867 |
|  | S.D. | 0 | 115 | 0 | 3695 | 48460 | 96920 | 96920 | 96920 |
| 1 (mg/kg) | 4 | 0 | 0 | 0 | 200 | 1600 | 12800 | 12800 | 12800 |
|  | 5 | 0 | 0 | 0 | 200 | 400 | 6400 | 6400 | 6400 |
|  | 6 | 0 | 0 | 0 | 400 | 3200 | 6400 | 6400 | 6400 |
|  | Mean | 0 | 0 | 0 | 267 | 1733 | 8533 | 8533 | 8533 |
|  | S.D. | 0 | 0 | 0 | 115 | 1405 | 3695 | 3695 | 3695 |
| 10 (mg/kg) | 7 | 0 | 0 | 0 | 0 | 0 | 0 | 0 | 0 |
|  | 8 | 0 | 0 | 0 | 0 | 0 | 0 | 0 | 0 |
|  | 9 | 0 | 0 | 0 | 0 | 0 | 0 | 0 | 0 |
|  | Mean | 0 | 0 | 0 | 0 | 0 | 0 | 0 | 0 |
|  | S.D. | 0 | 0 | 0 | 0 | 0 | 0 | 0 | 0 |

Fig. 19

(Maximum dilution rate for positive effect)

| Group | Animal No. | pre | 4 | 7 | 11 | 14 | 18 | 21 | 23 |
|---|---|---|---|---|---|---|---|---|---|
| Control | 1 | 0 | 0 | 0 | 3200 | 6400 | 6400 | 6400 | 6400 |
|  | 2 | 0 | 0 | 0 | 1600 | 1600 | 1600 | 1600 | 800 |
|  | 3 | 0 | 0 | 0 | 800 | 1600 | 1600 | 1600 | 1600 |
|  | Mean | 0 | 0 | 0 | 1867 | 3200 | 3200 | 3200 | 2933 |
|  | S.D. | 0 | 0 | 0 | 1222 | 2771 | 2771 | 2771 | 3029 |
| 1 (mg/kg) | 4 | 0 | 0 | 0 | 0 | 0 | 400 | 0 | 0 |
|  | 5 | 0 | 0 | 0 | 0 | 0 | 0 | 0 | 0 |
|  | 6 | 0 | 0 | 0 | 0 | 800 | 800 | 800 | 800 |
|  | Mean | 0 | 0 | 0 | 0 | 267 | 400 | 267 | 267 |
|  | S.D. | 0 | 0 | 0 | 0 | 462 | 400 | 462 | 462 |
| 10 (mg/kg) | 7 | 0 | 0 | 0 | 0 | 0 | 0 | 0 | 0 |
|  | 8 | 0 | 0 | 0 | 0 | 0 | 0 | 0 | 0 |
|  | 9 | 0 | 0 | 0 | 0 | 0 | 0 | 0 | 0 |
|  | Mean | 0 | 0 | 0 | 0 | 0 | 0 | 0 | 0 |
|  | S.D. | 0 | 0 | 0 | 0 | 0 | 0 | 0 | 0 |

Days after the 1st dose

Fig. 20A
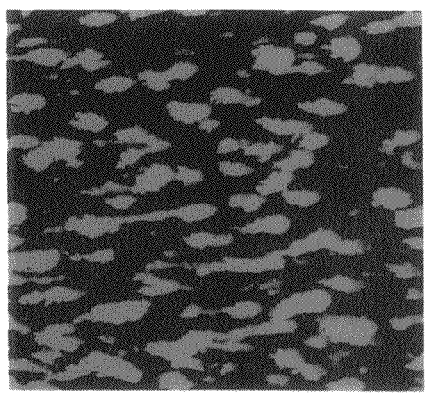
Human control IgG4
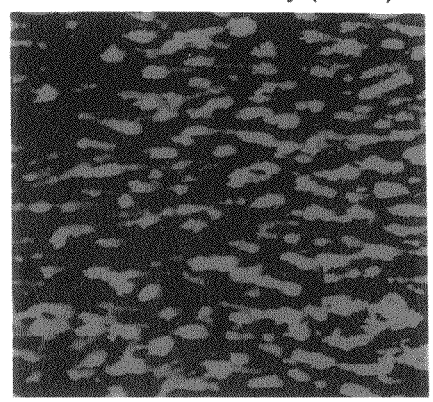
Anti-CD40 antibody (4D11)
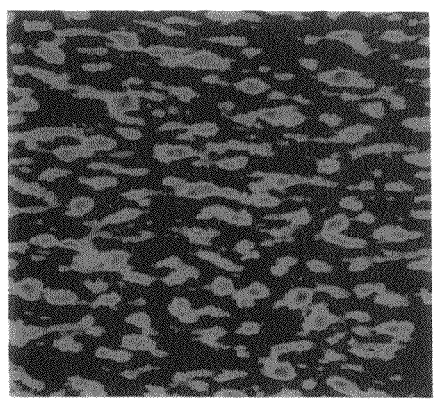
Murine control IgG2
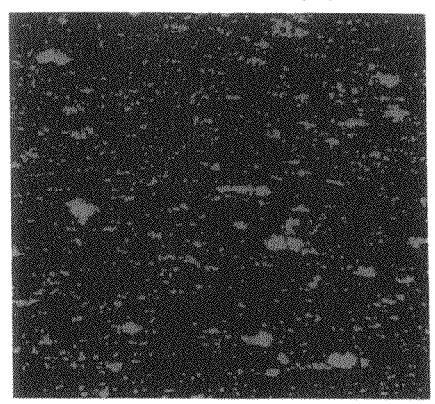
Anti-CD40L antibody (5C8)

METHOD OF TREATING TRANSPLANT REJECTION WITH AN ANTI-CD40 ANTIBODY

TECHNICAL FIELD

The present invention relates to an anti-CD40 antibody which recognizes CD40 which is a type of cell membrane molecules associated with immunity. Further, the present invention relates to an antibody with a mutation in the constant region of the human antibody or with a subclass having its portion substituted in order to decrease an ADCC and/or CDC activity, while keeping an agonistic or antagonistic activity.

BACKGROUND ART

1. CD40

CD40 is an antigen having a molecular weight of 50 kDa which is present on the surface of cell membrane, and expressed in B cells, dendritic cells (DCs), some types of cancer cells, and thymic epithelial cells. CD40 is known to play an important role in proliferation and differentiation of B cells and DCs. CD40 was identified as an antigen expressed on the surface of human B cells (E. A. Clark et al., Proc. Natl. Acad. Sci. USA 83: 4494, 1986; and I. Stamenkovic et al., EMBO J. 8: 1403, 1989) and has been considered as a member of the TNF receptor family which includes low-affinity NGF receptors, TNF receptors, CD27, OX40 and CD30. Ligands (CD40Ls) to human and murine CD40s have been recently cloned and found to be membrane proteins type II and expressed in activated CD4+T cells. CD40L has been also found to introduce strong signals for activation into human or murine B cells.

In dendritic cells, CD40 has been observed to be more highly expressed than in B cells, and it has become clear that CD40 plays an important role in dendritic cells. Binding of CD40 to CD40L activates antigen presenting cells (APCs), that is, expresses costimulator molecules such as CD80 (B7-1) and CD86 (B7-2) or enhances production of IL-2 (Caux, C., et al.: Activation of human dendritic cells through CD40 cross-linking. J. Exp. Med., 180: 1263, 1994; and Shu, U., et al.: Activated T cells induce interleukin-12 production by monocyte via CD40 - CD40 ligand interaction. Eur. J. Immunol., 25: 1125, 1995). Dendritic cells have a strong antigen-presenting capacity and a strong capacity to activate helper T (Th) cells. Dendritic cells are also believed to control differentiation of naive Th cells into Th1 or Th2 cells. When peripheral blood monocytes, which are myeloid dendritic cells, are cultured in the presence of GM-CSF and IL-4, and matured by CD40L, the resulting matured dendritic cells (DC 1) can produce IL-12 in vitro, and stimulate and activate allogeneic naive Th cells to induce IFNγ-producing T cells (i.e., to promote their differentiation into Th1). This action is inhibited by anti-IL-12 antibody and hence may be effected via IL-12. On the other hand, when plasmacytoid T cells, which are present in lymphoid T regions and peripheral blood, are cultured in the presence of IL-3 and CD40 ligand, the resulting lymphoid dendritic cells (DC2) are shown to be unable to produce IL-12, and stimulate and activate allogeneic naive Th cells to induce IL-4-producing T cells, which indicates promotion of their differentiation into Th2. It is believed that Th1 cells are involved in activation of cellular immunity, while Th2 cells are associated with enhancement of humoral immunity as well as restriction of cellular immunity. When cytotoxic T cells (CTL) are activated with the help of Th1 cells, they may eliminate pathogens (a number of types of virus, listeria, tuberculosis bacteria, toxoplasma protozoa, etc.) growing in the cytoplasm and tumor cells.

Monoclonal anti-CD40 antibodies, which recognize CD40 expressed on the membrane surface, have been demonstrated to have different biological activities to B cells. Monoclonal anti-CD40 antibodies are generally classified into agonistic or antagonistic antibodies against the interaction between CD40 and CD40L.

2. Agonistic Antibodies

Agonistic antibodies are known to activate B cells. For instance, the anti-CD40 antibodies are reported to induce cell adhesion (Barrett et al., J. Immunol. 146: 1722, 1991; and Gordon et al., J. Immunol. 140: 1425, 1998), increase cell size (Gordon et al., J. Immunol. 140: 1425, 1998; and Valle et al., Eur. J. Immunol. 19: 1463, 1989), induce cell division of B cells activated only by an anti-IgM antibody, anti-CD20 antibody or phorbol ester (Clark and Ledbetter, Proc. Natl. Acad. Sci. USA 83: 4494, 1986; Gordon et al., LEUCOCYTE TYPING III. A. J. McMicheal ed. Oxford University Press. Oxford. p. 426; and Paulie et al., J. Immunol. 142: 590, 1989), induce cell division of B cells in the presence of IL4 (Valle et al., Eur. J. Immunol. 19: 1463, 1989; and Gordon et al., Eur. J. Immunol. 17: 1535, 1987), induce expression of IgE by cultured cells stimulated with IL-4 and deprived of T cells (Jabara et al., J. Exp. Med. 172: 1861, 1990; and Gascan et al., J. Immunol. 147: 8, 1991), induce expression of IgG and IgM by those cultured cells (Gascan et al., J. Immunol. 147: 8, 1991), secrete soluble CD23/FceRII from cells via IL-4 (Gordon and Guy, Immunol. Today 8: 39, 1987; and Cairns et al., Eur. J. Immunol. 18: 349, 1988), enhance expression of soluble CD23/FceRII on the cells via IL4 (Challa, A., Allergy, 54: 576, 1999), and promote IL-6 production (Clark and Shu, J. Immunol. 145: 1400, 1990). Furthermore, it is reported that addition of IL-4 and an anti-CD40 antibody to human primary culture B cells in the presence of CDw32+ adhesive cells led to establishment of cloned B cells derived therefrom (Bancherauet et al., Science 241: 70, 1991), and apoptosis of germinal center cells was inhibited through CD40 irrespective of whether its antigen receptor was active or inactive (Liu et al., Nature 342: 929, 1989). As described above, CD40 has been identified as antigen expressed on the surface of human B cells, and consequently, most of the isolated antibodies have been evaluated, as an index, mainly using their induction potency for proliferation and/or differentiation of human B cells, or their induction activity for cell death of cancer cells (Katira, A. et al., LEUKOCYTE TYPING V. S. F. Schlossossman, et. al. eds. p. 547. Oxford University Press. Oxford; W. C. Flansow et. al., LEUKOCYTE TYPING V. S. F. Schlossossman, et. al. eds. p. 555. Oxford University Press. Oxford; and J. D. Pound et. al., International Immunology, 11: 11, 1999).

The anti-CD40 antibody has been demonstrated to mature DC (Z. H. Zhou et. al., Hybridoma, 18: 471, 1999). Furthermore, the role of CD4 T cells in priming antigen-specific CD8 T cells was reported to be in activation of DC via CD40-CD40L signaling, and the anti-CD40 monoclonal antibody (mAb) has been found to be able to replace CD40 helper T cells in activation of dendritic cells (DC) (Shoenberger, S. P., et. al.: T-cell help for cytotoxic T lymphocytes is mediated by CD40-CD40L interactions. Nature, 480, 1998). Also, administration of an anti-CD40 antibody in mice has been found to be able to protect the animal body from CD40-expressing tumor cells as well as CD40-non-expressing tumor cells (French, R. R., et. al.: CD40 antibody evokes a cytotoxic T-cell response that eradicates lymphoma and bypasses T-cell help. Nature Medicine, 5, 1999).

Agonistic anti-CD40 antibodies are expected to be effective for treatment of infectious diseases, due to bacteria, virus, etc., cancer and others, based on their functions described above. Anti-CD40 antibodies with superior agonistic activities are described in WO 02/088186. The representative examples of those agonistic antibodies are KM341-1-19 and 2105 antibodies. The hybridoma KM341-1-19 producing the KM341-1-19 antibody and the hybridoma 2105 producing the 2105 antibody were submitted on 27, Sep. 2001 and 17, Apr. 2002, respectively, for international deposit under the Budapest Treaty, to International Patent Organisms Depositary, National Institute of Advanced Industrial Science and Technology (central 6, 1-1, Higashi 1, Tsukuba, Ibaraki, Japan). Their accession numbers are FERM BP-7759 (KM341-1-19) and FERM BP-8024 (2105).

3. Antagonistic Antibodies

Taking it in consideration, on the other hand, that CD40 plays an important role in immunologic responses, as aforementioned, it is expected that inhibition of binding of CD40 to its ligands would lead to development of therapeutic agents for immune suppression in organ transplantation and autoimmune diseases. Sawada, Hase and others have reported that the peripheral blood of patients suffering from Crohn's disease has a higher percentage of monocytes highly expressing CD40. However, such antibodies have not been well known yet as inhibit binding of CD40 to its ligands. Those inhibitory antibodies would be useful in functional analysis of CD40 and treatment of diseases requiring activation of CD40. Inhibitory antibodies to CD40 ligands are also suggested to be effective against diseases involving binding of CD40 to the CD40 ligands. However, CD40L was reported to be expressed in activated platelets (V. Henn et al., Nature 391: 591, 1998), and if an anti-CD40L antibody is used as a therapeutic agent, thrombus formation may occur reportedly (T. Kawai et al., Nat. Med. 6: 114, 2000). From this point of view, antibodies to CD40 are expected to be safer rather than anti-CD40L antibodies as therapeutic antibody agent to inhibit binding of CD40 to its ligands. Anti-CD40 antibodies would be required to inhibit binding of CD40L to CD40 and still not activate CD40 in themselves.

Such antagonistic anti-CD40 antibodies may be used for treatment of autoimmune diseases and suppression of immunologic rejections in transplantation of organs, bone marrow, etc., in view of their functions described above. Anti-CD40 antibodies with superior antagonistic activities are described in WO 02/088186. The representative example of those antagonistic antibodies is 4D11 antibody. The hybridoma 4D11 producing the 4D11 antibody was submitted on 27, Sep. 2001 for international deposit under the Budapest Treaty, to International Patent Organisms Depositary, National Institute of Advanced Industrial Science and Technology (central 6, 1-1, Higashi 1, Tsukuba, Ibaraki, Japan). The accession number is FERM BP-7758.

Patent Document 1 WO 02/088186

DISCLOSURE OF THE INVENTION

The object of the present invention is to create mutants from the potentially therapeutic anti-CD40 antibodies disclosed in WO 02/088186, which mutants are designed optimally as pharmaceutical agent.

As a result of extensive and intensive research, the present inventors have successfully created novel mutants of the agonistic or antagonistic antibodies, which mutants may have a higher therapeutic effect against diseases than known anti-CD40 antibodies, and completed the present invention based thereon. The basic idea on modification of the anti-CD40 antibodies according to the present invention will be described in detail below.

The present specification shall encompass the description in the specification and/or drawings of JP Patent Publication (Kokai) No. 2003-431408 which is the basis for the priority of the present application.

BRIEF DESCRIPTION OF THE DRAWINGS

The application contains at least one drawing executed in color. Copies of this patent or patent application publication with color drawing(s) will be provided by the Office upon request and payment of the necessary fee.

FIG. 1A-1 shows binding site peptides (SEQ ID NOs: 49-88) prepared based on the CD40 sequence, to which the anti-CD40 agonistic antibodies bind;

FIG. 1A-2 shows binding site peptides (SEQ ID NOs: 89-130) prepared based on the CD40 sequence, to which the anti-CD40 agonistic antibodies bind (a continuation to FIG. 1A-1);

FIG. 1B-1 shows binding site peptides (SEQ ID NOs: 49-88) prepared based on the CD40 sequence, to which the anti-CD40 antagonistic antibodies bind;

FIG. 1B-2 shows binding site peptides (SEQ ID NOs: 89-130) prepared based on the CD40 sequence, to which the anti-CD40 antagonistic antibodies bind (a continuation to FIG. 1B-1);

FIG. 2A illustrates binding of the anti-CD40 antibodies to the CD40 mutant;

FIG. 3B shows diagrams indicating that the KM341-1-19 antibody having a P331S mutation is as active as the original KM341-1-19 antibody with respect to enhancement of CD95 expression of Ramos cells;

FIG. 5A-1 shows diagrams indicating that conversion of the subclass of the 2105 antibody from IgG2 into different subclasses has no effect on its binding to Ramos cells;

FIG. 5A-2 shows diagrams indicating that conversion of the subclass of the KM341-1-19 antibody from IgG2 into different subclasses has no effect on its binding to Ramos cells;

FIG. 5B-1 shows diagrams indicating that conversion of the subclass of the 2105 antibody from IgG2 into different subclasses lowers an activity to enhance CD95 expression of Ramos cells;

FIG. 5B-2 shows diagrams indicating that conversion of the subclass of the KM341-1-19 antibody from IgG2 into different subclasses lowers an activity to enhance CD95 expression of Ramos cells;

FIG. 6A-1 shows diagrams indicating that the binding capacity of the KM341-1-19 antibodies to Ramos cells is independent of the varying structure of the hinge region;

FIG. 6A-2 shows diagrams indicating that the binding capacity of the 2105 antibodies to Ramos cells is independent of the varying structure of the hinge region;

FIG. 6B-1 shows diagrams indicating that the upper and middle hinges of the hinge region are important for the activity of the KM341-1-19 antibodies to enhance CD95 expression of Ramos cells;

FIG. 6B-2 shows diagrams indicating that the upper and middle hinges of the hinge region are important for the activity of the 2105 antibodies to enhance CD95 expression of Ramos cells;

FIG. 7A shows diagrams indicating that conversion of the subclass of the F72 antibody to IgG2 has no effect on its binding to Ramos cells;

FIG. 17 shows the suppressive effect of 4D11G4PE on the simian DTH (delayed-type hypersensitivity in male cynomolgus monkeys);

FIG. 18 shows the titers of the anti tetanus toxin IgG during the assay with the results shown in FIG. 17;

FIG. 19 shows the titers of the anti tetanus toxin IgM during the assay with the results shown in FIG. 17;

FIG. 20A illustrates the respective influences of 4D11G4PE and 5C8 (anti-CD40Ligand antibody) on platelet aggregation;

BEST MODE FOR CARRYING OUT THE INVENTION

1. Modification of Agonistic Antibodies

Figure 2B:
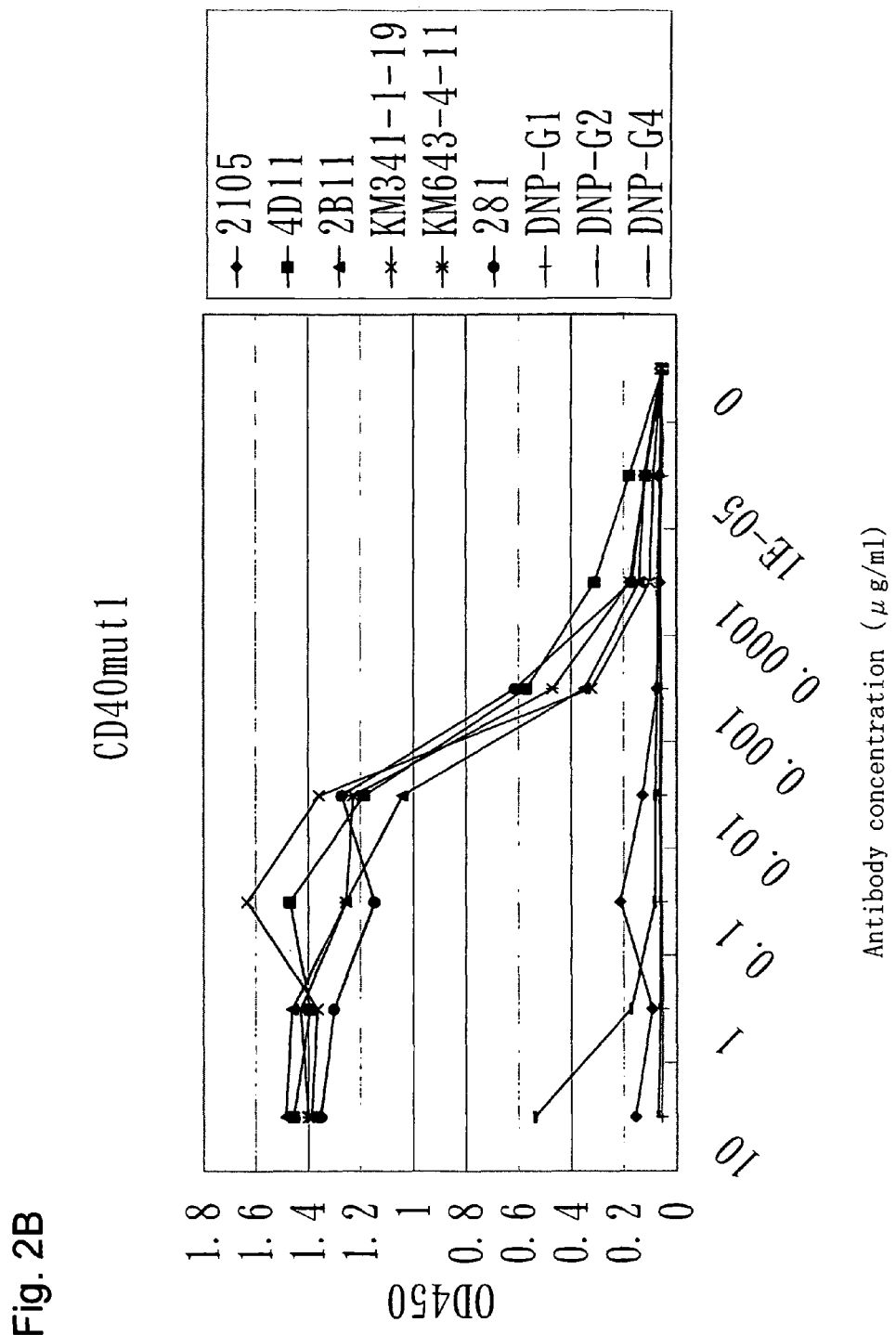
FIG. 2B illustrates binding of the anti-CD40 antibodies to the CD40 mutant.
Figure 2C:
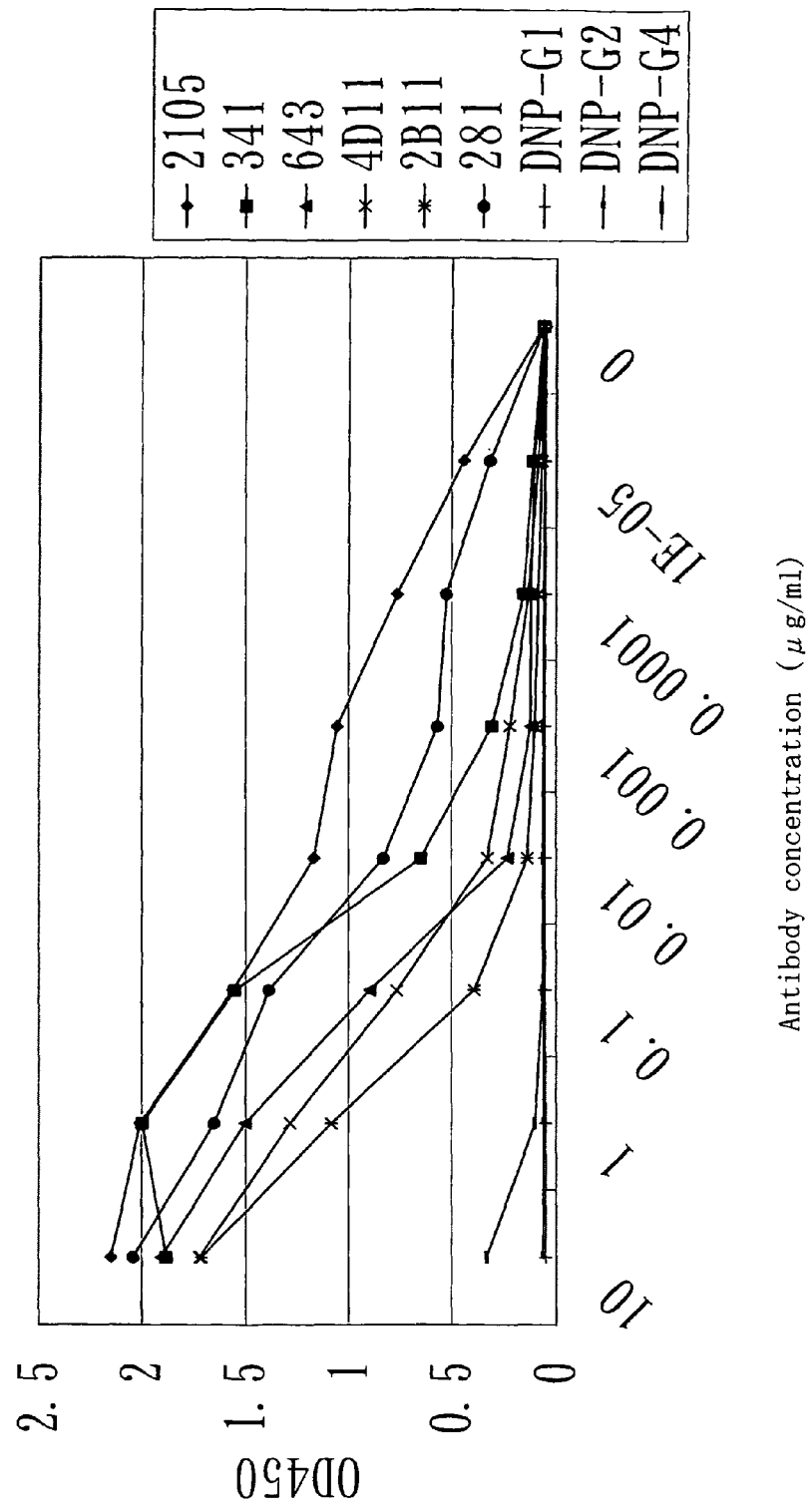
FIG. 2C illustrates binding of the anti-CD40 antibodies to the CD40 mutant.

Antibodies are essentially molecules that function to protect living bodies against foreign bodies, such as microorganisms and viruses, and cancer, and hence they can kill and eliminate such cells binding to themselves. The lethal activity is composed of two different activities, called Antibody-Dependent Cellular Cytotoxicity (abbreviated as ADCC hereinafter) and Complement-Dependent Cytotoxicity (abbreviated as CDC hereinafter).

ADCC refers to a type of cytotoxicity induced by activation of macrophages, NK cells, neutrophil cells, etc., which recognize target cells by binding to the constant region of the antibody via Fc receptors expressed on their surface. In contrast, CDC refers to a type of cytotoxicity induced by activation of a complement system which occurs through binding of an antibody to an antigen. These activities are known to vary depending on a subclass of the antibody, which has been found to be due to a structural difference in the constant region of antibodies (Charles A. Janeway et al., Immunology, 1997, Current Biology Ltd./Garland Publishing Inc.).

Anti-CD40 agonistic antibodies will be more preferable as therapeutic agent if they have not the activities of ADCC and/or CDC which may induce cell death of CD40-expressing cells, in terms of mechanism of immunoactive action. If CD40-expressing cells are injured by ADCC and/or CDC activities, immunosuppression may occur rather than desired immunoactivation, resulting in exacerbation of the disease. In addition, patients suffering from infectious diseases may have higher ADCC and/or CDC activities. Therefore, when such antibodies are applied to infectious diseases, it is necessary to evaluate them for safety more carefully, for example, using more active rabbit complements than those present in healthy human serum or peripheral blood which could not be effective to detect the above activities in this situation. Accordingly, mutants and recombinants were created which had no activity of ADCC or CDC and examined for their activity.

Since ADCC and/or CDC activities are known to vary depending on a subclass of the antibody of interest, conversion of the subclass may reduce ADCC and/or CDC activities. For the human IgG subclasses, for example, IgG4 is generally known to be a subclass with low activities of both ADCC and CDC, and it is reported that IgG2 is CDC active but poorly active in ADCC, while IgG1 is highly active in both ADCC and CDC (Charles A. Janeway et al., Immunology, 1997, Current Biology Ltd./Garland Publishing Inc.). Selection of a particular subclass by taking advantage of the above characteristics may create a less cytotoxic antibody from the original antibody. A combination of a specific subclass of antibody with such a point mutation as described below may create an antibody with a desired activity. Further, reduction in ADCC and/or CDC activities of an antibody is reported to be attained by incorporation of a mutation into its constant region. For instance, L235, D265, D270, K322, P331, and P329 (each alphabetical letter denotes an amino acid by the single-letter notation, and each number denotes an EU index proposed by Kabat et al. (Kabat et. al., Sequences of proteins of Immunological Interest, 1991 Fifth edition); such symbols will be used hereinafter.) may play an important role in complement activation by human IgG, and substitution of one of those sites by another amino acid may reduce the CDC activity. Esohe E. Idusogie et. al. J. Immunol. 2000, 164:4178-4184, Yuanyuan Xu et. al. J. Biol. Chem. 1994, 269:3469-3474, Brekke, O. H. et. al. Eur. J. Immunol. 1994, 24:2542, Morgan, A., et. al., Immunology 1995, 86:319, Lund, J., et. al:, J. Immunol., 1996, 157:4963, Tao, M. H., et. al., J. Exp. Med. 1993, 178:661). Specifically, substitution of D270, K322, P329, or P331 by A may reduce the CDC activity. Substitution of P331 by S or G may also induce the same thing.

It is believed that Glu233-Ser239, Gly316-Lys338, Lys274-Arg301, Tyr407-Arg416, Asn297, Glu318, Leu234-Ser239, Asp265-Glu269, Asn297-Thr299 and Ala327-Ile332 take part in binding of IgG to FcR (Duncan, A. R., Woof, J. M., Partridge, L. J., Burton, D. R., and Winter, G. (1988) Nature 332, 563-564, Gessner, J. E., Heiken, H., Tamm, A., and Schmidt, R. E. (1998) Ann. Hematol. 76, 231-248, Gavin, A., Hulett, M, and Hogarth, P. M. (1998) in The Immunoglobulin Receptors and Their Physiological and Pathological Roles in Immunity (van de Winkel, J. G. J. ,and Hogarth, P. M., eds), pp. 11-35, Kluwer Academic Publishers Group, Dordrecht, The Netherlands, Sautes, C. (1997) in Cell-mediated Effects of Immunoglobulins (Fridman, W. H., and Sautes, C., eds), pp. 29-66, R. G. Landes Co., Austin, Tex., Da'ron, M. (1997) Annu. Rev. Immunol. 15, 203-234, Canfield, S. M., and Morrison, S. L. (1991) J. Exp. Med. 173, 1483-1491, Chappel, M. S., Isenman, D. E., Everett, M., Xu, Y.-Y., Dorrington, K. J., and Klein, M. H. (1991) Proc. Natl. Acad. Sci. U.S.A. 88, 9036-9040, Woof, J. M., Partridge, L. J., Jefferis, R., and Burton, D. R. (1986) Mol. Immunol. 23, 319-330, Wines, B. D., Powell, M. S., Parren, P. W. H. I., Barnes, N., and Hogarth, P. M. (2000) J. Imunol. 164, 5313-5318), and thus incorporation of a mutation into one of these regions may reduce the ADCC activity. Specifically, substitution of L235 by E or G237 by A can reduce binding of IgG to FcR.

The antibody according to the present invention has at least one mutation of amino acids to reduce the ADCC and/or CDC activities, preferably 1-20, 1-17, 1-16, 1-15, 1-14, 1-13, 1-12, 1-11, 1-10, 1-9, 1-8, 1-7, 1-6, 1-5, 14, 1-3, or 1 or 2 mutations.

The present invention has revealed that in some anti-CD40 antibodies, the hinge region of IgG2 is important in expression of their strong agonistic activities. Replacement of the variable region or the constant region except the hinge region by a counterpart of any different subclass, or incorporation of a point mutation thereinto is expected to not only modulate the ADCC and/or CDC activities, but increase the productivity of the antibody, its stability during purification and storage, and its blood kinetics.

To produce an antibody drug, the stability of the antibody during purification and storage is very important. Since the antibodies so far developed belong mainly to the IgG1 subclass, conversion of the variable region or the constant region except the hinge region to a sequence derived from the IgG1 subclass will be also effective to improve the physical properties of the anti-CD40 agonistic antibodies described above.

The present invention provides mutants of agonistic anti-CD40 antibodies and others as follows:

[1] A heavy chain of a monoclonal antibody having an agonistic activity, which binds to CD40, wherein the heavy chain comprises an upper hinge and a middle hinge derived from a human IgG2, and a constant region with at least one amino acid deleted or substituted, or with at least one amino acid added thereto, said deletion, substitution or addition being capable of increasing or decreasing ADCC and/or CDC.

[2] The heavy chain according to [1], wherein the constant region is derived from a human IgG.

[3] The heavy chain according to [2], wherein the human IgG is a human IgG1.

[4] The heavy chain according to [2], wherein the human IgG is a human IgG2.

[5] The heavy chain according to [2], wherein the human IgG is a human IgG3.

[6] The heavy chain according to [2], wherein the human IgG is a human IgG4.

[7] The heavy chain according to any of [3] to [5], wherein said substitution of amino acids in the constant region is substitution of proline with serine at position 331 which is indicated by the EU index as in Kabat et al.

[8] A monoclonal antibody comprising the heavy chain according to any of [1] to [7].

[9] The heavy chain according to any of [1] to [7], wherein the heavy chain comprises a variable region from a heavy chain of a monoclonal antibody produced by the hybridoma KM341-1-19 (Accession No. FERM BP-7759).

[10] A monoclonal antibody consisting of the heavy chain according to [9] and a light chain comprising a variable region from a light chain of a monoclonal antibody produced by the hybridoma KM341-1-19 (Accession No. FERM BP-7759).

[11] The heavy chain according to any of [1] to [7], wherein the heavy chain comprises a variable region of the polypeptide represented by SEQ ID NO: 38.

[12] A monoclonal antibody consisting of the heavy chain according to [11] and a light chain of a monoclonal antibody, wherein the light chain comprises a variable region of the polypeptide represented by SEQ ID NO: 40.

[13] The heavy chain according to [1], wherein the heavy chain consists of a remaining portion provided by removing the signal sequence from the polypeptide represented by SEQ IDNO: 132.

[14] A monoclonal antibody consisting of the heavy chain according to [13] and a light chain of a monoclonal antibody, wherein the light chain consists of a remaining portion provided by removing the signal sequence from the polypeptide represented by SEQ ID NO: 134.

[15] The heavy chain according to [1], wherein the heavy chain is produced by a host comprising an expression vector having the polynucleotide represented by SEQ ID NO: 131.

[16] The monoclonal antibody according to [8], wherein the monoclonal antibody is produced by a host comprising an expression vector having the polynucleotide represented by SEQ ID NO: 131 and the polynucleotide represented by SEQ ID NO: 133.

[17] The heavy chain according to any of [1] to [7], wherein the heavy chain comprises a variable region from a heavy chain of a monoclonal antibody produced by the hybridoma 2105 (Accession No. FERM BP-8024).

[18] A monoclonal antibody consisting of the heavy chain according to [17] and a light chain comprising a variable region from a light chain of a monoclonal antibody produced by the hybridoma 2105 (Accession No. FERM BP-8024).

[19] The heavy chain according to any of [1] to [7], wherein the heavy chain comprises a variable region of the polypeptide represented by SEQ ID NO: 42.

[20] A monoclonal antibody consisting of the heavy chain according to [19] and a light chain of a monoclonal antibody, wherein the light chain comprises a variable region of the polypeptide represented by SEQ ID NO: 44.

[21] The heavy chain according to [1], wherein the heavy chain consists of a remaining portion provided by removing the signal sequence from the polypeptide represented by SEQ ID NO: 136.

[22] A monoclonal antibody consisting of the heavy chain according to [21] and a light chain of a monoclonal antibody, wherein the light chain consists of a remaining portion provided by removing the signal sequence from the polypeptide represented by SEQ ID NO: 138.

[23] The heavy chain according to [1], wherein the heavy chain is produced by a host comprising an expression vector having the polynucleotide represented by SEQ ID NO: 135.

[24] The monoclonal antibody according to [8], wherein the monoclonal antibody is produced by a host comprising an expression vector having the polynucleotide represented by SEQ ID NO: 135 and the polynucleotide represented by SEQ ID NO: 137.

[25] A polynucleotide represented by SEQ ID NO: 131.

[26] A polynucleotide represented by SEQ ID NO: 133.

[27] An expression vector having the polynucleotide according to [25].

[28] An expression vector having the polynucleotide according to [26].

[29] An expression vector having the polynucleotides according to [25] and [26].

[30] A host comprising the expression vector according to [27].

[31] A host comprising the expression vector according to [28].

[32] A host comprising the expression vector according to [29].

[33] A process of producing a heavy chain of a monoclonal antibody, comprising the steps of: culturing the host according to [30] in a culture medium; and obtaining a heavy chain of a monoclonal antibody from the culture and/or the host.

[34] A process of producing a monoclonal antibody, comprising the steps of: culturing the host according to [32] in a culture medium; and obtaining a monoclonal antibody from the culture and/or the host.

[35] A polynucleotide represented by SEQ ID NO: 135.

[36] A polynucleotide represented by SEQ ID NO: 137.

[37] An expression vector having the polynucleotide according to [35].

[38] An expression vector having the polynucleotide according to [36].

[39] An expression vector having the polynucleotides according to [35] and [36].

[40] A host comprising the expression vector according to [37].

[41] A host comprising the expression vector according to [38].

[42] A host comprising the expression vector according to [39].

[43] A process of producing a heavy chain of a monoclonal antibody, comprising the steps of: culturing the host according to [40] in a culture medium; and obtaining a heavy chain of a monoclonal antibody from the culture and/or the host.

[44] A process of producing a a monoclonal antibody, comprising the steps of: culturing the host according to [42] in a culture medium; and obtaining a monoclonal antibody from the culture and/or the host.

[45] A process of producing a heavy chain of a monoclonal antibody having an agonistic activity capable of binding to CD40, comprising the step of substituting the upper hinge and the middle hinge of an antibody, which is not either an upper hinge or a middle hinge derived from a human IgG2, with an upper hinge and a middle hinge derived from a human IgG2, respectively.

[46] A process of producing a heavy chain of a monoclonal antibody comprising a variable region, and an upper hinge and a middle hinge derived from a human IgG2, comprising the step of identifying a polypeptide forming the variable region, which is from a heavy chain of a monoclonal antibody capable of binding to CD40.

[47] A process of producing a monoclonal antibody having an agonistic activity capable of binding to CD40, comprising the step of substituting the upper hinge and the middle hinge of an antibody, which is not either an upper hinge or a middle hinge derived from a human IgG2, with an upper hinge and a middle hinge derived from a human IgG2, respectively.

[48] A process of producing a monoclonal antibody comprising a variable region, and an upper hinge and a middle hinge derived from a human IgG2, comprising the step of identifying a polypeptide forming the variable region, which is from a heavy chain of a monoclonal antibody capable of binding to CD40.

[49] A pharmaceutical composition comprising the monoclonal antibody according to [8], [10], [12], [14], [16], [18], [20], [22] or [24] as an active ingredient.

[50] The pharmaceutical composition according to [49] used for prevention or treatment of a malignant tumor, a pathogen or an autoimmune disease.

[51] A method of prevention or treatment of a malignant tumor, a pathogen or an autoimmune disease, comprising administration of the pharmaceutical composition according to [49] into a mammal.

[52] Use of the monoclonal antibody according to [8], [10], [12], [14], [16], [18], [20], [22] or [24] for production of a pharmaceutical composition used for prevention or treatment of a malignant tumor, a pathogen or an autoimmune disease.

[89] A polynucleotide provided by removing the portion encoding the signal sequence from the polynucleotide represented by SEQ ID NO: 131.

[90] A polynucleotide provided by removing the portion encoding the signal sequence from the polynucleotide represented by SEQ ID NO: 133.

[91] A polynucleotide provided by removing the portion encoding the signal sequence from the polynucleotide represented by SEQ ID NO: 135.

[92] A polynucleotide provided by removing the portion encoding the signal sequence from the polynucleotide represented by SEQ ID NO: 137.

The present invention provides an antibody produced by modification of an agonistic anti-CD40 antibody belonging to the human IgG2, wherein the modified antibody is a mutant having the constant region, exclusive of the upper and middle hinges, substituted with a sequence derived from a different subclass. The subclass is preferably IgG1. The present invention provides an antibody produced by modification of an agonistic anti-CD40 antibody belonging to the human IgG2, wherein the modified antibody is a mutant having the constant region, exclusive of the hinge region, substituted with a sequence derived from a different subclass. The subclass is preferably IgG1.

Herein, reduction in ADCC and CDC activities means reduction in those activities as compared with the corresponding activities of an anti-CD40 monoclonal antibody other than the mutants described above, for example, as compared with the corresponding activities of a monoclonal antibody produced by the hybridoma KM341-1-19 (Accession No. FERM BP-7759) or 2105 (Accession No. FERM BP-8024). The ADCC and CDC activities may be assayed by any known method, for example, the method described in the Examples herein. The sequences of variable regions in the heavy and light chains of a monoclonal antibody will be presented below which is produced by the hybridoma KM341-1-19 (Accession No. FERM BP-7759) or 2105 (Accession No. FERM BP-8024).

DNA encoding variable regions in the heavy and light chains of the KM341-1-19 antibody and the amino acid sequences of the heavy and light chains will be presented below.

In the heavy chain nucleotide sequence (SEQ ID NO: 37) of the KM341-1-19 antibody, the signal sequence is initiated with adenine (A) at position 50. The boundary between the signal sequence and the variable region is located between "adenine" ([A]) at position 109 and cytosine (C) at position 110, and the boundary between the variable region and the constant region is located between adenine (A) at position 493 and guanine (G) at position 494 (the gene prediction software (Signal P ver.2) was used).

In the heavy chain amino acid sequence (SEQ ID NO: 38) of the KM341-1-19 antibody, the boundary between the signal sequence and the variable region is located between serine (S) at position 20 and glutamine (Q) at position 21, and the boundary between the variable region and the constant region is located between serine (S) at position 148 and alanine (A) at position 149.

Accordingly, the variable region in the heavy chain of the KM341-1-19 antibody has a nucleotide sequence ranging from cytosine (C) at position 110 to adenine (A) at position 493, as seen in SEQ ID NO: 37. Further, the variable region in the heavy chain of the KM341-1-19 antibody has an amino acid sequence ranging from glutamine (Q) at position 21 to serine (S) at position 148, as seen in SEQ ID NO: 38.

In the light chain nucleotide sequence (SEQ ID NO: 39) of the KM341-1-19 antibody, the signal sequence is initiated with adenine (A) at position 29. The boundary between the signal sequence and the variable region is located between "adenine" ([A]) at position 88 and guanine (G) at position 89, and the boundary between the variable region and the constant region is located between adenine (A) at position 400 and "cytosine" ([C]) at position 401 (the gene prediction software (Signal P ver.2) was used).

In the light chain amino acid sequence (SEQ ID NO: 40) of the KM341-1-19 antibody, the boundary between the signal sequence and the variable region is located between glycine (G) at position 20 and glutamic acid (E) at position 21, and the boundary between the variable region and the constant region is located between lysine (K) at position 124 and "arginine" ([R]) at position 125.

Accordingly, the variable region in the light chain of the KM341-1-19 antibody has a nucleotide sequence ranging from guanine (G) at position 89 to adenine (A) at position 400, as seen in SEQ ID NO: 39. Further, the variable region in the light chain of the KM341-1-19 antibody has an amino acid sequence ranging from glutamic acid (E) at position 21 to lysine (K) at position 124, as seen in SEQ ID NO: 40.

The heavy chain nucleotide sequence (SEQ ID NO: 37) of the KM341-1-19 antibody:

```
GTCGACGCTGAATTCTGGCTGACCAGGGCAGCCACCAGAGCTCCAGACAA
TGTCTGTCTCCTTCCTCATCTTCCTGCCCGTGCTGGGCCTCCCATGGGGT
GTCCTGTCACAGGTCCAACTGCAGCAGTCAGGTCCAGGACTGGTGAAGCC
CTCGCAGACCCTCTCACTCACCTGTGCCATCTCCGGGGACAGTGTCTCTA
GCAACAGTGCTACTTGGAACTGGATCAGGCAGTCCCCATCGAGAGACCTT
GAGTGGCTGGGAAGGACATACTACAGGTCCAAGTGGTATCGTGATTATGT
AGGATCTGTGAAAAGTCGAATAATCATCAACCCAGACACATCCAACAACC
AGTTCTCCCTGCAGCTGAACTCTGTGACTCCCGAGGACACGGCTATATAT
TACTGTACAAGAGCACAGTGGCTGGGAGGGGATTACCCCTACTACTACAG
TATGGACGTCTGGGGCCAAGGGACCACGGTCACCGTCTCTTCAGCCTCCA
CCAAGGGCCCATCGGTCTTCCCCCTGGCGCCCTGCTCCAGGAGCACCTCC
GAGAGCACAGCGGCCCTGGGCTGCCTGGTCAAGGACTACTTCCCCGAACC
GGTGACGGTGTCGTGGAACTCAGGCGCTCTGACCAGCGGCGTGCACACCT
TCCCAGCTGTCCTACAGTCCTCAGGACTCTACTCCCTCAGGAGCGTGGTG
ACCGTGCCCTCCAGCAACTTCGGCACCCAGACCTACACCTGCAACGTAGA
TCACAAGCCCAGCAACACCAAGGTGGACAAGACAGTTGAGCGCAAATGTT
GTGTCGAGTGCCCACCGTGCCCAGCACCACCTGTGGCAGGACCGTCAGTC
TTCCTCTTCCCCCCAAAACCCAAGGACACCCTCATGATCTCCCGGACCCC
TGAGGTCACGTGCGTGGTGGTGGACGTGAGCCACGAAGACCCCGAGGTCC
AGTTCAACTGGTACGTGGACGGCGTGGAGGTGCATAATGCCAAGACAAAG
CCACGGGAGGAGCAGTTCAACAGCAGGTTCCGTGTGGTCAGCGTCCTCAC
CGTTGTGCACCAGGACTGGCTGAACGGCAAGGAGTACAAGTGCAAGGTCT
CCAACAAAGGCCTCCCAGCCCCCATCGAGAAAACCATCTCCAAAACCAAA
```

```
GGGCAGCCCCGAGAACCACAGGTGTACACCCTGCCCCCATCCCGGGAGGA

GATGACCAAGAACCAGGTCAGCCTGACCTGCCTGGTCAAAGGCTTCTACC

CCAGCGACATCGCCGTGGAGTGGGAGAGCAATGGGCAGCCGGAGAACAAC

TACAAGACCACACCTCCCATGCTGGACTCAGACGGCTCCTTCTTCCTCTA

CAGCAAGCTCACCGTGGACAAGAGCAGGTGGCAGCAGGGGAACGTCTTCT

CATGCTCCGTGATGCATGAGGCTCTGCACAACCACTACACGCAGAAGAGC

CTCTCCCTGTCTCCGGGTAAATGAGGATCC
```

The heavy chain amino acid sequence (SEQ ID NO: 38) of the KM341-1-19 antibody:

```
MSVSFLIFLPVLGLPWGVLSQVQLQQSGPGLVKPSQTLSLTCAISGDSVS

SNSATWNWIRQSPSRDLEWLGRTYYRSKWYRDYVGSVKSRIIINPDTSNN

QFSLQLNSVTPEDTAIYYCTRAQWLGGDYPYYYSMDVWGQGTTVTVSSAS

TKGPSVFPLAPCSRSTSESTAALGCLVKDYFPEPVTVSWNSGALTSGVHT

FPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEV

QFNWYVDGVEVHNAKTKPREEQFNSTFRVVSVLTVVHQDWLNGKEYKCKV

SNKGLPAPIEKTISKTKGQPREPQVYTLPPSREEMTKNQVSLTCLVKGFY

PSDIAVEWESNGQPENNYKTTPPMLDSDGSFFLYSKLTVDKSRWQQGNVF

SCSVMHEALHNHYTQKSLSLSPGK
```

The light chain nucleotide sequence (SEQ ID NO: 39) of the KM341-1-19 antibody:

```
ACTGCTCAGTTAGGACCCAGAGGGAACCATGGAAGCCCCAGCTCAGCTTC

TCTTCCTCCTGCTACTCTGGCTCCCAGATACCACCGGAGAAATTGTGTTG

ACACAGTCTCCAGCCACCCTGTCTTTGTCTCCAGGGGAAAGAGCCACCCT

CTCCTGCAGGGCCAGTCAGAGTGTTAGCAGCTACTTAGCCTGGTACCAAC

AGAAACCTGGCCAGGCTCCCAGGCTCCTCATCTATGATGCATCCAACAGG

GCCACTGGCATCCCAGCCAGGTTCAGTGGCAGTGGGTCTGGGACAGACTT

CACTCTCACCATCAGCAGCCTAGAGCCTGAAGATTTTGCAGTTTATTACT

GTCAGCAGCGTAGCAACACTTTCGGCCCTGGGACCAAAGTGGATATCAAA

CGTACG
```

The light chain amino acid sequence (SEQ ID NO: 40) of the KM341-1-19 antibody:

```
MEAPAQLLFLLLLWLPDTTGEIVLTQSPATLSLSPGERATLSCRASQSVS

SYLAWYQQKPGQAPRLLIYDASNRATGIPARFSGSGSGTDFTLTISSLEP

EDFAVYYCQQRSNTFGPGTKVDIKRT
```

DNA encoding variable regions in the heavy and light chains of the 2105 antibody and the amino acid sequences of the heavy and light chains will be presented below.

In the heavy chain nucleotide sequence (SEQ ID NO: 41) of the 2105 antibody, the signal sequence is initiated with adenine (A) at position 70. The boundary between the signal sequence and the variable region is located between "thymine" ([T]) at position 126 and guanine (G) at position 127, and the boundary between the variable region and the constant region is located between adenine (A) at position 495 and guanine (G) at position 496 (the gene prediction software (Signal P ver.2) was used).

In the heavy chain amino acid sequence (SEQ ID NO: 42) of the 2105 antibody, the boundary between the signal sequence and the variable region is located between cysteine (C) at position 19 and glutamic acid (E) at position 20, and the boundary between the variable region and the constant region is located between serine (S) at position 142 and alanine (A) at position 143.

Accordingly, the variable region in the heavy chain of the 2105 antibody has a nucleotide sequence ranging from guanine (G) at position 127 to adenine (A) at position 495, as seen in SEQ ID NO: 41. Further, the variable region in the heavy chain of the 2105 antibody has an amino acid sequence ranging from glutamic acid (E) at position 20 to. serine (S) at position 142, as seen in SEQ ID NO: 42.

In the light chain nucleotide sequence (SEQ ID NO: 43) of the 2105 antibody, the signal sequence is initiated with adenine (A) at position 28. The boundary between the signal sequence and the variable region is located between "adenine" ([A]) at position 87 and guanine (G) at position 88, and the boundary between the variable region and the constant region is located between adenine (A) at position 405 and "cytosine" ([C]) at position 406 (the gene prediction software (Signal P ver.2) was used).

In the light chain amino acid sequence (SEQ ID NO: 44) of the 2105 antibody, the boundary between the signal sequence and the variable region is located between glycine (G) at position 20 and glutamic acid (E) at position 21, and the boundary between the variable region and the constant region is located between lysine (K) at position 126 and "arginine" ([R]) at position 127.

Accordingly, the variable region in the light chain of the 2105 antibody has a nucleotide sequence ranging from guanine (G) at position 88 to adenine (A) at position 405, as seen in SEQ ID NO: 43. Further, the variable region in the light chain of the 2105 antibody has an amino acid sequence ranging from glutamic acid (E) at position 21 to lysine (K) at position 126, as seen in SEQ ID NO: 44.

The heavy chain nucleotide sequence (SEQ ID NO: 41) of the 2105 antibody:

```
CTGAACACAGACCCGTCGACTCCCAGGTGTTTCCATTCAGTGATCAGCAC

TGAACACAGAGGACTCACCATGGAGTTGGGACTGAGCTGGATTTTCCTTT

TGGCTATTTTAAAAGGTGTCCAGTGTGAAGTGCAGCTGGTGGAGTCTGGG

GGAGGCTTGGTACAGCCTGGCAGGTCCCTGAGACTCTCCTGTGCAGCCTC

TGGATTCACCTTTGATGATTATGCCATGCACTGGGTCCGGCAAGCTCCAG

GGAAGGGCCTGGAGTGGGTCTCAGGTATTAGTTGGAATAGTGGTAGCTTG

GTGCATGCGGACTCTGTGAAGGGCCGATTCACCATCTCCAGAGACAACGC

CAAGAACTCCCTGTATCTGCAAATGAACAGTCTGAGAGCTGAGGACACGG

CCTTGTATTACTGTGCAAGAGATAGGCTATTTCGGGGAGTTAGGTACTAC

GGTATGGACGTCTGGGGCCAAGGGACCACGGTCACCGTCTCCTCAGCTAG

CACCAAGG
```

The heavy chain amino acid sequence (SEQ ID NO: 42) of the 2105 antibody:

MELGLSWIFLLAILKGVQCEVQLVESGGGLVQPGRSLRLSCAASGFTFDD
YAMHWVRQAPGKGLEWVSGISWNSGSLVHADSVKGRFTISRDNAKNSLYL
QMNSLRAEDTALYYCARDRLFRGVRYYGMDVWGQGTTVTVSSASTK

The light chain nucleotide sequence (SEQ ID NO: 43) of the 2105 antibody:

CTGCTCAGTTAGGACCCAGAGGGAACCATGGAAGCCCCAGCTCAGCTTCT
CTTCCTCCTGCTACTCTGGCTCCCAGATACCACCGGAGAAATTGTGTTGA
CACAGTCTCCAGCCACCCTGTCTTTGTCTCCAGGGGAAAGAGCCACCCTC
TCCTGCAGGGCCAGTCAGAGTGTTAGCAGCTACTTAGCCTGGTACCAACA
GAAACCTGGCCAGGCTCCCAGGCTCCTCATCTATGATGCATCCAACAGGG
CCACTGGCATCCCAGCCAGGTTCAGTGGCAGTGGGTCTGGGACAGACTTC
ACTCTCACCATCAGCAGCCTAGAGCCTGAAGATTTTGCAGTTTATTACTG
TCAGCAGCGTAGCCACTGGCTCACTTTCGGCGGGGGGACCAAGGTGGAGA
TCAAACGTACGGTG

The light chain amino acid sequence (SEQ ID NO: 44) of the 2105 antibody:

MEAPAQLLFLLLLWLPDTTGEIVLTQSPATLSLSPGERATLSCRASQSVS
SYLAWYQQKPGQAPRLLIYDASNRATGIPARFSGSGSGTDFTLTISSLEP
EDFAVYYCQQRSHWLTFGGGTKVEIKRTV

In the heavy chain nucleotide sequence (SEQ ID NO: 131) of the 341G2Ser, the boundary between the signal sequence and the variable region is located between "adenine" ([A]) at position 60 and cytosine (C) at position 61, and the boundary between the variable region and the constant region is located between adenine (A) at position 444 and guanine (G) at position 445 (the gene prediction software (Signal P ver.2) was used).

In the heavy chain amino acid sequence (SEQ ID NO: 132) of the 341G2Ser, the boundary between the signal sequence and the variable region is located between serine (S) at position 20 and glutamine (Q) at position 21, and the boundary between the variable region and the constant region is located between serine (S) at position 148 and alanine (A) at position 149.

Accordingly, the variable region in the heavy chain of the 341G2Ser has a nucleotide sequence ranging from cytosine (C) at position 61 to adenine (A) at position 444, as seen in SEQ ID NO: 131. Further, the variable region in the heavy chain of the 341G2Ser has an amino acid sequence ranging from glutamine (Q) at position 21 to serine (S) at position 148, as seen in SEQ ID NO: 132.

The entire heavy chain nucleotide sequence of the 341G2Ser (SEQ ID NO: 131):

ATGTCTGTCTCCTTCCTCATCTTCCTGCCCGTGCTGGGCCTCCCATGGGG
TGTCCTGTCACAGGTCCAACTGCAGCAGTCAGGTCCAGGACTGGTGAAGC
CCTCGCAGACCCTCTCACTCACCTGTGCCATCTCCGGGGACAGTGTCTCT
AGCAACAGTGCTACTTGGAACTGGATCAGGCAGTCCCCATCGAGAGACCT
TGAGTGGCTGGGAAGGACATACTACAGGTCCAAGTGGTATCGTGATTATG
TAGGATCTGTGAAAAGTCGAATAATCATCAACCCAGACACATCCAACAAC
CAGTTCTCCCTGCAGCTGAACTCTGTGACTCCCGAGGACACGGCTATATA
TTACTGTACAAGAGCACAGTGGCTGGGAGGGGATTACCCCTACTACTACA
GTATGGACGTCTGGGGCCAAGGGACCACGGTCACCGTCTCCTCAGCTAGC
ACCAAGGGCCCATCGGTCTTCCCCCTGGCGCCCTGCTCCAGGAGCACCTC
CGAGAGCACAGCGGCCCTGGGCTGCCTGGTCAAGGACTACTTCCCCGAAC
CGGTGACGGTGTCGTGGAACTCAGGCGCTCTGACCAGCGGCGTGCACACC
TTCCCAGCTGTCCTACAGTCCTCAGGACTCTACTCCCTCAGCAGCGTGGT
GACCGTGCCCTCCAGCAACTTCGGCACCCAGACCTACACCTGCAACGTAG
ATCACAAGCCCAGCAACACCAAGGTGGACAAGACAGTTGAGCGCAAATGT
TGTGTCGAGTGCCCACCGTGCCCAGCACCACCTGTGGCAGGACCGTCAGT
CTTCCTCTTCCCCCCAAAACCCAAGGACACCCTCATGATCTCCCGGACCC
CTGAGGTCACGTGCGTGGTGGTGGACGTGAGCCACGAAGACCCCGAGGTC
CAGTTCAACTGGTACGTGGACGGCGTGGAGGTGCATAATGCCAAGACAAA
GCCACGGGAGGAGCAGTTCAACAGCACGTTCCGTGTGGTCAGCGTCCTCA
CCGTTGTGCACCAGGACTGGCTGAACGGCAAGGAGTACAAGTGCAAGGTC
TCCAACAAAGGCCTCCCAGCCTCCATCGAGAAAACCATCTCCAAAACCAA
AGGGCAGCCCCGAGAACCACAGGTGTACACCCTGCCCCCATCCCGGGAGG
AGATGACCAAGAACCAGGTCAGCCTGACCTGCCTGGTCAAAGGCTTCTAC
CCCAGCGACATCGCCGTGGAGTGGGAGAGCAATGGGCAGCCGGAGAACAA
CTACAAGACCACACCTCCCATGCTGGACTCCGACGGCTCCTTCTTCCTCT
ACAGCAAGCTCACCGTGGACAAGAGCAGGTGGCAGCAGGGGAACGTCTTC
TCATGCTCCGTGATGCATGAGGCTCTGCACAACCACTACACGCAGAAGAG
CCTCTCCCTGTCTCCGGGTAAATGA

The entire heavy chain amino acid sequence of the 341G2Ser (SEQ ID NO: 132):

MSVSFLIFLPVLGLPWGVLSQVQLQQSGPGLVKPSQTLSLTCAISGDSVS
SNSATWNWIRQSPSRDLEWLGRTYYRSKWYRDYVGSVKSRIIINPDTSNN
QFSLQLNSVTPEDTAIYYCTRAQWLGGDYPYYYSMDVWGQGTTVTVSSAS
TKGPSVFPLAPCSRSTSESTAALGCLVKDYFPEPVTVSWNSGALTSGVHT
FPAVLQSSGLYSLSSVVTVPSSNFGTQTYTCNVDHKPSNTKVDKTVERKC
CVECPPCPAPPVAGPSVFLFPPKPKDTLMISRTPEVTCVVVDVSHEDPEV
QFNWYVDGVEVHNAKTKPREEQFNSTFRVVSVLTVVHQDWLNGKEYKCKV
SNKGLPASIEKTISKTKGQPREPQVYTLPPSREEMTKNQVSLTCLVKGFY
PSDIAVEWESNGQPENNYKTTPPMLDSDGSFFLYSKLTVDKSRWQQGNVF
SCSVMHEALHNHYTQKSLSLSPGK

In the light chain nucleotide sequence (SEQ ID NO: 133) of the 341G2Ser, the boundary between the signal sequence and the variable region is located between "adenine" ([A]) at position 60 and guanine (G) at position 61, and the boundary between the variable region and the constant region is located between adenine (A) at position 372 and "cytosine" ([C]) at position 373 (the gene prediction software (Signal P ver.2) was used).

In the light chain amino acid sequence (SEQ ID NO: 134) of the 341G2Ser, the boundary between the signal sequence and the variable region is located between glycine (G) at position 20 and glutamic acid (E) at position 21, and the boundary between the variable region and the constant region is located between lysine (K) at position 124 and "arginine" ([R]) at position 125. Accordingly, the variable region in the light chain of the 341G2Ser has a nucleotide sequence ranging from guanine (G) at position 61 to adenine (A) at position 372, as seen in SEQ ID NO: 133. Further, the variable region in the light chain of the 341G2Ser has an amino acid sequence ranging from glutamic acid (E) at position 21 to lysine (K) at position 124, as seen in SEQ ID NO: 134.

The entire light chain nucleotide sequence of the 341G2Ser (SEQ ID NO: 133):

ATGGAAGCCCCAGCTCAGCTTCTCTTCCTCCTGCTACTCTGGCTCCCAGA

TACCACCGGAGAAATTGTGTTGACACAGTCTCCAGCCACCCTGTCTTTGT

CTCCAGGGGAAAGAGCCACCCTCTCCTGCAGGGCCAGTCAGAGTGTTAGC

AGCTACTTAGCCTGGTACCAACAGAAACCTGGCCAGGCTCCCAGGCTCCT

CATCTATGATGCATCCAACAGGGCCACTGGCATCCCAGCCAGGTTCAGTG

GCAGTGGGTCTGGGACAGACTTCACTCTCACCATCAGCAGCCTAGAGCCT

GAAGATTTTGCAGTTTATTACTGTCAGCAGCGTAGCAACACTTTCGGCCC

TGGGACCAAAGTGGATATCAAACGTACGGTGGCTGCACCATCTGTCTTCA

TCTTCCCGCCATCTGATGAGCAGTTGAAATCTGGAACTGCCTCTGTTGTG

TGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGG

ACAGCAAGGACAGCACCTACAGCCTCAGCAGCACCCTGACGCTGAGCAAA

GCAGACTACGAGAAACACAAAGTCTACGCCTGCGAAGTCACCCATCAGGG

CCTGAGCTCGCCCGTCACAAAGAGCTTCAACAGGGGAGAGTGTTGA

The entire light chain amino acid sequence of the 341G2Ser (SEQ ID NO: 134):

MEAPAQLLFLLLLWLPDTTGEIVLTQSPATLSLSPGERATLSCRASQSVS

SYLAWYQQKPGQAPRLLIYDASNRATGIPARFSGSGSGTDFTLTISSLEP

EDFAVYYCQQRSNTFGPGTKVDIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC

In the heavy chain nucleotide sequence (SEQ ID NO: 135) of the 2105G2Ser, the boundary between the signal sequence and the variable region is located between "thymine" ([T]) at position 57 and guanine (G) at position 58, and the boundary between the variable region and the constant region is located between adenine (A) at position 426 and guanine (G) at position 427 (the gene prediction software (Signal P ver.2) was used).

In the heavy chain amino acid sequence (SEQ ID NO: 136) of the 2105G2Ser, the boundary between the signal sequence and the variable region is located between cysteine (C) at position 19 and glutamic acid (E) at position 20, and the boundary between the variable region and the constant region is located between serine (S) at position 142 and alanine (A) at position 143.

Accordingly, the variable region in the heavy chain of the 2105G2Ser has a nucleotide sequence ranging from guanine (G) at position 58 to adenine (A) at position 426, as seen in SEQ ID NO: 135. Further, the variable region in the heavy chain of the 2105G2Ser has an amino acid sequence ranging from glutamic acid (E) at position 20 to serine (S) at position 142, as seen in SEQ ID NO: 136.

The entire heavy chain nucleotide sequence of the 2105G2Ser (SEQ ID NO: 135):

ATGGAGTTGGGACTGAGCTGGATTTTCCTTTTGGCTATTTTAAAAGGTGT

CCAGTGTGAAGTGCAGCTGGTGGAGTCTGGGGGAGGCTTGGTACAGCCTG

GCAGGTCCCTGAGACTCTCGTGTGCAGCCTCTGGATTCACCTTTGATGAT

TATGCCATGCACTGGGTCCGGCAAGCTCCAGGGAAGGGCCTGGAGTGGGT

CTCAGGTATTAGTGGAATAGTGGTAGCTTGGTGCATGCGGACTCTGTGA

AGGGCCGATTCACCATCTCCAGAGACAACGCCAAGAACTCCCTGTATCTG

CAAATGAACAGTCTGAGAGCTGAGGACACGGCCTTGTATTACTGTGCAAG

AGATAGGCTATTTCGGGGAGTTAGGTACTACGGTATGGACGTCTGGGGCC

AAGGGACCACGGTCACCGTCTCCTCAGCTAGCACCAAGGGCCCATCGGTC

TTCCCCCTGGCGCCCTGCTCCAGGAGCACCTCCGAGAGCACAGCGGCCCT

GGGCTGCCTGGTCAAGGACTACTTCCCCGAACCGGTGACGGTGTCGTGGA

ACTCAGGCGCTCTGACCAGCGGCGTGCACACCTTCCCAGCTGTCCTACAG

TCCTCAGGACTCTACTCCCTCAGCAGCGTGGTGACCGTGCCCTCCAGCAA

CTTCGGCACCCAGACCTACACCTGCAACGTAGATCACAAGCCCAGCAACA

CCAAGGTGGACAAGACAGTTGAGCGCAAATGTTGTGTCGAGTGCCCACCG

TGCCCAGCACCACCTGTGGCAGGACCGTCAGTCTTCCTCTTCCCCCCAAA

ACCCAAGGACACCCTCATGATCTCCCGGACCCCTGAGGTCACGTGCGTGG

TGGTGGACGTGAGCCACGAAGACCCCGAGGTCCAGTTCAACTGGTACGTG

GACGGCGTGGAGGTGCATAATGCCAAGACAAAGCCACGGGAGGAGCAGTT

CAACAGCACGTTCCGTGTGGTCAGCGTCCTCACCGTTGTGCACCAGGACT

GGCTGAACGGCAAGGAGTACAAGTGCAAGGTCTCCAACAAAGGCCTCCCA

GCCTCCATCGAGAAAACCATCTCGAAAACCAAAGGGCAGCCCCGAGAACC

ACAGGTGTACACCCTGCCCCCATCCCGGGAGGAGATGACCAAGAACCAGG

TCAGCCTGACCTGCCTGGTCAAAGGCTTCTACCCCAGCGACATCGCCGTG

GAGTGGGAGAGCAATGGGCAGCCGGAGAACAACTACAAGACCACACCTCC

CATGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGA

The entire heavy chain amino acid sequence of the 2105G2Ser (SEQ ID NO: 136):

MELGLSWIFLLAILKGVQCEVQLVESGGGLVQPGRSLRLSCAASGFTFDD

YAMHWVRQAPGKGLEWVSGISWNSGSLVHADSVKGRFTISRDNAKNSLYL

QMNSLRAEDTALYYCARDRLFRGVRYYGMDVWGQGTTVTVSSASTKGPSV

FPLAPCSRSTSESTAALGCLVKDYFPEPVTVSWNSGALTSGVHTFPAVLQ

SSGLYSLSSVVTVPSSNFGTQTYTCNVDHKPSNTKVDKTVERKCCVECPP

CPAPPVAGPSVFLFPPKPKDTLMISRTPEVTCVVVDVSHEDPEVQFNWYV

DGVEVHNAKTKPREEQFNSTFRVVSVLTVVHQDWLNGKEYKCKVSNKGLP

ASIEKTISKTKGQPREPQVYTLPPSREEMTKNQVSLTCLVKGFYPSDIAV

EWESNGQPENNYKTTPPMLDSDGSFFLYSKLTVDKSRWQQGNVFSCSVMH

EALHNHYTQKSLSLSPGK

In the light chain nucleotide sequence (SEQ ID NO: 137) of the 2105G2Ser, the boundary between the signal sequence and the variable region is located between "adenine" ([A]) at position 60 and guanine (G) at position 61, and the boundary between the variable region and the constant region is located between adenine (A) at position 378 and "cytosine" ([C]) at position 379 (the gene prediction software (Signal P ver.2) was used).

In the light chain amino acid sequence (SEQ ID NO: 138) of the 2105G2Ser, the boundary between the signal sequence and the variable region is located between glycine (G) at position 20 and glutamic acid (E) at position 21, and the boundary between the variable region and the constant region is located between lysine (K) at position 126 and "arginine" ([R]) at position 127. Accordingly, the variable region in the light chain of the 2105G2Ser has a nucleotide sequence ranging from guanine (G) at position 61 to adenine (A) at position 378, as seen in SEQ ID NO: 137. Further, the variable region in the light chain of the 2105G2Ser has an amino acid sequence ranging from glutamic acid (E) at position 21 to lysine (K) at position 126, as seen in SEQ ID NO: 138.

The entire light chain nucleotide sequence of the 2105G2Ser (SEQ ID NO: 137):

ATGGAAGCCCCAGCTCAGCTTCTCTTCCTCCTGCTACTCTGGCTCCCAGA

TACCACCGGAGAAATTGTGTTGACACAGTGTCCAGCCACCCTGTCTTTGT

CTCCAGGGGAAAGAGCCACCCTCTCCTGCAGGGCCAGTCAGAGTGTTAGC

AGCTACTTAGCCTGGTACCAACAGAAACCTGGCCAGGCTCCCAGGCTCCT

CATCTATGATGCATCCAACAGGGCCACTGGCATCCCAGCCAGGTTCAGTG

GCAGTGGGTCTGGGACAGACTTCACTCTCACCATCAGCAGCCTAGAGCCT

GAAGATTTTGCAGTTTATTACTGTCAGCAGCGTAGCCACTGGCTCACTTT

CGGCGGGGGGACCAAGGTGGAGATCAAACGTACGGTGGCTGCACCATCTG

TCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGTT

GA

The entire light chain amino acid sequence of the 2105G2Ser (SEQ ID NO: 138):

MEAPAQLLFLLLLWLPDTTGEIVLTQSPATLSLSPGERATLSCRASQSVS

SYLAWYQQKPGQAPRLLIYDASNRATGIPARFSGSGSGTDFTLTISSLEP

EDFAVYYCQQRSHWLTFGGGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

2. Modification of Antagonistic Antibodies

Anti-CD40 antagonistic antibodies will be more preferable as therapeutic agent as well as the agonistic antibodies, if they have not the activities of ADCC and/or CDC, in terms of mechanism of action. Furthermore, it is important that anti-CD40 antagonistic antibodies have no activity to induce signals by their in vivo crosslinking via Fc receptors, even if the ADCC activity cannot be detected. In other words, it is necessary to confirm that they are not activate the immunity, and such active antibodies may be desired as pharmaceutical agent. Anti-CD40 antagonistic antibodies are promising as therapeutic agent for treating autoimmune diseases or suppressing rejection in organ transplantation. If they induce an agonistic activity due to some effect after they are administered to patients, however weak it may be, the symptoms may worsen in contrast to the desired therapeutic effect. Thus, an antibody without any agonistic activity is more preferable as pharmaceutical agent. In the present invention, incorporation of a point mutation L235E (means substitution of L at position 235 with E; similar symbols will be used hereinafter) into IgG4 has been demonstrated to be effective for in vivo reduction in the agonistic activity, in the animal test using monkeys. Although IgG4 is a subclass with low activities of ADCC and CDC, it is reported that when it was attempted to express IgG4 as recombinant protein in cells like CHO, its half-molecules were secreted due to a poor S-S bonding between the heavy chains (Rob C. Aalberse et al., Immunology, 105, 9-19, 2002). To overcome this problem, incorporation of a mutation into the constant region of antibodies is reported to successfully promote the formation of the S-S bonding. Therefore, this type of mutation was also evaluated for its usefulness. Specifically, the mutation of substituting S at position 228 with P was incorporated (S. Angal et al., Molecular Immunology, vol. 30, no. 1, 105-108, 1993).

For antagonistic antibodies as well as agonistic antibodies, the stability of the antibody during purification and storage is very important. There may be some methods to create such antibodies as are physically better while keeping the antagonistic activity. The antibody pharmaceuticals so far offered commercially belong mostly to the IgG1 subclass, and they are not reported to be problematic in pharmaceutical formulation. Based on these facts, it may be advantageous from the viewpoint of physical properties to derive the constant region of antibodies from IgG1. In case of anti-CD40 antibodies, however, they are desirably lower in ADCC and CDC activities. As a consequence, antibodies having an IgG1-type constant region modified with some point mutations may be desired. The mutations described above are useful to create such antibodies. The IgG1-type constant region may become lower in ADCC and CDC activities by incorporating point mutation P331G thereinto. It is also observed that incorporation of point mutation L235E into IgG4 eliminates a slight agonistic activity in vivo to make it pharmaceutically more active, but makes it physically less stable at a low pH. Thus, substitution of L235 with an amino acid other than E may make it physically more functional. As to the 4D11 antibody, it is very similar to the 2B11 antibody with respect to the structure of its variable region. The 2B11 antibody has a lower antagonistic activity, but has a higher stability at a low pH, compared with the 4D11 antibody. If some amino acids derived from the constant region of 2B11 are incorporated into the 4D11 antibody, based on the above properties, 4D11 may become more stable. Specifically, point mutation L38V, P58R, G62W, I79M, K81Y, H87Y, S98A, K109R, V120M or T124A in the heavy chain, or N75S in the light chain, or a combination thereof may be effective for that purpose. Specifically, a mutant created by substituting L at position 38 in the variable region of the heavy chain of the 4D11 antibody with V (abbreviated as L38V; similar symbols will be used hereinafter), a P58R mutant, a G62W mutant, a I79M mutant, a K81Y mutant, a H87Y mutant, a S98A mutant, a K109R mutant, a V120M mutant or a T124A mutant, or a N75S mutant in the light chain, or a combination thereof may be provided for that purpose.

The antibody according to the present invention has at least one mutation of amino acids to reduce the ADCC and/or CDC activities, preferably 1-15, 1-13, 1-12, 1-11, 1-10, 1-9, 1-8, 1-7, 1-6, 1-5, 1-4, 1-3, or 1 or 2 mutations.

The present invention provides mutants of antagonistic anti-CD40 antibodies and others as follows:

[53] A heavy chain of a monoclonal antibody having an antagonistic activity capable of binding to CD40, wherein the heavy chain comprises a constant region with at least one amino acid deleted or substituted, or with at least one amino acid added thereto, said deletion, substitution or addition being capable of increasing or decreasing ADCC and/or CDC.

[54] The heavy chain according to [53], wherein the constant region is derived from a human IgG.

[55] The heavy chain according to [54], wherein the human IgG is a human IgG1.

[56] The heavy chain according to [54], wherein the human IgG is a human IgG2.

[57] The heavy chain according to [54], wherein the human IgG is a human IgG3.

[58] The heavy chain according to [54], wherein the human IgG is a human IgG4.

[59] The heavy chain according to any of [55], [57] or [58], wherein said substitution of amino acids in the constant region is substitution of leucine with glutamic acid at position 235 which is indicated by the EU index as in Kabat et al.

[60] A heavy chain according to any of [53] to [58], wherein the heavy chain comprises a constant region with at least one amino acid deleted or substituted, or with at least one amino acid added thereto, said deletion, substitution or addition being capable of promoting the formation of the S-S bond between the heavy chains.

[61] The antibody heavy chain according to [60], wherein said substitution of amino acids in the constant region is substitution of serine with proline at position 228 which is indicated by the EU index as in Kabat et al.

[62] A monoclonal antibody comprising the heavy chain according to any of [53] to [61].

[63] The heavy chain according to any of [53] to [61], wherein the heavy chain comprises a variable region from a heavy chain of a monoclonal antibody produced by the hybridoma 4D11 (Accession No. FERM BP-7758).

[64] A monoclonal antibody comprising the heavy chain according to [63] and a light chain comprising a variable region from a light chain of a monoclonal antibody produced by the hybridoma 4D11 (Accession No. FERM BP-7758).

[65] The heavy chain according to any of [53] to [61], wherein the heavy chain comprises a variable region of the polypeptide represented by SEQ ID NO: 46.

[66] A monoclonal antibody consisting of the heavy chain according to [65] and a light chain of a monoclonal antibody, wherein the light chain comprises a variable region of the polypeptide represented by SEQ ID NO: 48.

[67] The heavy chain according to [53], wherein the heavy chain consists of a remaining portion provided by removing the signal sequence from the polypeptide represented by SEQ ID NO: 140.

[68] A monoclonal antibody consisting of the heavy chain according to [67] and a light chain of a monoclonal antibody, wherein the light chain consists of a remaining portion provided by removing the signal sequence from the polypeptide represented by SEQ ID NO: 142.

[69] The heavy chain according to [53], wherein the heavy chain is produced by a host comprising an expression vector having the polynucleotide represented by SEQ ID NO: 139.

[70] The monoclonal antibody according to [62], wherein the monoclonal antibody is produced by a host comprising an expression vector having the polynucleotide represented by SEQ ID NO: 139 and the polynucleotide represented by SEQ ID NO: 141.

[71] A polynucleotide represented by SEQ ID NO: 139.

[72] A polynucleotide represented by SEQ ID NO: 141.

[73] An expression vector having the polynucleotide according to [71].

[74] An expression vector having the polynucleotide according to [72].

[75] An expression vector having the polynucleotides according to [71] and [72].

[76] A host comprising the expression vector according to [73].

[77] A host comprising the expression vector according to [74].

[78] A host comprising the expression vector according to [75].

[79] A process of producing a heavy chain of a monoclonal antibody, comprising the steps of: culturing the host according to [76] in a culture medium; and obtaining a heavy chain of a monoclonal antibody from the culture and/or the host.

[80] A process of producing a monoclonal antibody, comprising the steps of: culturing the host according to [78] in a culture medium; and obtaining a monoclonal antibody from the culture and/or the host.

[81] A pharmaceutical composition comprising the monoclonal antibody according to [62], [64], [66], [68] or [70] as an active ingredient.

[82] The pharmaceutical composition according to [81] used for prevention or treatment of transplant rejection, an autoimmune disease, allergy or blood clotting factor VIII inhibition.

[83] A method of prevention or treatment of transplant rejection, an autoimmune disease, allergy or blood clotting factor VIII inhibition, which comprises administering the pharmaceutical composition according to [81] into a mammal.

[84] Use of the monoclonal antibody according to [62], [64], [66], [68] or [70] for production of a pharmaceutical composition used for prevention or treatment of transplant rejection, an autoimmune disease, allergy or blood clotting factor VIII inhibition.

[85] A method of producing a heavy chain of a monoclonal antibody having an antagonistic activity capable of binding to CD40, wherein the agonistic activity is lowered, comprising a step of making deletion or substitution of at least one amino acid, or addition of at least one amino acid in a constant region of a heavy chain of a human antibody.

[86] The method according to [85], wherein the constant region is from a human IgG.

[87] The method according to [86], wherein the human IgG is a human IgG4.

[88] The method according to any of [85] to [87], wherein said substitution of amino acids in the constant region is substitution of leucine with glutamic acid at position 235 which is indicated by the EU index as in Kabat et al.

[93] A polynucleotide provided by removing the portion encoding the signal sequence from the polynucleotide represented by SEQ ID NO: 139.

[94] A polynucleotide provided by removing the portion encoding the signal sequence from the polynucleotide represented by SEQ ID NO: 141.

Additionally, the present invention provides the materials below.

A mutant of an antagonistic anti-CD40 antibody, comprising at least one substitution selected from the group consisting of substitution of L with V at position 38, substitution of P with R at position 58, substitution of G with W at position 62, substitution of I with M at position 79, substitution of K with Y at position 81, substitution of H with Y at position 87, substitution of S with A at position 98, substitution of K with R at position 109, substitution of V with M at position 120 and substitution of T with A at position 124, which substitutions are all carried out in a variable region of a heavy chain of a monoclonal antibody produced by the hybridoma 4D11 (Accession No. FERM BP-7758), and a mutant of an antagonistic anti-CD40 antibody comprising substitution of N with S at position 75 in a variable region of a light chain of the 4D11 antibody.

Herein, reduction in ADCC and CDC activities means reduction in those activities as compared with the corresponding activities of an anti-CD40 monoclonal antibody other than the mutants described above, for example, as compared with the corresponding activities of a monoclonal antibody produced by the hybridoma 4D11 (Accession No. FERM BP-7758). The ADCC and CDC activities may be assayed by any known method, for example, the method described in the Examples herein. The sequences of variable regions in the heavy and light chains of a monoclonal antibody will be presented below which is produced by the hybridoma 4D11 (Accession No. FERM BP-7758).

DNA encoding variable regions in the heavy and light chains of the 4D11 antibody and the amino acid sequences of the heavy and light chains will be presented below, respectively.

In the heavy chain nucleotide sequence (SEQ ID NO: 45) of the 4D11 antibody, the boundary between the signal sequence and the variable region is located between "cytosine" ([C]) at position 93 and cytosine (C) at position 94, and the boundary between the variable region and the constant region is located between adenine (A) at position 456 and guanine (G) at position 457 (the gene prediction software (Signal P ver.2) was used).

In the heavy chain amino acid sequence (SEQ ID NO: 46) of the 4D11 antibody, the boundary between the signal sequence and the variable region is located between serine (S) at position 26 and glutamine (Q) at position 27, and the boundary between the variable region and the constant region is located between serine (S) at position 147 and alanine (A) at position 148.

Accordingly, the variable region in the heavy chain of the 4D11 antibody has a nucleotide sequence ranging from cytosine (C) at position 94 to adenine (A) at position 456, as seen in SEQ ID NO: 45. Further, the variable region in the heavy chain of the 4D11 antibody has an amino acid sequence ranging from glutamine (Q) at position 27 to serine (S) at position 147, as seen in SEQ ID NO: 46.

In the light chain nucleotide sequence (SEQ ID NO: 47) of the 4D11 antibody, the boundary between the signal sequence and the variable region is located between "thymine" ([T]) at position 124 and guanine (G) at position 125, and the boundary between the variable region and the constant region is located between adenine (A) at position 442 and "cytosine" ([C]) at position 443 (the gene prediction software (Signal P ver.2) was used).

In the light chain amino acid sequence (SEQ ID NO: 48) of the 4D11 antibody, the boundary between the signal sequence and the variable region is located between cytosine (C) at position 22 and alanine (A) at position 23, and the boundary between the variable region and the constant region is located between lysine (K) at position 128 and "arginine" ([R]) at position 129.

Accordingly, the variable region in the light chain of the 4D11 antibody has a nucleotide sequence ranging from guanine (G) at position 125 to adenine (A) at position 442, as seen in SEQ ID NO: 47. Further, the variable region in the light chain of the 4D11 antibody has an amino acid sequence ranging from alanine (A) at position 23 to lysine (K) at position 128, as seen in SEQ ID NO: 48.

The heavy chain nucleotide sequence (SEQ ID NO: 45) of the 4D11 antibody:

```
ATATGTCGACGAGTCATGGATCTCATGTGCAAGAAAATGAAGCACCTGTG

GTTCTTCCTCCTGCTGGTGGCGGCTCCCAGATGGGTCCTGTCCCAGCTGC

AGCTGCAGGAGTCGGGCCCAGGACTACTGAAGCCTTCGGAGACCCTGTCC

CTCACCTGCACTGTCTCTGGCGGCTCCATCAGCAGTCCTGGTTACTACGG

GGGCTGGATCCGCCAGCCCCCAGGGAAGGGGCTGGAGTGGATTGGGAGTA

TCTATAAAAGTGGGAGCACCTACCACAACCCGTCCCTCAAGAGTCGAGTC

ACCATATCCGTAGACACGTCCAAGAACCAGTTCTCCCTGAAGCTGAGCTC

TGTGACCGCCGCAGACACGGCTGTGTATTACTGTACGAGACCTGTAGTAC

GATATTTTGGGTGGTTCGACCCCTGGGGCCAGGGAACCCTGGTCACCGTC

TCCTCAGCTAGC
```

The heavy chain amino acid sequence (SEQ ID NO: 46) of the 4D11 antibody:

```
MDLMCKKMKHLWFFLLLVAAPRWVLSQLQLQESGPGLLKPSETLSLTCTV

SGGSISSPGYYGGWIRQPPGKGLEWIGSIYKSGSTYHNPSLKSRVTISVD

TSKNQFSLKLSSVTAADTAVYYCTRPVVRYFGWFDPWGQGTLVTVSSAS
```

The light chain nucleotide sequence (SEQ ID NO: 47) of the 4D11 antibody:

AGATCTTAAGCAAGTGTAACAACTCAGAGTACGCGGGGAGACCCACTCAG

GACACAGCATGGACATGAGGGTCCCCGCTCAGCTCCTGGGGCTTCTGCTG

CTCTGGCTCCCAGGTGCCAGATGTGCCATCCAGTTGACCCAGTCTCCATC

CTCCCTGTCTGCATCTGTAGGAGACAGAGTCACCATCACTTGCCGGGCAA

GTCAGGGCATTAGCAGTGCTTTAGCCTGGTATCAGCAGAAACCAGGGAAA

GCTCCTAAGCTCCTGATCTATGATGCCTCCAATTTGGAAAGTGGGGTCCC

ATCAAGGTTCAGCGGCAGTGGATCTGGGACAGATTTCACTCTCACCATCA

GCAGCCTGCAGCCTGAAGATTTTGCAACTTACTGTCAACAGTTTAATAGT

TACCCGACGTTCGGCCAAGGGACCAAGGTGGAAATCAAACGTACG

The light chain amino acid sequence (SEQ ID NO: 48) of the 4D11 antibody:

MDMRVPAQLLGLLLLWLPGARCAIQLTQSPSSLSASVGDRVTTTCRASQG

ISSALAWYQQKPGKAPKLLIYDASNLESGVPSRFSGSGSGTDFTLTISSL

QPEDFATYYCQQFNSYPTFGQGTKVEIKRT

In the heavy chain nucleotide sequence (SEQ ID NO: 139) of the 4D11 antibody G4PE, the boundary between the signal sequence and the variable region is located between "cytosine" ([C]) at position 78 and cytosine (C) at position 79, and the boundary between the variable region and the constant region is located between adenine (A) at position 441 and guanine (G) at position 442 (the gene prediction software (Signal P ver.2) was used).

In the heavy chain amino acid sequence (SEQ ID NO: 140) of the 4D11 antibody, the boundary between the signal sequence and the variable region is located between serine (S) at position 26 and glutamine (Q) at position 27, and the boundary between the variable region and the constant region is located between serine (S) at position 147 and alanine (A) at position 148.

Accordingly, the variable region in the heavy chain of the 4D11 antibody has a nucleotide sequence ranging from cytosine (C) at position 79 to adenine (A) at position 441, as seen in SEQ ID NO: 139. Further, the variable region in the heavy chain of the 4D11 antibody has an amino acid sequence ranging from glutamine (Q) at position 27 to serine (S) at position 147, as seen in SEQ ID NO: 140.

The entire heavy chain nucleotide sequence (SEQ ID NO: 139) of the 4D11G4PE:

ATGGATCTCATGTGCAAGAAAATGAAGCACCTGTGGTTCTTCCTCCTGCT

GGTGGCGGCTCCCAGATGGGTCCTGTCCCAGCTGCAGCTGCAGGAGTCGG

GCCCAGGACTACTGAAGCCTTCGGAGACCCTGTCCCTCACCTGCACTGTC

TCTGGCGGCTCCATCAGCAGTCCTGGTTACTACGGGGCTGGATCCGCCA

GCCCCCAGGGAAGGGGCTGGAGTGGATTGGGAGTATCTATAAAAGTGGGA

GCACCTACCACAACCCGTCCCTCAAGAGTCGAGTCACCATATCCGTAGAC

ACGTCCAAGAACCAGTTCTCCCTGAAGCTGAGCTCTGTGACCGCCGCAGA

CACGGCTGTGTATTACTGTACGAGACCTGTAGTACGATATTTTGGGTGGT

-continued

TCGACCCCTGGGGCCAGGGAACCCTGGTCACCGTCTCCTCAGCTAGCACC

AAGGGGCCATCCGTCTTCCCCCTGGCGCCCTGCTCCAGGAGCACCTCCGA

GAGCACAGCCGCCCTGGGCTGCCTGGTCAAGGACTACTTCCCCGAACCGG

TGACGGTGTCGTGGAACTCAGGCGCCCTGACCAGCGGCGTGCACACCTTC

CCGGCTGTCCTACAGTCCTCAGGACTCTACTCCCTCAGCAGCGTGGTGAC

CGTGCCCTCCAGCAGCTTGGGCACGAAGACCTACACCTGCAACGTAGATC

ACAAGCCCAGCAACACCAAGGTGGACAAGAGAGTTGAGTCCAAATATGGT

CCCCCATGCCCACCATGCCCAGCACCTGAGTTCGAGGGGGGACCATCAGT

CTTCCTGTTCCCCCCAAAACCCAAGGACACTCTCATGATCTCCCGGACCC

CTGAGGTCACGTGCGTGGTGGTGGACGTGAGCCAGGAAGACCCCGAGGTC

CAGTTCAACTGGTACGTGGATGGCGTGGAGGTGCATAATGCCAAGACAAA

GCCGCGGGAGGAGCAGTTCAACAGCACGTACCGTGTGGTCAGCGTCCTCA

CCGTCCTGCACCAGGACTGGCTGAACGGCAAGGAGTACAAGTGCAAGGTC

TCCAACAAAGGCCTCCCGTCCTCCATCGAGAAAACCATCTCCAAAGCCAA

AGGGCAGCCCCGAGAGCCACAGGTGTACACCCTGCCCCCATCCCAGGAGG

AGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAA

CTACAAGACCACGCCTCCCGTGCTGGACTCCGACGGCTCCTTCTTCCTCT

ACAGCAGGCTAACCGTGGACAAGAGCAGGTGGCAGGAGGGGAATGTCTTC

TCATGCTCCGTGATGCATGAGGCTCTGCACAACCACTACACACAGAAGAG

CCTCTCCCTGTCTCTGGGTAAATGA

The entire heavy chain amino acid sequence (SEQ ID NO: 140) of the 4D11G4PE:

MDLMCKXMKHLWFFLLLLVAAPRWVLSQLQLQESGPGLLKPSETLSLTCTV

SGGSISSPGYYGGWIRQPPGKGLEWIGSIYKSGSTYHNPSLKSRVTISVD

TSKNQFSLKLSSVTAADTAVYYCTRPVVRYFGWFDPWGQGTLVTVSSAST

KGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYG

PPCPPCPAPEFEGGPSVFLFPPKPKDTLMISRTPEVTCVVVDVSQEDPEV

QFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNVF

SCSVMHEALHNHYTQKSLSLSLGK

In the light chain nucleotide sequence (SEQ ID NO: 141) of the 4D11G4PE, the boundary between the signal sequence and the variable region is located between "thymine" ([T]) at position 66 and guanine (G) at position 67, and the boundary between the variable region and the constant region is located between adenine (A) at position 384 and "cytosine" ([C]) at position 385 (the gene prediction software (Signal P ver.2) was used).

In the light chain amino acid sequence (SEQ ID NO: 142) of the 4D11G4PE, the boundary between the signal sequence and the variable region is located between cytosine (C) at position 22 and alanine (A) at position 23, and the boundary between the variable region and the constant region is located between lysine (K) at position 128 and "arginine" ([R]) at position 129.

Accordingly, the variable region in the light chain of the 4D11G4PE has a nucleotide sequence ranging from guanine (G) at position 67 to adenine (A) at position 384, as seen in SEQ ID NO: 141. Further, the variable region in the light chain of the 4D11 antibody has an amino acid sequence ranging from alanine (A) at position 23 to lysine (K) at position 128, as seen in SEQ ID NO: 142.

The entire light chain nucleotide sequence (SEQ ID NO: 141) of the 4D11G4PE:

```
ATGGACATGAGGGTCCCCGCTCAGCTCCTGGGGCTTCTGCTGCTCTGGCT
CCCAGGTGCCAGATGTGCCATCCAGTTGACCCAGTCTCCATCCTCCCTGT
CTGCATCTGTAGGAGACAGAGTCACCATCACTTGCCGGGCAAGTCAGGGC
ATTAGCAGTGCTTTAGCCTGGTATCAGCAGAAACCAGGGAAAGCTCCTAA
GCTCCTGATCTATGATGCCTCCAATTTGGAAAGTGGGGTCCCATCAAGGT
TCAGCGGCAGTGGATCTGGGACAGATTTCACTCTCACCATCAGCAGCCTG
CAGCCTGAAGATTTTGCAACTTATTACTGTCAACAGTTTAATAGTTACCC
GACGTTCGGCCAAGGGACCAAGGTGGAAATCAAAGCTACGGTGGCTGCAC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTG
TCACAGAGCAGGACAGCAAGGACAGCACCTACAGCCTCAGCAGCACCCTG
ACGGTGAGCAAAGCAGACTACGAGAAACACAAAGTCTACGCCTGCGAAGT
CACCCATCAGGGCCTGAGCTCGCCCGTCACAAAGAGCTTCAACAGGGGAC
AGTGTTGA
```

The entire light chain amino acid sequence (SEQ ID NO: 142) of the 4D11G4PE:

```
MDMRVPAQLLGLLLLWLPGARCAIQLTQSPSSLSASVGDRVTITCRASQG
ISSALAWYQQKPGKAPKLLIYDASNLESGVPSRFSGSGSGTDFTLTISSL
QPEDFATYYCQQFNSYPTFGQGTKVEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFNRGEC
```

3. Definition

The terms used herein will be defined below.

"CD40" described in the present invention refers to a polypeptide having the amino acid sequence described in E. A. Clark et al., Proc. Natl. Acad. Sci. USA 83: 4494, 1986, or I. Stamenkovic et al., EMBO J. 8: 1403, 1989, and particularly, an antigenic polypeptide expressed on the surface of B cells, DC, macrophages, endothelial cells, epithelial cells or tumor cells derived from them. "An anti-CD40 antibody" refers to any monoclonal antibody to a cell-expressed CD40, a full-length CD40 or a partial-length CD40.

In addition, "an antibody" of the invention is derived from genes (collectively called antibody genes) encoding a heavy chain variable region and a heavy chain constant region, as well as a light chain variable region and a light chain constant region which together constitute an immunoglobulin. Human immunoglobulins are grouped into 5 different classes consisting of IgG, IgA, IgM, IgD, and IgE. Further, IgG is composed of 4 different subclasses, IgG1, IgG2, IgG3 and IgG4, while IgA is composed of 2 different subclasses, IgA1 and IgA2. IgG1, IgG2, IgG3 and IgG4 are located in 14q32, 33 of the human chromosomes. The fundamental structure of immunoglobulin is composed of two homologous L chains (light chains) and two homologous H chains (heavy chains). The class and subclass of an immunoglobulin is determined by its H chains. The antibody according to the present invention may comprise any class, any subclass or any isotype of immunoglobulin. "A functional fragment" of the inventive antibody refers to a portion (partial fragment) of the antibody defined above that is active singly or multiply on an antigen to the antibody, including, for example, F(ab')$_2$, Fab', Fab, Fv, disulfide-stabilized FV, single-chain FV (scFV) and a multimer thereof (D. J. King, Applications and Engineering of Monoclonal Antibodies, 1998, T. J. International Ltd.).

Up to now, it has been known that IgG1 includes J00228, Z17370 and Y14737, IgG2 includes J00230, AJ250170, AF449616, AF449617, AF449618, Z49802 and Z49801, IgG3 includes M12958, K01313, X16110, X99549, AJ390236, AJ390237, AJ390238, AJ390241, AJ390242, AJ390246, AJ390247, AJ390252, AJ390244, AJ390254, AJ390260, AJ390262, AJ390272, AJ390276 and AJ390279, and IgG4 includes K01316, AJ001563 and AJ001564 (the symbols listed above indicates accession numbers of the genes).

In the present invention, CH1, hinge, CH2 and CH3 each denote a portion of the heavy-chain constant region of any antibody, and are based on the EU index as in Kabat et al. (Kabat et al., Sequences of proteins of immunological interest, 1991 Fifth edition). By definition, CHI ranges from 118 to 215 by the EU index, hinge ranges from 216 to 230 by the EU index, CH2 ranges from 231 to 340 by the EU index, and CH3 ranges from 341 to 446 by the EU index.

The "human antibody" of the present invention means an antibody which is an expression product of a human-derived antibody gene.

"Agonistic" refers to an action of enhancing binding of a ligand to CD40 expressed on the surface of such cells as B cells, tumor cells or dendritic cells, or an action of providing the CD40-expressing cells with at least one effect which the CD40 ligand makes on the CD40-expressing cells. "An agonistic antibody" refers to an antibody having such an agonistic action. An example of the effects provided for the CD40-expressing cells is to promote the expression of CD95.

"Antagonistic" refers to an action of inhibiting binding of the ligand to CD40 expressed on the surface of such cells as B cells, tumor cells or dendritic cells, or an action of neutralizing at least one effect which the CD40 ligand makes on the CD40-expressing cells. "An antagonistic antibody" refers to an antibody having such an antagonistic action. An example of the effects provided for the CD40-expressing cells is to suppress the proliferation of B cells or the production of antibodies.

The present application clearly presents antibodies, or heavy chain or light chain variable regions thereof by amino acid sequences. The present invention also encompasses the amino acid sequences with at least one amino acid deleted or substituted, or added thereto, preferably 1-10, 1-9, 1-8, 1-7, 1-6, 1-5, 1-4, 1-3, or 1 or 2 amino acids.

The present application clearly presents genes which encode antibodies, or heavy chain or light chain variable regions thereof by nucleotide sequences. The present invention also encompasses the nucleotide sequences with at least one nucleotide deleted or substituted, or added thereto, preferably 1-10, 1-9, 1-8, 1-7, 1-6, 1-5, 1-4, 1-3, or 1 or 2 amino acids.

The anti-CD40 antibody according to the present invention can be provided by incorporating an antibody gene into an expression vector, transfecting the vector into a suitable host cell, harvesting the antibody from the cultured cells or the supernatant, and purifying it.

The vector may be a phage or a plasmid which can replicate in the host cell by itself or can be integrated into the chromosome of the host cell. The plasmid DNA may be derived from *Escherichia coli, Bacillus sibtilis* or a yeast, while the phage DNA may be from λ phage.

The host cell for transformation is not particularly limited if it can express the target gene. Examples of the host cell may include bacteria (*Escherichia coli, Bacillus subtilis*, etc.), yeasts, animal cells (COS cell, CHO cell, etc.) and insect cells.

There are known modes of transferring the gene into the host cells, including any mode, such as mediation by calcium ion, electroporation, spheroplast fusion, mediation by lithium acetate, calcium phosphate transfection or lipofection. In order to transfer the gene into an animal, as described later, the modes include microinjection; electroporation or lipofection for ES cells; and nuclear transplantation.

In the present invention, "culture" refers to (a) culture supernatant, (b) cultured cells, cultured biomass or disrupted matter thereof, or (c) secretion of transformant. To culture the transformant, a medium suitable for the host is used and static culture, roller bottle culture or something else may be employed.

After the culture, if the desired antibody protein is produced within the biomass or cells, the antibody is harvested by disrupting the biomass or cells. If the desired antibody is produced out of the biomass or cells, the culture solution is used as it is or after it is separated from the biomass or cells by centrifugation or other means. Thereafter, a biochemical process utilizing any chromatography, which is appropriate for separation/purification of proteins, is employed alone or optionally in combination with another to separate/isolate the desired antibody from the culture.

Furthermore, the technology of creating a transgenic animal may be used to produce a transgenic animal that is a host animal having the gene integrated into an endogenous gene, such as a transgenic bovine, a transgenic goat, a transgenic sheep or a transgenic pig (Wright, G., et al., (1991) Bio/Technology 9, 830-834) and a large amount of a monoclonal antibody derived from the antibody gene can be obtained from the milk secreted from the transgenic animal. The culture of a hybridoma in vitro can be done by using a known nutrient medium or any nutrient medium derivatively prepared from known basic media as used to grow, maintain and store the hybridoma and to produce a monoclonal antibody in the supernatant, depending on the properties of the cultured hybridoma, the purpose of the study and the culture method.

4. Antibody Properties (1) Agonistic Antibodies

The mutant of the agonistic antibody according to the present invention may activate the immune system without injuring immunocompetent cells, since it has an ADCC and/or CDC activity equal to or lower than the original antibody, while keeping an agonistic activity. It is thus expected that the mutant exhibits the immunoactivating action which is equal to or higher than the original antibody and the cytotoxicity to CD40-expressing cells which is equal to or lower than the original antibody.

(2) Antagonistic Antibodies

The mutant of the antagonistic anti-CD40 antibody according to the present invention has the reduced ADCC and/or CDC activity compared to the unmodified antibody, while keeping a suppressive activity against immunoactivating signals induced by CD40L. It is also expected to decrease the activity of signal induction in vivo which is considered to occur via Fc receptors.

5. Pharmaceutical Compositions

A pharmaceutical composition containing a formulation of the purified antibody according to the present invention is also within the scope of the present invention. The pharmaceutical composition may preferably contain a physiologically acceptable diluent or carrier in addition to the antibody, and may be a mixture thereof with a different antibody or a different drug such as an antibiotic agent. The suitable carrier may include, but not limited to, physiological saline, phosphate buffered physiological saline, phosphate buffered physiological saline glucose solution and buffered physiological saline. Alternatively, the antibody may be freeze-dried for storage and when it is used, reconstituted in an aqueous buffer as described above. The pharmaceutical composition may be administered via the oral route, or the parenteral route, such as intravenous, intramuscular, subcutaneous or intraperitoneal injection or dosing.

A single effective dose, which is a combination of the antibody of the present antibody with a suitable diluent and a physiologically acceptable carrier, is from 0.0001 mg to 100 mg per kg of body weight, and it may be taken at a time interval of from 2 days to 8 weeks.

When the pharmaceutical composition of the present antibody is an agonistic antibody, it is used as: immunostimulant (antiviral or anti-infective agent) for pathogens including, for example, hepatitis A, B, C, D or E virus, HIV, influenza virus, simple herpes virus, cytomegalovirus, EB virus, papiloma virus, chlamydia, mycoplasma, toxoplasma, malaria, trypanosome and tubercle bacillus; antitumor agent for malignant tumors having cancer cells with CD40 expressed, including, for example, pancreatic cancer, bladder cancer, lymphoma (e.g., Hodgkin's lymphoma), leukemia, malignant melanoma, pancreatic cancer, lung cancer, ovarian cancer, bladder cancer, breast cancer, colon cancer, prostatic cancer, and head and neck cancer; and therapeutic agent for autoimmune diseases such as rheumatism. The pharmaceutical composition may be used for a combination of the above diseases. It may be also used in combination as adjuvant for a cancer-specific peptide. When the pharmaceutical composition is an antagonistic antibody, on the other hand, it is useful as: immunosuppressant in organ transplantation (preventive or therapeutic agent for rejection in transplantation of pancreatic islets, kidney or something else, or GVHD), therapeutic agent for autoimmune diseases (e.g., rheumatism, psoriasis, chronic ulcerative colitis, Crohn's disease, systemic lupus erythematosus, multiple sclerosis, myasthenia, scleroderma, antiphospholipid antibodies syndrome, autoimmune hepatitis, idiopathic thrombocytopenic purpura, Behcet's syndrome, arteriosclerosis, nephritis and respiratory distress syndrome), therapeutic agent for allergy (e.g., asthma), and therapeutic agent for blood clotting factor VIII inhibition. The pharmaceutical composition may be used for a combination of the above diseases.

6. Epitopes

The binding epitopes of CD40 were determined for the KM341-1-19 and 2105 antibodies having a superior agonistic activity, and for the 4D11 antibody having a superior antagonistic activity, respectively (Example 2). The present invention provides antibodies having an agonistic or antagonistic activity which have a different variable region sequence from those of the above antibodies but recognize the same epitope as one of the above antibodies. These antibodies can be obtained in such a procedure as described below.

When it is intended to acquire an agonistic anti-CD40 antibody recognizing the same epitope as the KM341-1-19 antibody, for example, mice or the likes are immunized with CD40 to provide monoclonal antibodies, from which some monoclonal antibodies competing with the KM341-1-19 antibody to bind to CD40 are screened according to the standard procedure. From the screened antibodies, an antibody having the same pattern of binding to the peptide as the KM341-1-19 antibody is selected according to the method described in Example 2.

The present invention will be described in more detail below with reference to examples. However, the present invention is not limited to embodiments described in the examples.

EXAMPLE 1

Expression and Purification of Antibody and Antigen Proteins

A vector plasmid containing a variable region of an antibody was transfected into CHO cells (ATCC), and antibody-expressing cells were selected by G418 to prepare a stable expression cell line.

A mutant antigen was expressed by transiently introducing a vector into HEK cells (ATCC).

An anti-CD40 antibody was purified from the above culture supernatant by the following method. The culture supernatant containing an anti-CD40 antibody was affinity purified in a Hyper D® Protein A column (manufactured by NGK Insulators, Ltd.) or in case of mouse IgG1 purification, a Protein G column (Amersham Pharmacia Biotech) according to the attached instruction using PBS(−) as an adsorption buffer and a 0.1 M sodium citrate buffer (pH 3) as an elution buffer. The eluted fraction was adjusted to about pH 7.2 by addition of a 1 M Tris-HCI (pH 8.0) or Na2HPO4 solution. The prepared antibody solution was substituted with PBS(−) using a dialysis membrane (10,000 cuts, manufactured by Spectrum Laboratories, Inc.) or an SP column (Amersham Pharmacia Biotech), and filtered and sterilized using a membrane filter MILLEX®-GV with a pore diameter of 0.22 µm (manufactured by Millipore Corp.). The concentration of the purified antibody was calculated by measurement of the absorbance at 280 nm, taking 1 mg/ml as 1.450D.

EXAMPLE 2

Determination of epitopes

A 13-mer peptide covering amino acid 175 (SEQ ID NO: 1) in an extracellular region of CD40 was shifted by two amino acids each to synthesize 82 peptides in total (SEQ ID NOS: 49 to 130) as spots from the C-terminal on a cellulose membrane and acetylate the N-terminal thereof (Jerini AG, Germany). The reaction thereafter was carried out based on a conventional Western analysis (see Reineke, U. et al. (2001), "Epitope mapping with synthetic peptides prepared by SPOT synthesis." Antibody Engineering (Springer Lab Manual) Eds.: Kontermann/Dubel, 433-459, for example). In the analysis, coloring intensity of each spot was quantified using Lumilmager™ (Boehringer-Mannheim Corp.) (FIG. 1A-1, 1A-2, 1B-1 and B-2).

The results confirmed that an 4D11 antibody strongly recognizes the 20th to 24th and 41st peptides, a 2105 antibody strongly recognizes the 12th to 23rd and 64th peptides, a KM341-1-19 antibody strongly recognizes the 41st and 42nd peptides, KM643-4-11 strongly recognizes the 43rd peptide, F72 strongly recognizes the 75th peptide, 110 strongly recognizes the 64th peptide, F4-465 strongly recognizes the 34th, 35th, 54th, 55th, 65th, 66th and peptides, KM281-1-10 strongly recognizes the 21st, 24th, 64th and 75th peptides, 2B11 (novel antibody) strongly recognizes the 21st, 24th and 64th peptides, and F76 (novel antibody) strongly recognizes the 21 st, 35th, 51 st and 52nd peptides.

In order to confirm the binding site of the anti-CD40 antibody, a CD40-FC fusion protein having a mutation introduced thereinto was prepared, and the binding ability thereto was examined by ELISA. Since the anti-CD40 antibody does not cross-react with mouse B cells, five CD4OFc fusion proteins were prepared by partially converting the amino acid sequence into that of mouse CD40. Binding of the antibody to the antigens was examined. The method for preparing the mutant CD40-FC fusion proteins is shown below. The mutation site was prepared by introducing a mouse CD40 sequence into a part to which the antibody strongly binds of the peptide sequence. CD40mut1 converted EFTE at a site corresponding to the 15th peptide into ALEK, CD40mut2 converted LDT at a site corresponding to the 21st peptide into SAQ, CD40mut3 converted TH at a site corresponding to the 24th peptide into IR, CD40mut4 converted EEGW at a site corresponding to the 42nd peptide into KEGQ, and CD40mut5 converted VSSA at a site corresponding to the 64th peptide into QSSL. The mutants were prepared according to a gene engineering technique (FIGS. 2A, B and C). The analysis results confirmed that the 2105 antibody has extremely reduced binding ability to CD40mut1. The results also confirmed that the 4D11 antibody and 2B11 have reduced binding ability to CD40mut2.

EXAMPLE 3

Binding Activity of Anti-CD40 Agonistic Antibody to Ramos Cells

A Ramos cell line was suspended in a PBS staining buffer (SB) containing 0.1% $NaN_3$ and 2% FCS at a concentration of $2 \times 10^6$/ml. The cell suspension (100 µl/well) was dispensed to a 96-well round-bottom plate (manufactured by Becton, Dickinson and Company). Each hybridoma culture supernatant (50 µl) was added, and incubated at an ice temperature for 30 minutes. A human IgG1 antibody to human serum albumin as a negative control was adjusted to a concentration of 2 µg/ml in a hybridoma culture medium, added in an amount of 50 µl, and then incubated at an ice temperature for 15 minutes. After washing the plate with SB, 50 µl of a 250-fold diluted R-PE fluorescently labeled anti-human antibody (manufactured by Southern Biotechnology Associates, Inc.) was added, and incubated at an ice temperature for 15 minutes. After washing the plate with SB twice, it was suspended in 300 to 500 µl of a FACS buffer, and fluorescence intensity of each cell was measured using FACS (FACSort, FACScan, manufactured by Becton, Dickinson and Company).

EXAMPLE 4

Evaluation of Agonistic Activity of Anti-CD40 Agonistic Antibody to Ramos Cells $5.0 \times 10^5$ cells/ml of a Ramos cell suspension was seeded on a 96-well plate at 100 µl/well. A hybridoma culture supernatant or purified antibody was diluted to 20 µg/ml in a medium, and the dilution was added to the 96-well plate at a concentration of 100 µl/well. After culturing overnight, cells were harvested, and R-PE labeled anti-CD95 antibody (Pharmingen NJ) was used for the cells. Analysis was carried out using FACScan or FACSsort (Becton, Dickinson and Company).

EXAMPLE 5

Inhibition of CD95 Expression by Anti-CD40 Antagonistic Antibody in Ramos Cells $1.0 \times 10^6$ cells/ml of a Ramos cell suspension was seeded on a 96-well plate at 50 µl/well. A hybridoma culture supernatant or purified antibody was adjusted to 2 µg/ml in a medium, and the medium was added to the 96-well plate at 100 µl/well. 4 µg/ml of a soluble CD40 ligand (Alexis Corporation) and 4 µg/ml of an anti-FLAG antibody (M2, Sigma) were added to a medium, and the medium was added to a 96-well plate at 50 µl/well. After culturing overnight, cells were harvested, and an R-PE labeled anti-CD95 antibody (Pharmingen NJ) was used for the cells. Analysis was carried out using FACS.

EXAMPLE 6

Measurement of CDC Activity in Anti-CD40 Antibody

In the CDC assay, 2,000 $Cr^{51}$-labeled target cells and a human serum-derived complement (manufactured by Sigma Co.) or rabbit serum-derived complement (Cedarlane Laboratories Limited, Ontario, Canada) at a final concentration of 5% were cultured in a round-bottom 96-well plate in a total volume of 200 µL together with the antibody at various concentrations at 37° C. in the presence of 5% $CO_2$ for two hours.

After culturing, the plate was centrifuged to cause the cells to precipitate, and then 50 µL of the supernatant was transferred to a 96-well plate including a powder scintillator (Lumaplate™-96: manufactured by Packard Instrument Co., Inc.) and dried at 55° C. for 1.5 hours. After confirming that the plate was dried, it was covered with a special cover (TopSeal™-A: 96-well microplates: manufactured by Packard Instrument Co., Inc.), and the γ-ray dose was measured with a scintillation counter (TopCount: manufactured by Packard Instrument Co., Inc.).

EXAMPLE 7

Measurement of ADCC Activity of Anti-CD40 Antibody

As antibody-mediated cytotoxicity, cytotoxicity to target cells in the presence of cells having killer activity such as NK cells or neutrophils and an antibody (Antibody-Dependent Cellular Cytotoxicity, hereinafter ADCC), and cytotoxicity to target cells in the presence of a complement and an antibody (Complement-Dependent Cytotoxicity, hereinafter CDC) were measured. hIgG was used as a control.

The measurement method is simply described as follows. Radioactive chromium ($Cr^{51}$) was incorporated into the cytoplasm of the target cells, and the amount of $Cr^{51}$ released in the culture solution by cell death was measured as a γ-ray dose.

Specifically, $10^5$ target cells of a Burkitt's lymphoma cell line Raji (ATCC CCL-86) were suspended in 15 µL of fetal calf serum (FCS). 50 µL (37 MBq/mL) of $Cr^{51}$-labeled sodium chromate (manufactured by PerkinElmer, Inc.: hereinafter referred to as $Cr^{51}$) was added to the suspension, and the cells were cultured at 37° C. for one hour. Next, 10 mL of a medium was added, and the medium was discarded by centrifugation. This operation was repeated three times to remove $Cr^{51}$ not incorporated in the cells.

In the ADCC assay, 2,000 $Cr^{51}$-labeled target cells and 200,000 healthy human peripheral blood mononuclear leukocytes obtained by the method described in Example 6 were cultured in a round-bottom 96-well plate (manufactured by Falcon) in a total volume of 200 µL together with the antibody at various concentrations at 37° C. in the presence of 5% $CO_2$ for four hours.

After culturing, the plate was centrifuged to cause the cells to precipitate, and then 50 µL of the supernatant was transferred to a 96-well plate including a powder scintillator (Lumaplate™-96: manufactured by Packard Instrument Co., Inc.) and dried at 55° C. for 1.5 hours. After confirming that the plate was dried, the plate was covered with a special cover (TopSeal™-A: 96-well microplates: manufactured by Packard Instrument Co., Inc.), and the γ-ray dose was measured with a scintillation counter (TopCount: manufactured by Packard Instrument Co., Inc.).

EXAMPLE 8

Preparation and Activity Evaluation of Anti-CD40 Agonistic Antibody P331S Mutant Gene cloning of anti-CD40 agonistic antibodies KM341-1-19 and 2105 is described in WO 02/099186. It is reported that CDC activity is reduced by converting Pro at position 331 in the IgG2 constant region into Ser. To reduce CDC activity of the KM341-1-19 antibody and the 2105 antibody, a P331 S mutation was introduced into the IgG2 constant region thereof The human IgG1 constant region of an antibody-expressing vector N5KG1-Val Lark (IDEC Pharmaceuticals: hereinafter abbreviated to N5KG1) was substituted with human IgG2 to prepare N5KG2, and the Pro at position 331 of IgG2 was converted into Ser to prepare a mutation. cDNA cloning of the IgG2 constant region was carried out by harvesting KM341-1-19 hybridoma by centrifugation, adding TRIZOL (Gibco BRL), and extracting total RNA according to the instruction. The antibody cDNA variable region was cloned using a SMART RACE cDNA amplification kit of Clontech Laboratories, Inc. according to the attached instruction. 1st strand cDNA was prepared using 5 µg of total RNA as a template. PCR was carried out with tnIgG3Nhe: atatGCTAGCACCAAGGGCCCATCGGTCTTCCCCCTGGC (SEQ ID NO: 2)G and tnIgG2Bam: atatggatccTCATTTACCCGGAGACAGGGAGAGGCTC (SEQ ID: 3) as primer sequences using a ZtaqPCR kit (Takara) in 30 cycles each consisting of reaction at 98° C. for 1 second, at 55° C. for 30 seconds and at 72° C. for 1 minute to amplify the gene. After the reaction, the amplified product was purified by a QIAGEN PCR purification kit, digested with NheI and BamHI, and incorporated into N5KG1 to confirm the sequence. This vector was defined as N5KG2.

N5KG2Ser (with Pro at position 331 converted into Ser) was prepared as follows. Reaction at 98° C. for 1 second, at 60° C. for 30 seconds and at 72° C. for 30 seconds was carried out 15 times using N5KG2 as a template and primers IgG3Nhe: atatGCTAGCACCAAGGGCCCATCGGTCTTCCCCCTGGCG (SEQ ID NO: 4) and G2Ser2: GTTTTCTCGATGGAGGCTGGGAGGCC (SEQ ID NO: 5). At the same time, reaction at 98° C. for 1 second, at 60° C. for 30 seconds and at 72° C. for 30 seconds was carried out 15 times using N5KG2 as a template and primers IgG2Bam: atatggatccTCATTTACCCGGAGACAGGGAGAGGCTC (SEQ ID NO: 6) and G2Ser1: GGCCTCCCAGCCTCCATC-GAGAAAAC (SEQ ID NO: 7). The amplified DNA fragments were purified using a PCR purification kit, and the same amounts of the two purified DNA fragments were mixed. Thereafter, reaction at 98° C. for 1 second, at 60° C. for 30 seconds and at 72° C. for 30 seconds was carried out five times. Primers IgG3Nhe and IgG2Bam were added to the mixture, and the same reaction was carried out 15 times. The amplified DNA fragment was cleaved with NheI and BamHI, and substituted with the IgG1 constant region of the N5KG1 vector (N5KG2Ser). The fragment containing the sequence of the antibody variable region digested with BglII and NheI was incorporated into the N5KG2Ser vector.

Figure 3A:
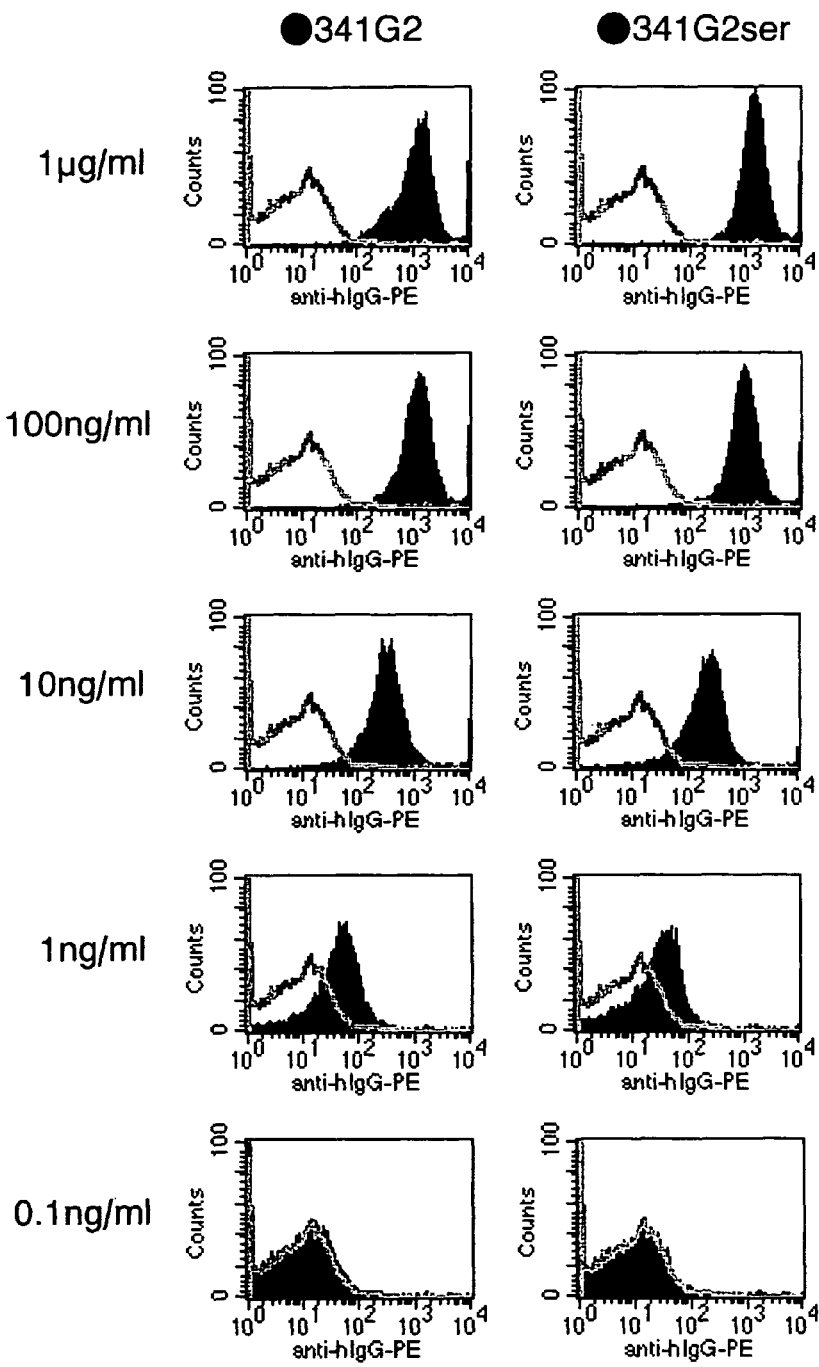
FIG. 3A shows diagrams indicating that the KM341-1-19 antibody having a P331S mutation is as active as the original KM341-1-19 antibody with respect to binding to Ramos cells.

The antibody expressed and purified by the above method was evaluated in terms of binding ability to Ramos cells (FIG. 3A) and agonistic activity (FIG. 3B). The fluctuation in activity due to introduction of the P331S variation was not observed.

EXAMPLE 9

Measurement of CDC Activity of Anti-CD40 Agonistic Antibody 133 ser Mutant

Figure 4A:
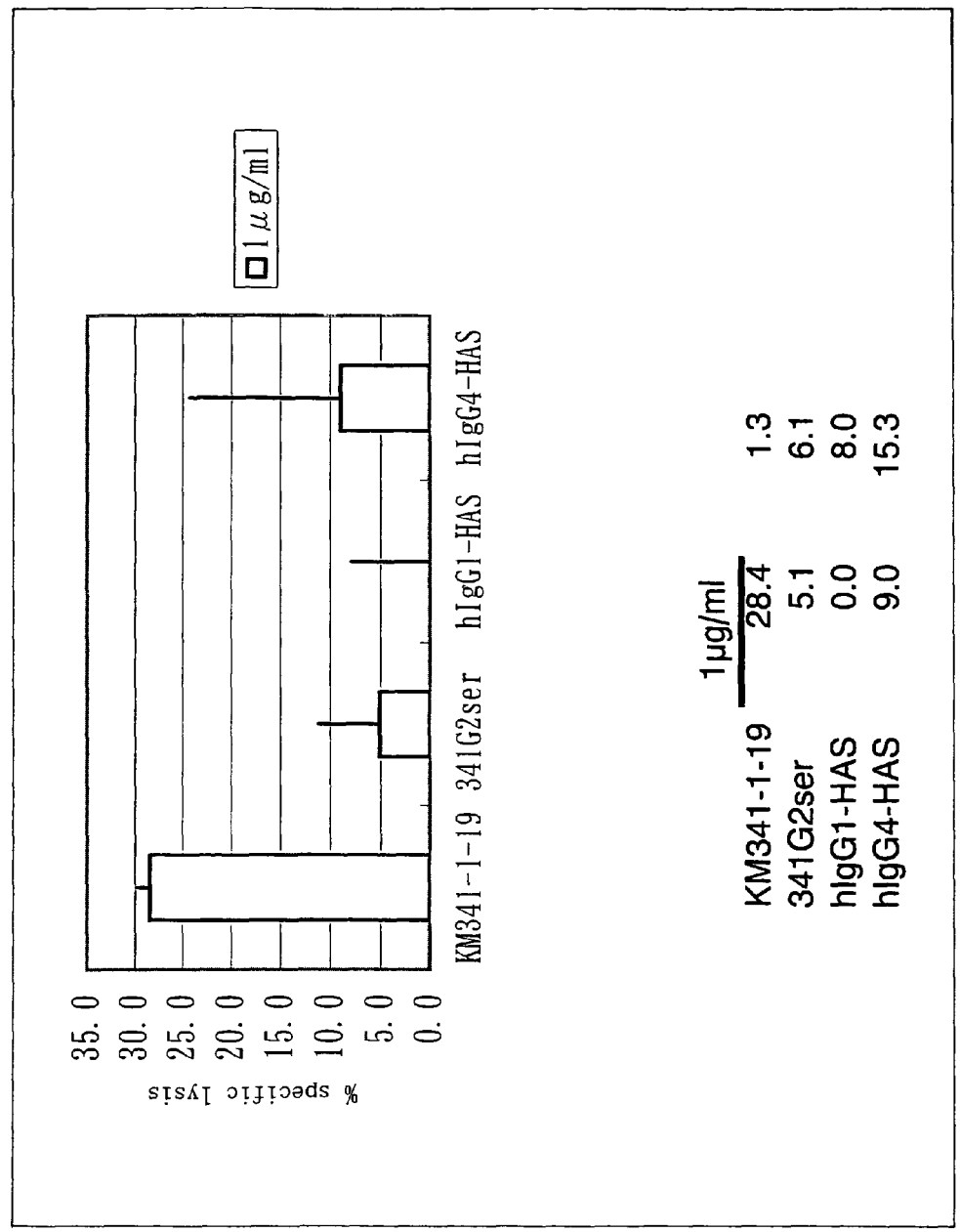
FIG. 4A shows a diagram indicating that the KM341-1-19 antibody having a P331S mutation has a lower CDC activity via the rabbit complement.
Figure 4B:
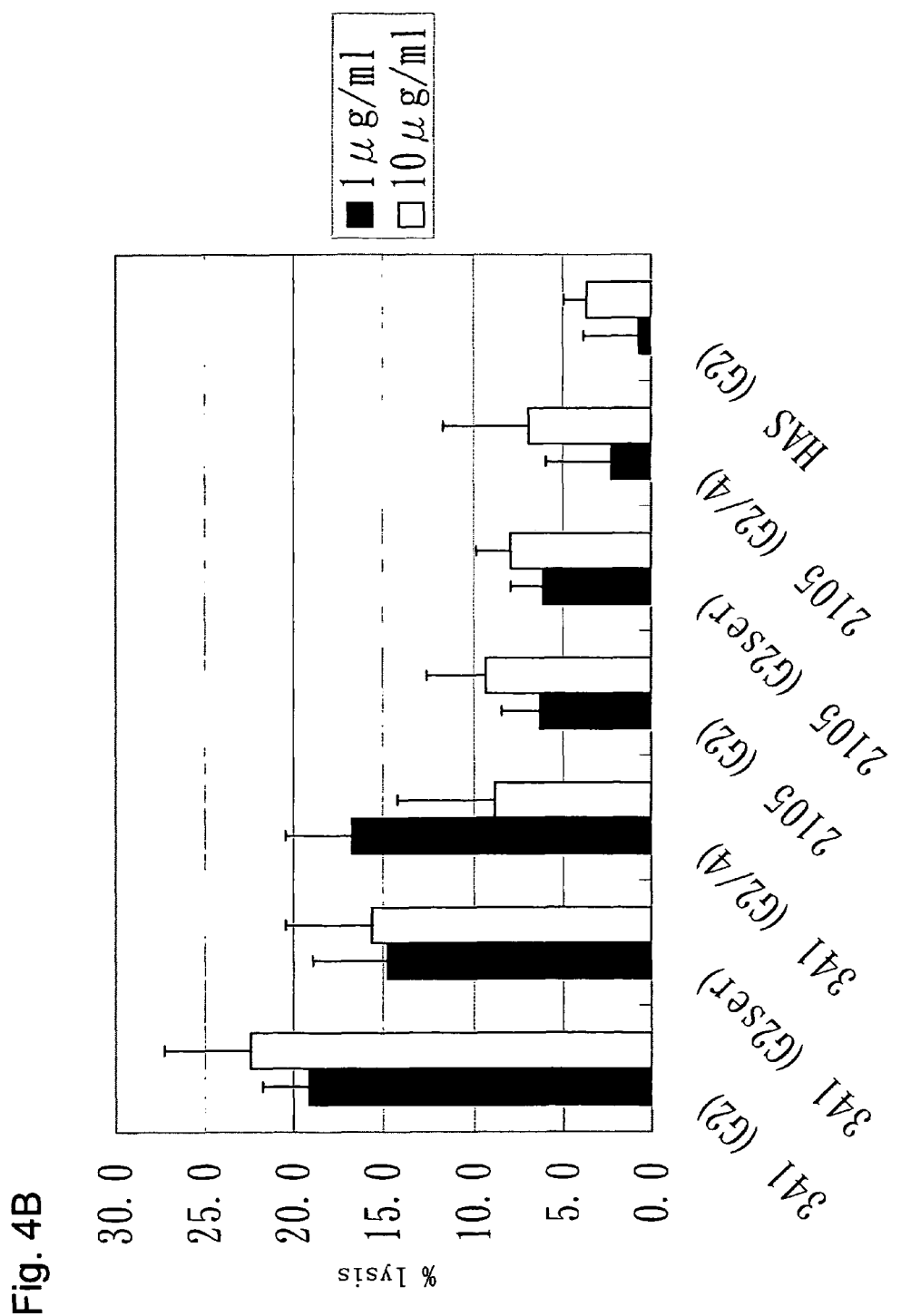
FIG. 4B shows a diagram indicating that the G2/4 antibody has a lower complement activity when the human complement is used.

CDC activity was measured by the above method. A rabbit serum-derived complement was used, and Ramos cells were used as target cells. The results confirmed that, in a KM341-1-19 antibody at an antibody concentration of 1 µg/ml, IgG2ser exhibited CDC activity significantly reduced as compared with IgG2 (FIG. 4A). On the other hand, when a human supplement was used, no change was observed (FIG. 4B).

EXAMPLE 10

Preparation and Activity Measurement of Agonist Anti-CD40 Antibody having Constant Region Converted Among the Anti-CD Antibodies Described in WO 02/088186, Two Antibodies Exhibiting strongest agonistic activity (KM341-1-19 antibody and 2105 antibody) belong to IgG2 subclass. In order to examine whether or not the IgG2 subclass is important for activation of CD40, recombinant proteins having an antibody constant region converted into IgG1, IgG3 and IgG4, respectively, were prepared, and measured in terms of binding ability to an antigen and CD95 expression enhancing activity in Ramos cells according to Examples 4 and 6. IgG1 was expressed using N5KG1, and IgG2 and IgG3 were respectively expressed using expression vectors N5KG2 and N5KG3 obtained by substituting the N5KG1 constant region with IgG2 and IgG3, respectively. cDNA cloning of the IgG3 constant region was carried out according to the IgG2 cloning method partially modified, using an IgG3-specific primer. IgG4 was expressed using N5KG4PE (IDEC Pharmaceuticals).

Figures 1, 5A:
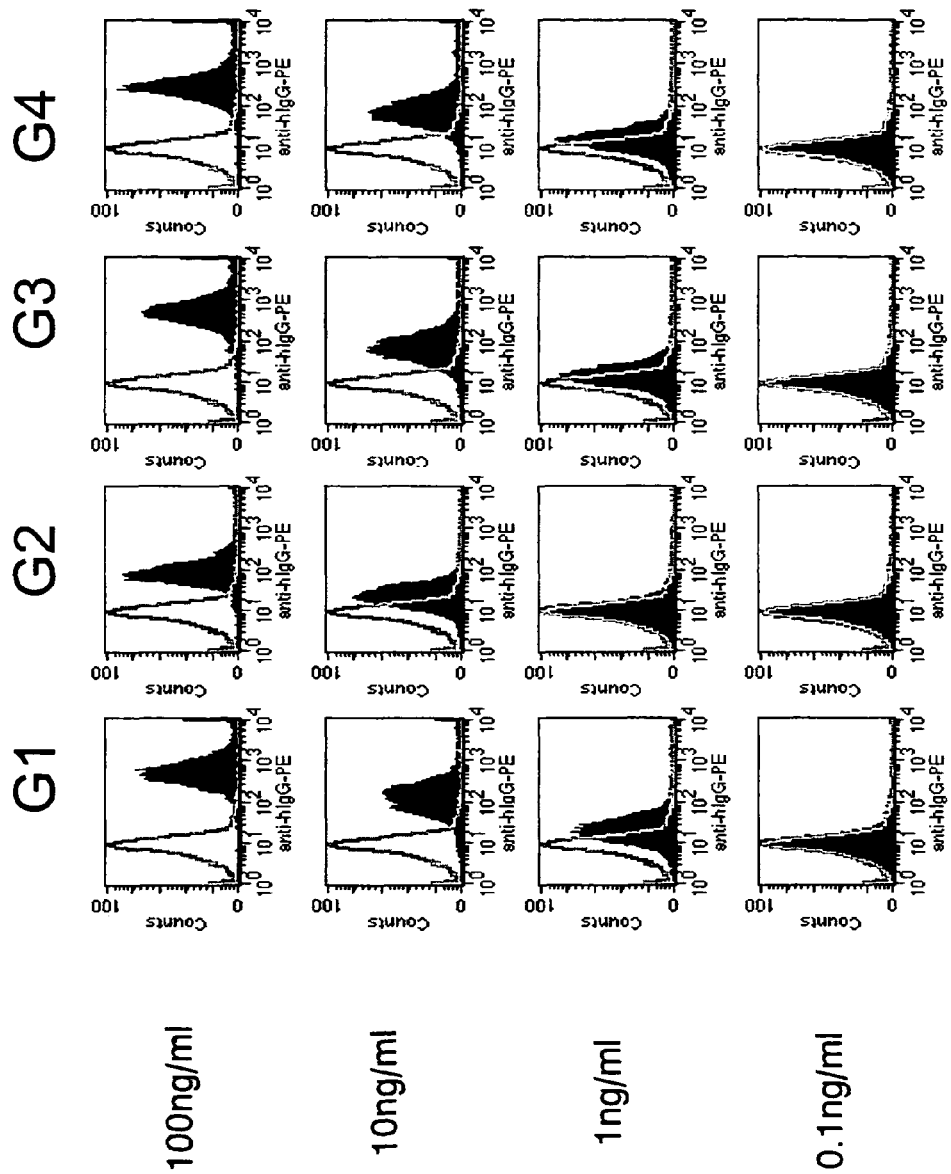
Figures 2, 5A:
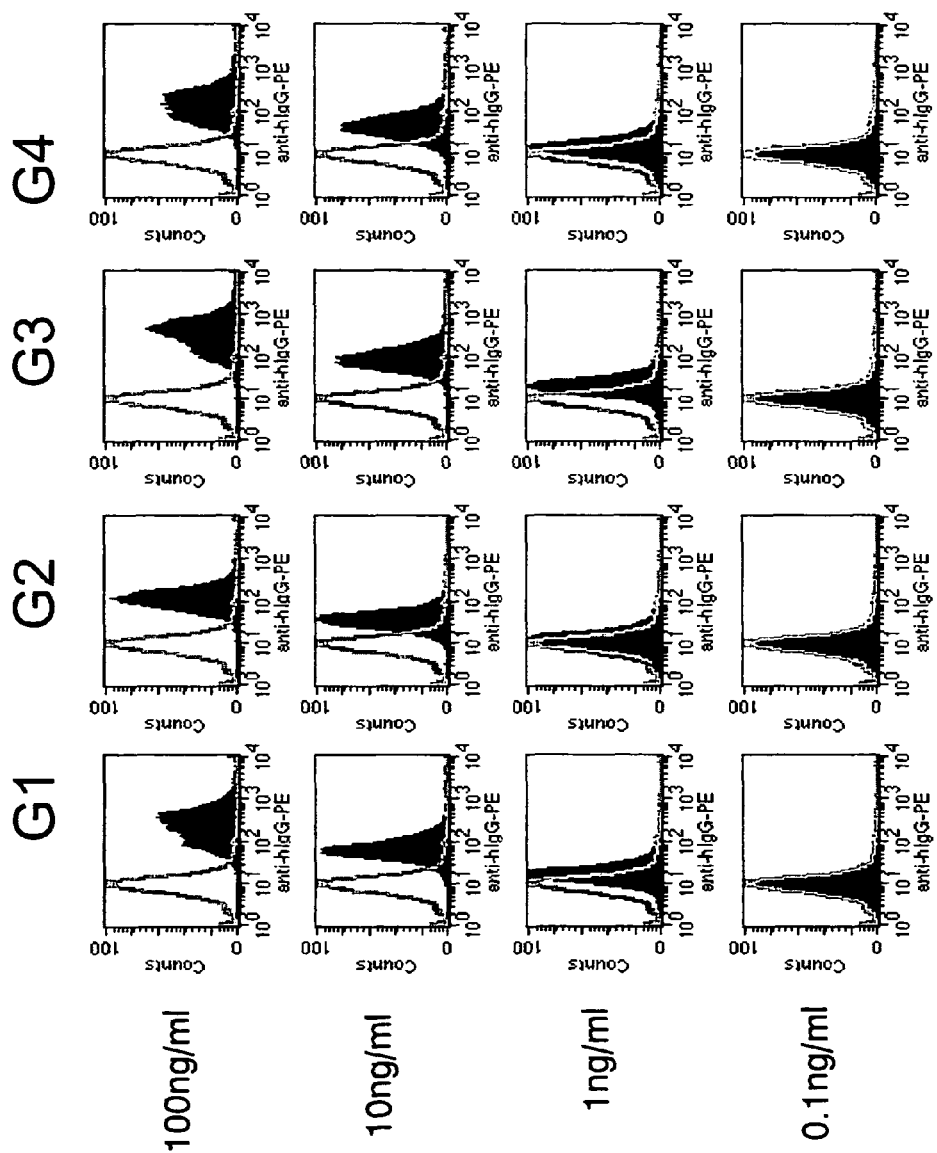
Figures 1, 5B:
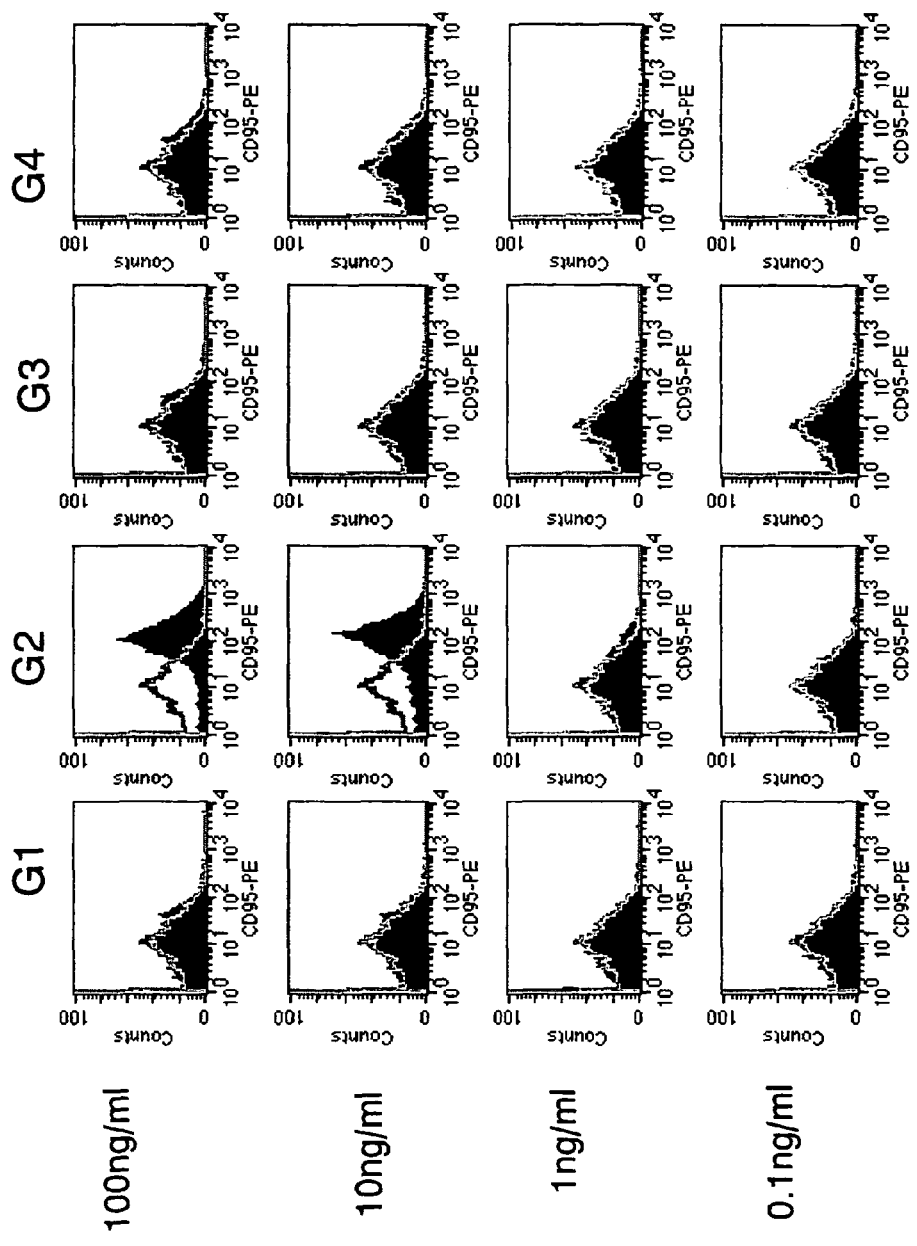
Figures 2, 5B:
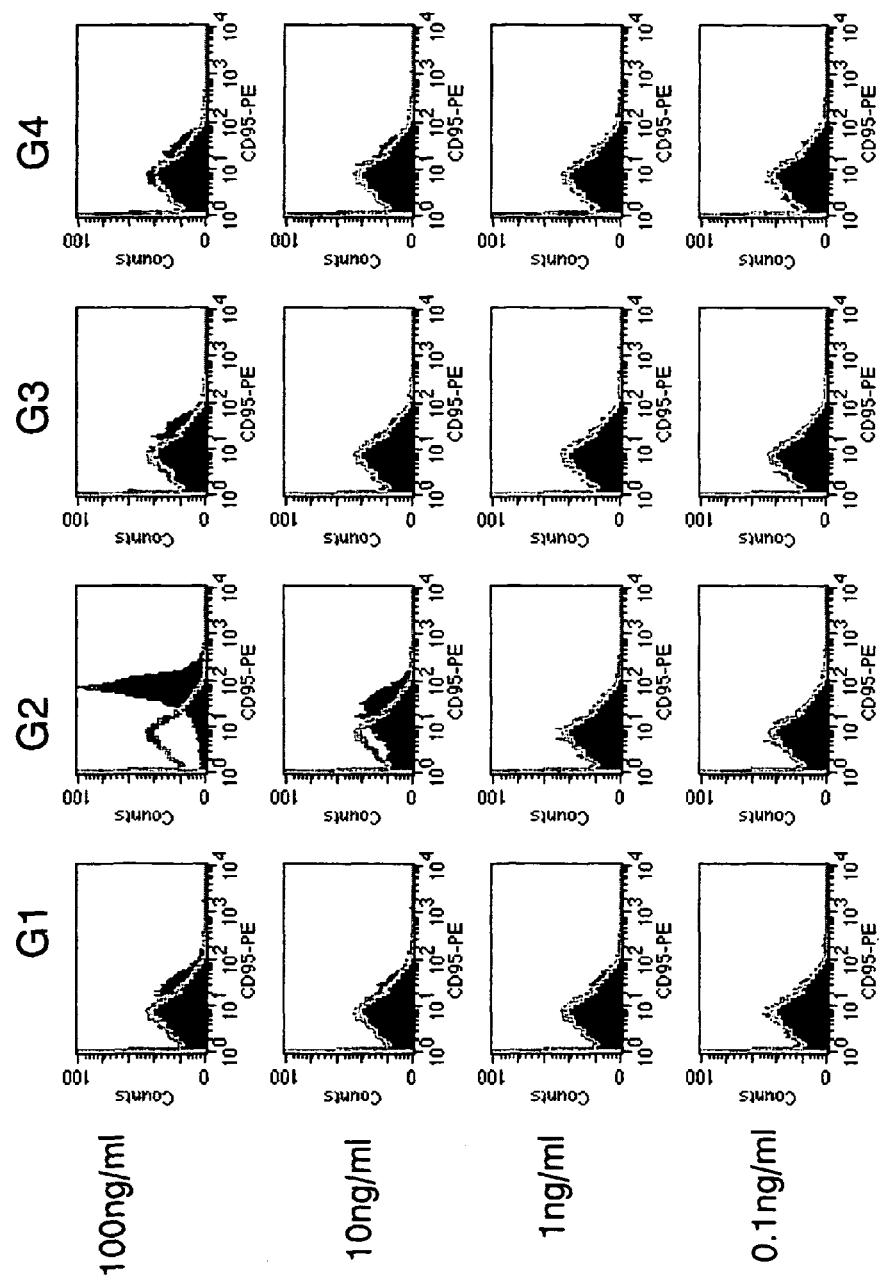

The antibody protein was expressed according to Example 1. Binding activity to Ramos cells expressing human CD40 of the KM341-1-19 antibody and the 2105 antibody was not affected by converting IgG2 into IgG1, IgG3 or IgG4 (FIGS. 5A-1 and 5A-2). However, these antibodies were found to have CD95 expression enhancing activity in Ramos cells reduced by 10% or more (FIGS. 5B-1 and 5B-2). This shows that not only the structure of the variable region defining the binding region of the antibody but also the structure of the constant region of the antibody are important for the strong agonistic activity of the 2105 antibody and the KM341-1-19 antibody. Thus, in order to examine which region in the IgG2 constant region is important for agonistic activity, a domain swap mutant in which the IgG2 structure is mixed with the IgG4 structure was prepared to measure its activity. As described below, a domain swap mutant is prepared by substitution of a hinge region. In this case, the "hinge region" includes the upper hinge (from Kabat EU code 216), middle hinge (from Kabat EU code 226) and lower hinge (Kabat EU code 231), as described Ole H Brekke et. al., Immunology Today 1995, 16, 85-90. Four domain swap mutants IgG2/4 (CHI and hinge region: IgG2, other regions: IgG4), IgG4/2/4 (hinge region: IgG2, other regions: IgG4), IgG2/4/4 (CHI: IgG2, other regions: IgG4) and IgG4/2/2 (CHI: IgG4, other regions: IgG2) were prepared respectively for the KM341-1-19 antibody and the 2105 antibody.

A vector N5KG2/4 for expressing the IgG2/4 antibody was prepared using a Ztaq PCR kit (Takara). Reaction at 98° C. for 1 second, at 60° C. for 30 seconds and at 72° C. for 30 seconds was carried out 15 times using N5KG2 as a template and primers IgG3Bam: atatggatccTCATTTACCCGGAGA-CAGGGAGAGGC (SEQ ID NO: 8) and 24Chi4: AGGGGTCCGGGAGATCATGAGAGTGTCCTT (SEQ ID NO: 9). At the same time, reaction at 98° C. for 1 second, at 60° C. for 30 seconds and at 72° C. for 30 seconds was carried out 15 times using N5KG4 (IDEC Pharmaceuticals) as a template and primers 24Chi3: AAGGACACTCTCAT-GATCTCCCGGACCCCT (SEQ ID NO: 10) and linkH2: tgatcatacgtagatatcacggc (SEQ ID NO: 11). The amplified DNA fragments were purified using a PCR purification kit, and the same amounts of the two purified DNA fragments were mixed. Thereafter, reaction at 98° C. for 1 second, at 60° C. for 30 seconds and at 72° C. for 30 seconds was carried out five times. Primers IgG3Bam and linkH2: tgatcatacgtagatat-cacggc (SEQ ID NO: 12) were added to the mixture, and the same reaction was carried out 15 times. The amplified DNA fragment was cleaved with NheI and BamHI, and substituted with the IgG1 constant region of the N5KG1 vector.

A vector N5KG4/2/4 for expressing IgG4/2/4 was prepared as follows. Reaction at 98° C. for 1 second, at 60° C. for 30 seconds and at 72° C. for 30 seconds was carried out 15 times using N5KG4 as a template and primers linkh: ggg-tacgtcctcacattcagtgatcag (SEQ ID NO: 13), G2Hin3: TTTGCGCTCAACTGTCTTGTCCACCTTG-GTGTTGCTGGG (SEQ ID NO: 14), 1 inkH2: tgatcatacgta-gatatcacggc (SEQ ID NO: 15) and G2Hin4: ACAGT-TGAGCGCAAATGTTGTGTCGAGTGCCCACCG (SEQ ID NO: 16). The amplified DNA fragments were purified with a PCR purification kit, and the same amounts of the two purified DNA fragments were mixed. Thereafter, reaction at 98° C. for 1 second, at 60° C. for 30 seconds and at 72° C. for 30 seconds was carried out five times using the mixture as a template. Primers linkH and linkH2 were added to the mixture, and the same reaction was carried out 15 times. The amplified DNA fragment was cleaved with NheI and BamHI, and substituted with the IgG1 constant region of the N5KG1 vector.

A vector N5KG2/4/4 for expressing IgG2/4/4 was prepared as follows. Reaction at 98° C. for 1 second, at 60° C. for 30 seconds and at 72° C. for 30 seconds was carried out 15 times using N5KG2 as a template and primers linkH: ggg-tacgtcctcacattcagtgatcag (SEQ ID NO: 17) and G4CH1-2: GGTGTTGCTGGGCTTGTGATCTACGTTGCAG.(SEQ ID NO: 18). At the same time, reaction at 98° C. for 1 second, at 60° C. for 30 seconds and at 72° C. for 30 seconds was carried out 15 times using N5KG4 as a template and primers G4CH1-1: CTGCAACGTAGATCACAAGCCCAGCAA- CACC (SEQ ID NO: 19) and linkH2: tgatcatacgtagatatcacggc (SEQ ID NO: 20). The amplified DNA fragments were purified using a PCR purification kit, and the same amounts of the two purified DNA fragments were mixed. Thereafter, reaction at 98° C. for 1 second, at 60° C. for 30 seconds and at 72° C. for 30 seconds was carried out five times. Primers linkH and linkH2 were added to the mixture, and the same reaction was carried out 15 times. The amplified DNA fragment was cleaved with NheI and BamHI, and substituted with the IgG1 constant region of the N5KG1 vector.

A vector N5KG4/2/2 for expressing IgG4/2/2 was prepared as follows. Reaction at 98° C. for 1 second, at 60° C. for 30 seconds and at 72° C. for 30 seconds was carried out using N5KG4 as a template and primers linkH: gggtacgtcctcacattcagtgatcag (SEQ ID NO: 21) and G4CH1-2: GGTGTTGCTGGGCTTGTGATCTACGTTGCAG (SEQ ID NO: 22). At the same time, reaction at 98° C. for 1 second, at 60° C. for 30 seconds and at 72° C. for 30 seconds was carried out 15 times using N5KG2 as a template and primers G4CH1-1: CTGCAACGTAGATCACAAGCCCAGCAACACC (SEQ ID NO: 23) and linkH2: tgatcatacgtagatatcacggc (SEQ ID NO: 24). The amplified DNA fragments were purified using a PCR purification kit, and the same amounts of the two purified DNA fragments were mixed. Thereafter, reaction at 98° C. for 1 second, at 60° C. for 30 seconds and at 72° C. for 30 seconds was carried out five times. Primers linkH and linkH2 were added to the mixture, and the same reaction was carried out 15 times. The amplified DNA fragment was cleaved with NheI and BamHI, and substituted with the IgG1 constant region of the N5KG1 vector.

Figures 1, 6A:
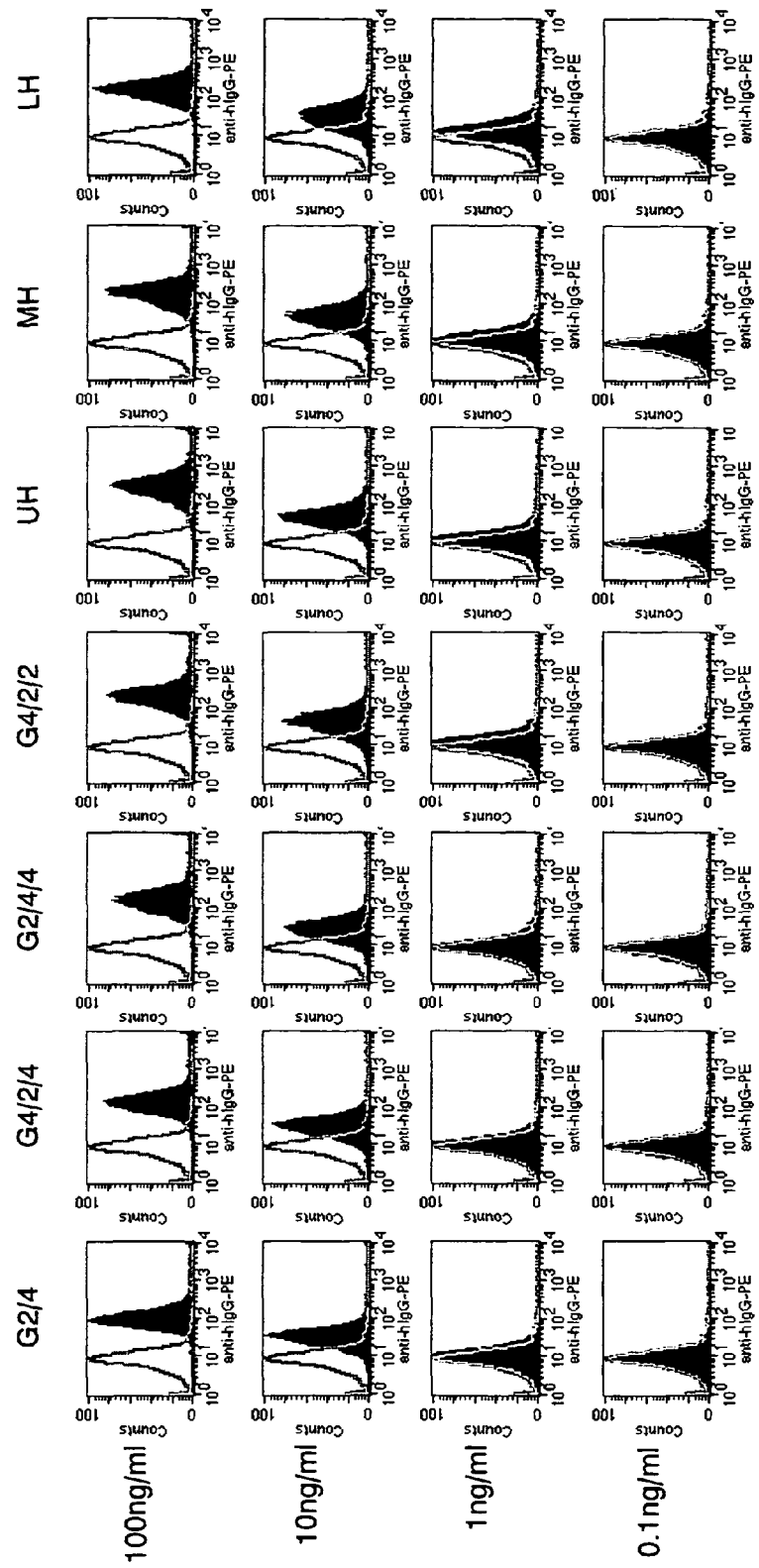
Figures 2, 6A:
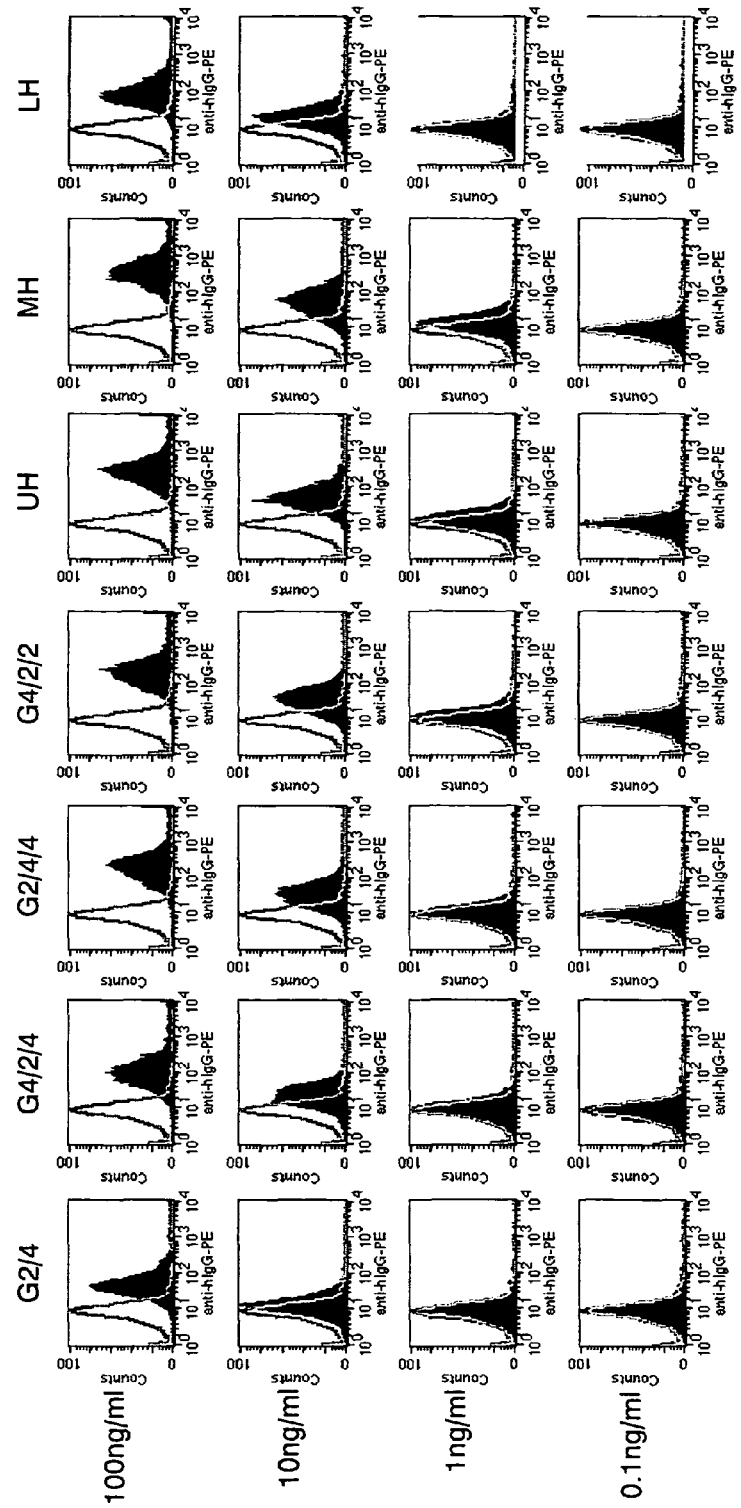
Figures 1, 6B:
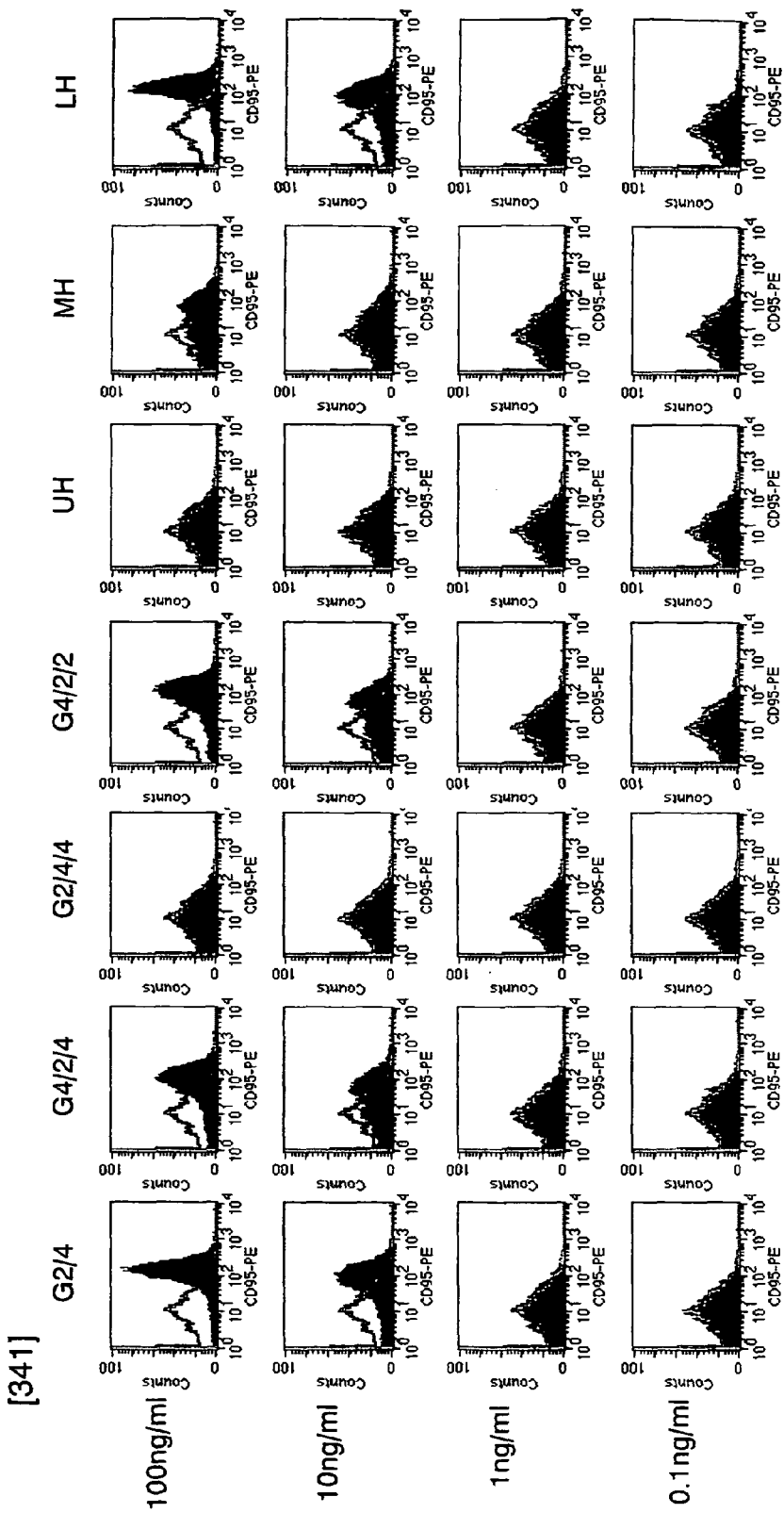
Figures 2, 6B:
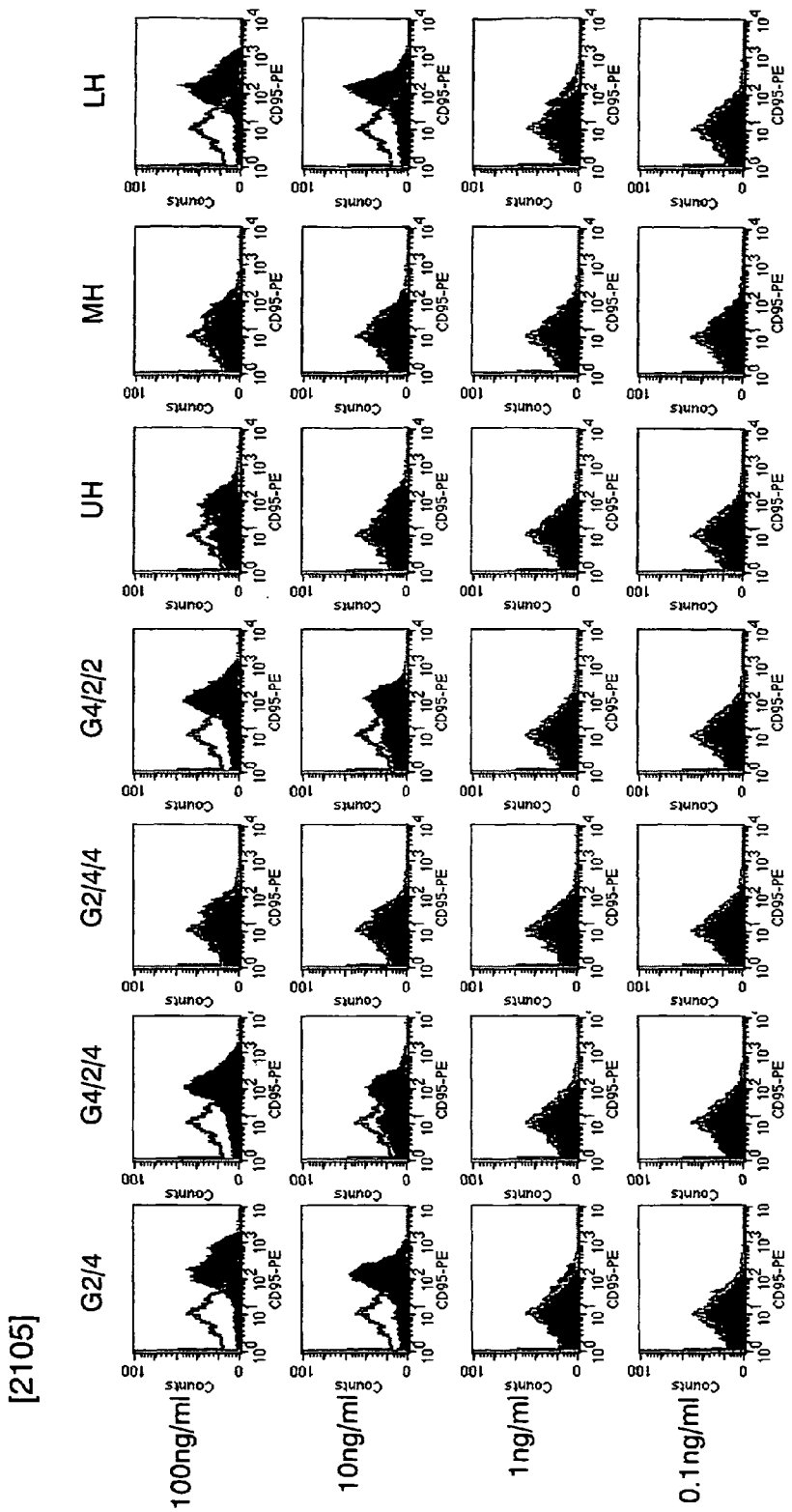

Binding activity of the respective four domain swap mutants of the KM341-1-19 antibody and the 2105 antibody was examined. As a result, no difference between them and the original IgG2 was observed in terms of binding ability (FIGS. 6A-1 and 6A-2). However, only IgG2/4/4 of both the KM341-1-19 antibody and the 2105 antibody exhibited significantly reduced agonistic activity (FIGS. 6B-1 and 6B-2). The results confirmed that the hinge region of IgG2 is important for agonistic activity.

Further, it was examined which sequence is important in the hinge region. The hinge region is divided into three sites, specifically, upper hinge, middle hinge and lower hinge (Ole H Brekke et al. Immunology Today 1995, 16, 85-90). IgG2-specific sequences in these regions were respectively substituted with IgG4-specific sequences. Antibodies obtained by introducing a mutation into the upper hinge (from Kabat EU code 216), middle hinge (from Kabat EU code 226) and lower hinge (from Kabat EU code 231) were respectively defined as IgG2UH4, IgG2MH4 and IgG2LH4. Their respective expression vectors were defined as N5KG2UH4, N5KG2MH4 and N5KG2LH4. "Hinge" is defined as EU indices 216 to 230 according to Kabat et al., Sequences of proteins of immunological interest, 1991 Fifth edition.

N5KG2UH4 was prepared as follows. Reaction at 98° C. for 1 second, at 60° C. for 30 seconds and at 72° C. for 30 seconds was carried out 15 times using N5KG2 as a template and primers linkH: gggtacgtcctcacattcagtgatcag (SEQ ID NO: 25) and UH4-2: CACAACATTTggaCTCAACTcTCTTGTCCACC (SEQ ID NO: 26). At the same time, reaction at 98° C. for 1 second, at 60° C. for 30 seconds and at 72° C. for 30 seconds was carried out 15 times using N5KG2 as a template and primers UH4-1: GGTGGACAAGAgAGTTGAGtccAAATGTTGTG (SEQ ID NO: 27) and linkH2: tgatcatacgtagatatcacggc (SEQ ID NO: 28). The amplified DNA fragments were purified using a PCR purification kit, and the same amounts of the two purified DNA fragments were mixed. Thereafter, reaction at 98° C. for 1 second, at 60° C. for 30 seconds and at 72° C. for 30 seconds was carried out five times. Primers linkH and linkH2 were added to the mixture, and the same reaction was carried out 15 times. The amplified DNA fragment was cleaved with NheI and BamHI, and substituted with the IgG1 constant region of the N5KG1 vector.

N5KG2MH4 was prepared as follows. Reaction at 98° C. for 1 second, at 60° C. for 30 seconds and at 72° C. for 30 seconds was carried out 15 times using N5KG2 as a template and primers linkH: gggtacgtcctcacattcagtgatcag (SEQ ID NO: 29) and UM4-2: GGCACGGTGGGCAtggggggaccataTTTGCGCTC (SEQ ID NO: 30). At the same time, reaction at 98° C. for 1 second, at 60° C. for 30 seconds and at 72° C. for 30 seconds was carried out 15 times using N5KG2 as a template and primers UM4-1: GAGCGCAAAtatggtcccccaTGCCCACCGTGCC (SEQ ID NO: 31) and linkH2: tgatcatacgtagatatcacggc (SEQ ID NO: 32). The amplified DNA fragments were purified using a PCR purification kit, and the same amounts of the two purified DNA fragments were mixed. Thereafter, reaction at 98° C. for 1 second, at 60° C. for 30 seconds and at 72° C. for 30 seconds was carried out five times. Primers linkH and linkH2 were added to the mixture, and the same reaction was carried out 15 times. The amplified DNA fragment was cleaved with NheI and BamHI, and substituted with the IgG1 constant region of the N5KG1vector.

N5KG2LH4 was prepared as follows. Reaction at 98° C. for 4 second, at 60° C. for 30 seconds and at 72° C. for 30 seconds was carried out 15 times using N5KG2 as a template and primers linkH: gggtacgtcctcacattcagtgatcag (SEQ ID NO: 33) and UL4-2: GAAGACTGACGGTCCccccaggaactcTGGTGCTGGGCA (SEQ ID NO: 34). At the same time, reaction at 98° C. for 1 second, at 60° C. for 30 seconds and at 72° C. for 30 seconds carried out 15 times using N5KG2 as a template and primers UL4-1: TGCCCAGCACCAgagttcctggggGGACCGTCAGTCTTC (SEQ ID NO: 35) and linkH2: tgatcatacgtagatatcacggc (SEQ ID NO: 36). The amplified DNA fragments were purified using a PCR purification kit, and the same amounts of the two purified DNA fragments were mixed. Thereafter, reaction at 98° C. for 1 second, at 60° C. for 30 seconds and at 72° C. for 30 seconds was carried out five times. Primers linkH and linkH2 were added to the mixture, and the same reaction was carried out 15 times. The amplified DNA fragment was cleaved with NheI and BamHI, and substituted with the IgG1 constant region of the N5KG1 vector.

The three respective domain swap mutants of the KM341-1-19 antibody and the 2105 antibody were examined to have the same binding activity to an antigen (FIGS. 6A-1 and 6A-2). However, IgG2UH4 and IgG2MH4 exhibited significantly reduced agonistic activity to Ramos cells (FIGS. 6B-1 and 6B-2). It was found from the above that the structures of upper hinge and middle hinge in the hinge region are important for IgG2 subclass-dependent agonistic activity of the anti-CD40 antibodies KM341-1-19 and 2105.

Figure 7B:
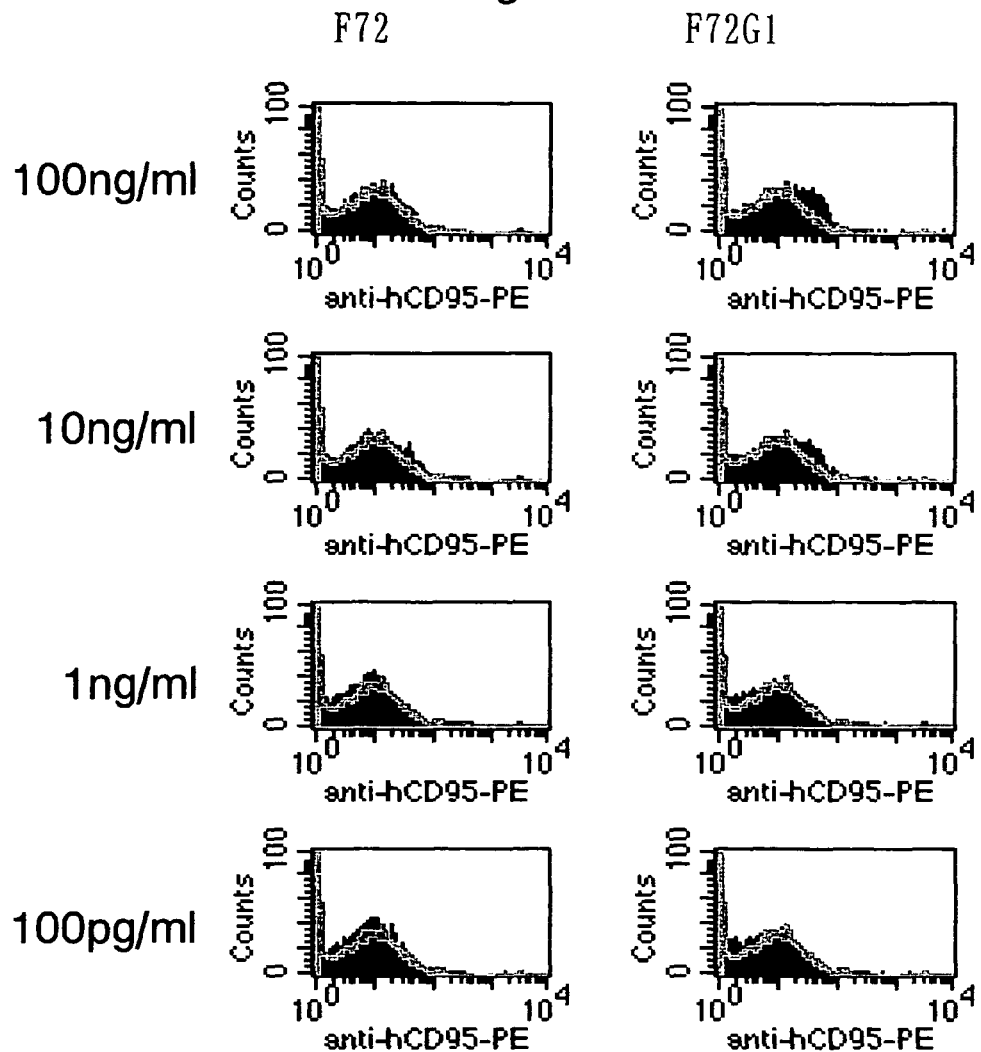
FIG. 7B shows diagrams indicating that conversion of the subclass of the F72 antibody to IgG2 raises an activity to enhance CD95 expression of Ramos cells.

Since IgG2 subclass was found to be important for agonistic activity, antibodies of subclass other than IgG2 were converted to those of IgG2 subclass to examine whether or not the agonistic activity was enhanced. In the examination on several clones, agonistic activity of F76 could be enhanced by converting IgG1 subclass to IgG2 subclass (FIGS. 7A and B).

EXAMPLE 11

Preparation of Anti-CD40 Antagonist Antibody Mutants

Figure 8A:
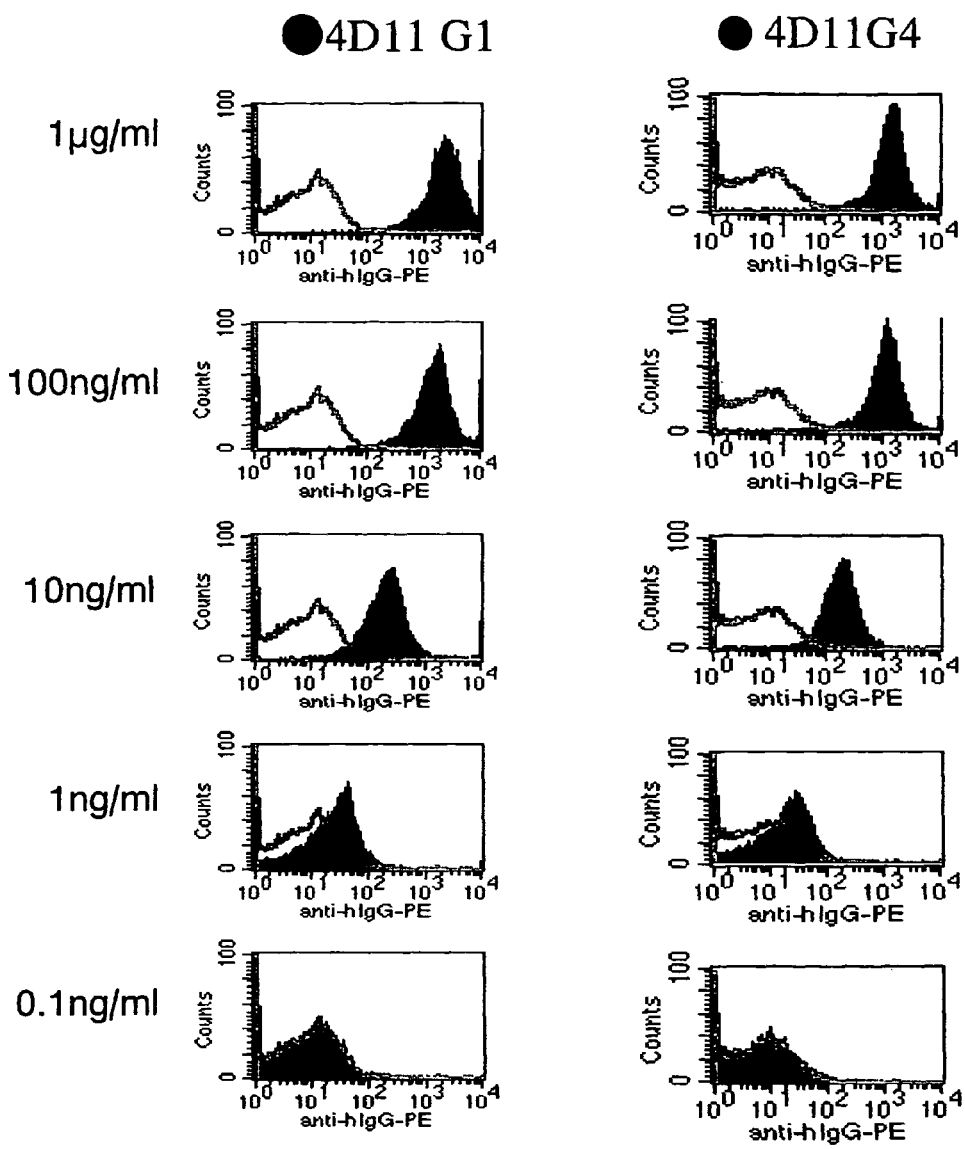
FIG. 8A shows diagrams indicating that conversion of the subclass of the 4D11 antibody from IgGI to IgG4 has no effect on its binding to Ramos cells.
Figure 8B:
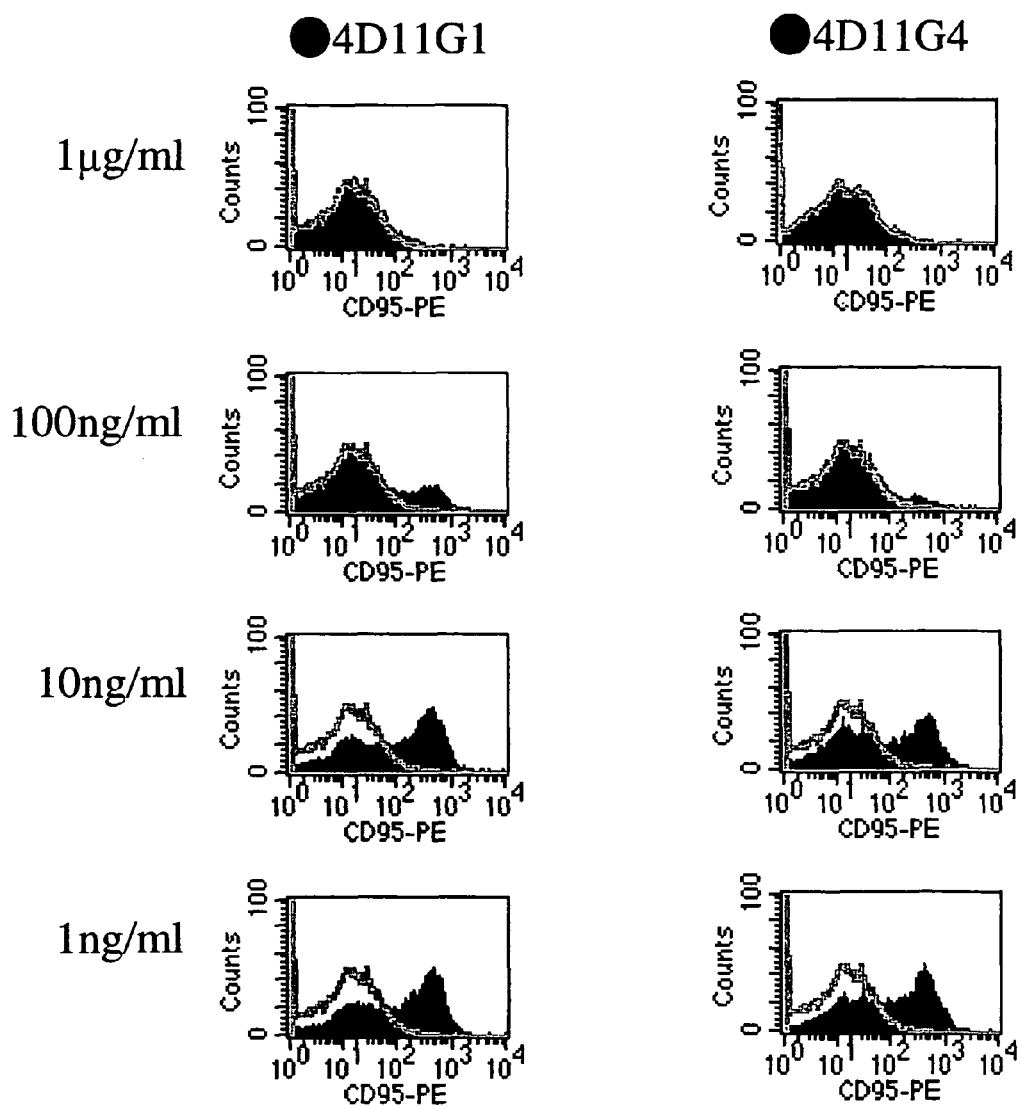
FIG. 8B shows diagrams indicating that conversion of the subclass of the 4D11 antibody from IgGI to IgG4 inhibits enhancement by the CD4OLigand of CD95 expression of Ramos cells, at the same extent as otherwise.

A DNA fragment containing a heavy chain and a light chain of a 4D11 antibody gene described in WO 02/088186, whose original subclass is IgG1, was digested with BglII and NheI, purified, and then integrated into N5KG4PE, N5KG4P and N5KG4 vectors (IDEC Pharmaceuticals). N5KG4PE contains point mutations S228P and L235E in the IgG4 constant region, and N5KG4P contains a point mutation S228P in the IgG4 constant region. The antibody protein was expressed and purified according to the above method. The antibody was purified according to the above method using binding to Ramos cells as an index. Change in binding activity of IgG1, IgG4, IgG4P and IgG4PE to Ramos cells was not observed (FIG. 8A). Antagonistic activity of IgG1 was compared with those of various IgG4 mutants according to the above method to find that antagonistic activity of IgG1 does not differ from those of the IgG4 mutants (FIG. 8B).

EXAMPLE 12

Evaluation of ADCC Activity and CDC Activity of Anti-CD40 Antagonist Antibody Mutants ADCC activity and CDC activity of anti-CD40 mutant antibodies were evaluated according to the above method.

Figure 9:
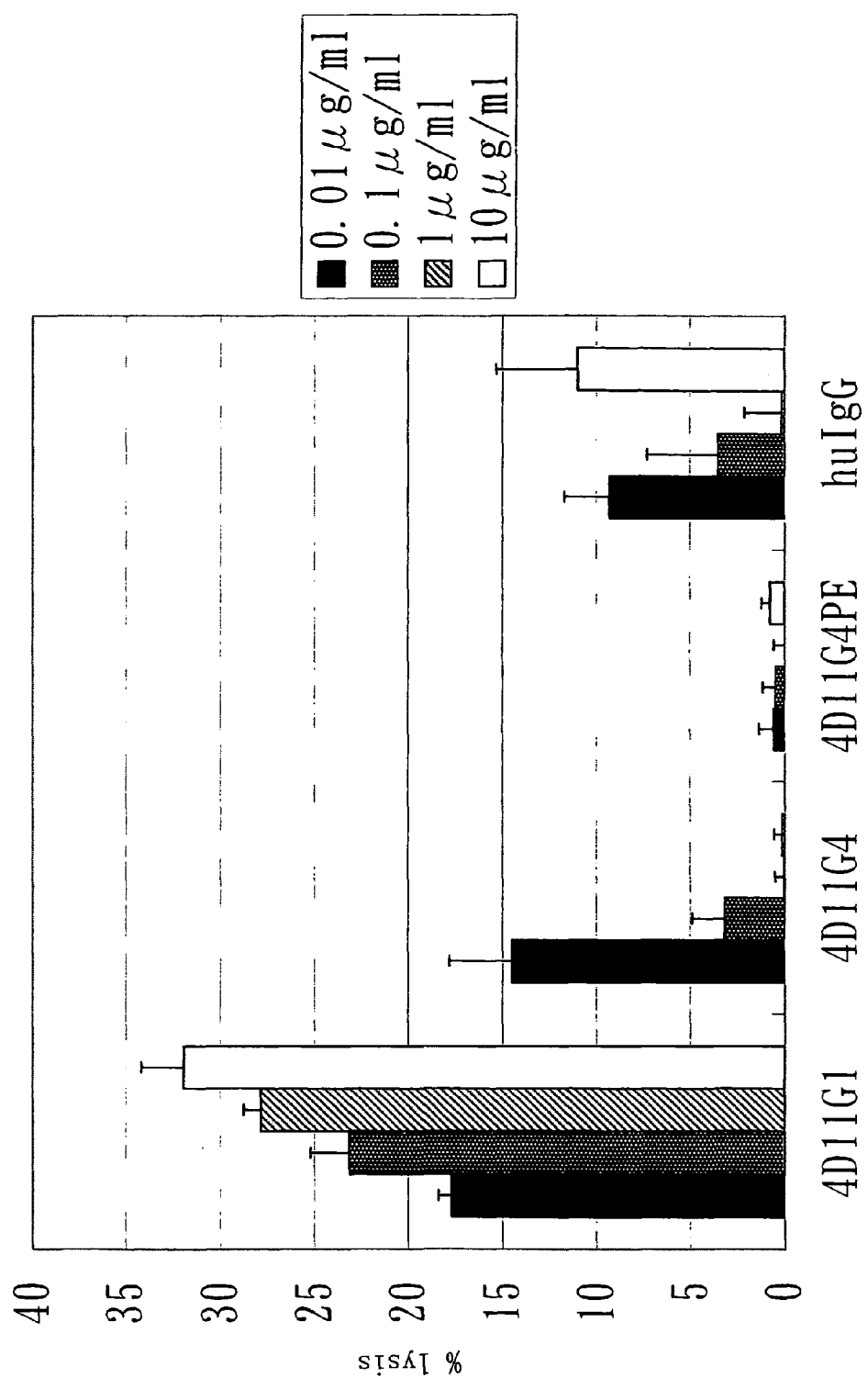
FIG. 9 shows a diagram indicating that conversion of the subclass of the 4D11 antibody from IgGI to IgG4 or IgG4PE lowers the ADCC activity.

When using human MNC as effector cells and CD40-expressing Daudi cells as target cells, two mutants IgG4 and IgG4PE were respectively observed to have ADCC activity significantly reduced as compared with IgG1 as the original subclass of the 4D11 antibody (FIG. 9).

Figure 10:
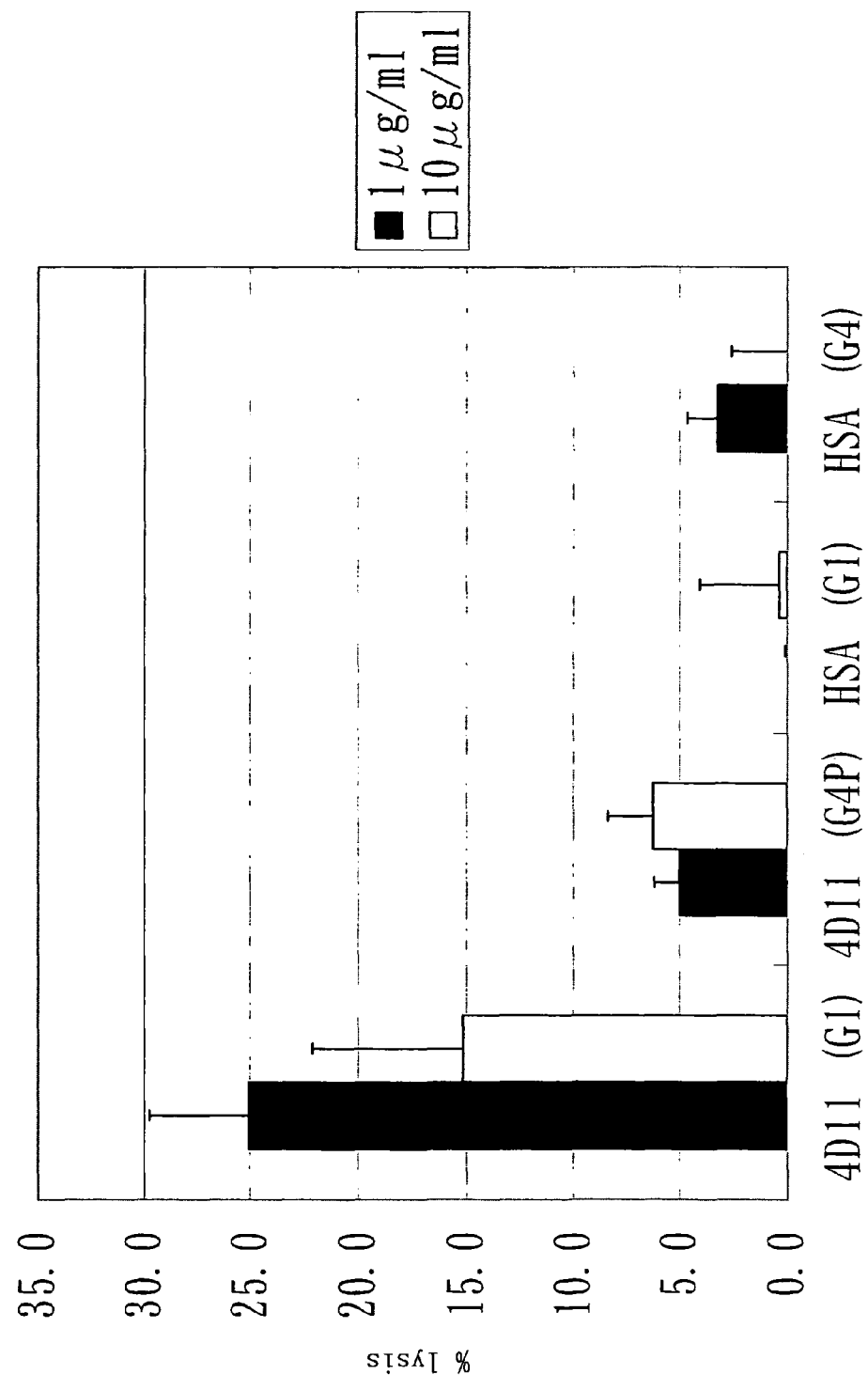
FIG. 10 shows a diagram indicating that conversion of the subclass of the 4D11 antibody from IgGI to IgG4P lowers the CDC activity.

CDC activity of IgG1 was compared with that of IgG4P using Daudi cells as target cells. IgG4P was found to have CDC activity significantly reduced as compared with IgG1 (FIG. 10).

EXAMPLE 13

Effect of Anti-CD40 Antagonistic Antibody on B Cells

Figure 11:
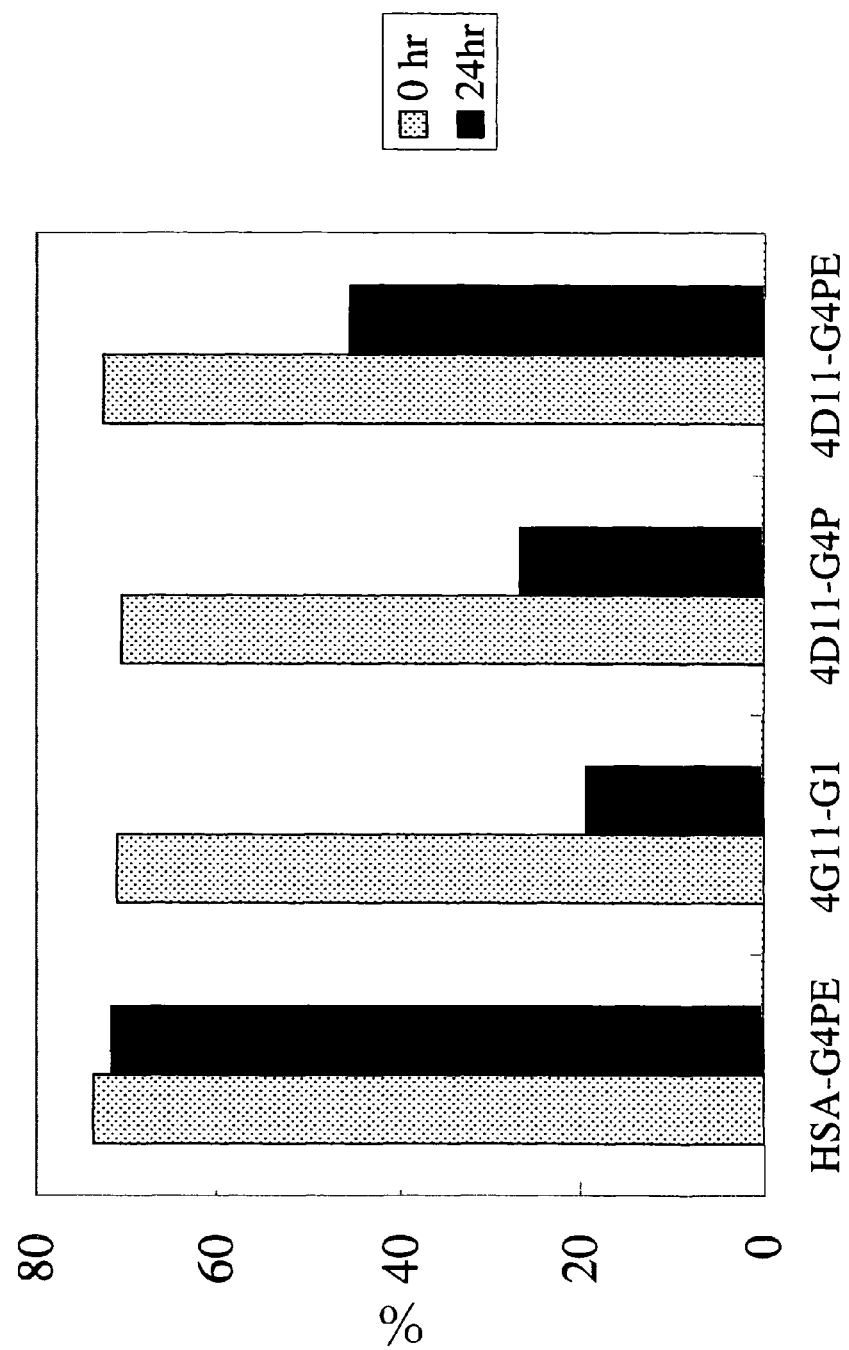
FIG. 11 illustrates a variation in number of B cells in the blood (B220-positive cells among the peripheral blood lymphocytes) over time after 4D11G1, 4D11G4P or 4D11G4PE was administered into human CD40-transgenic mice.
Figure 12A:
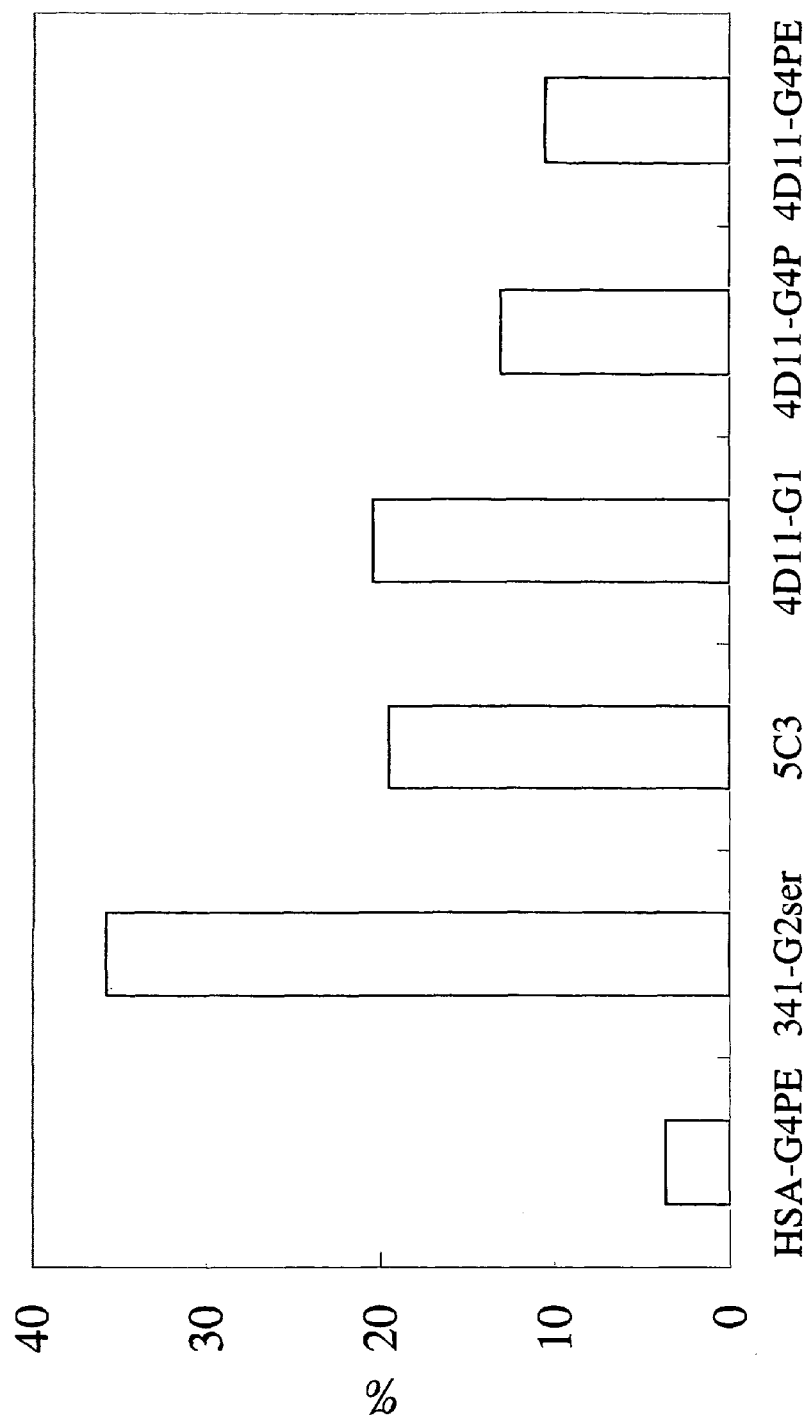
FIG. 12A illustrates a higher expression of CD23 of splenic B cells (CD23-positive cells among the splenic B cells) after each anti-CD40 antibody was administered into human CD40-transgenic mice.
Figure 12B:
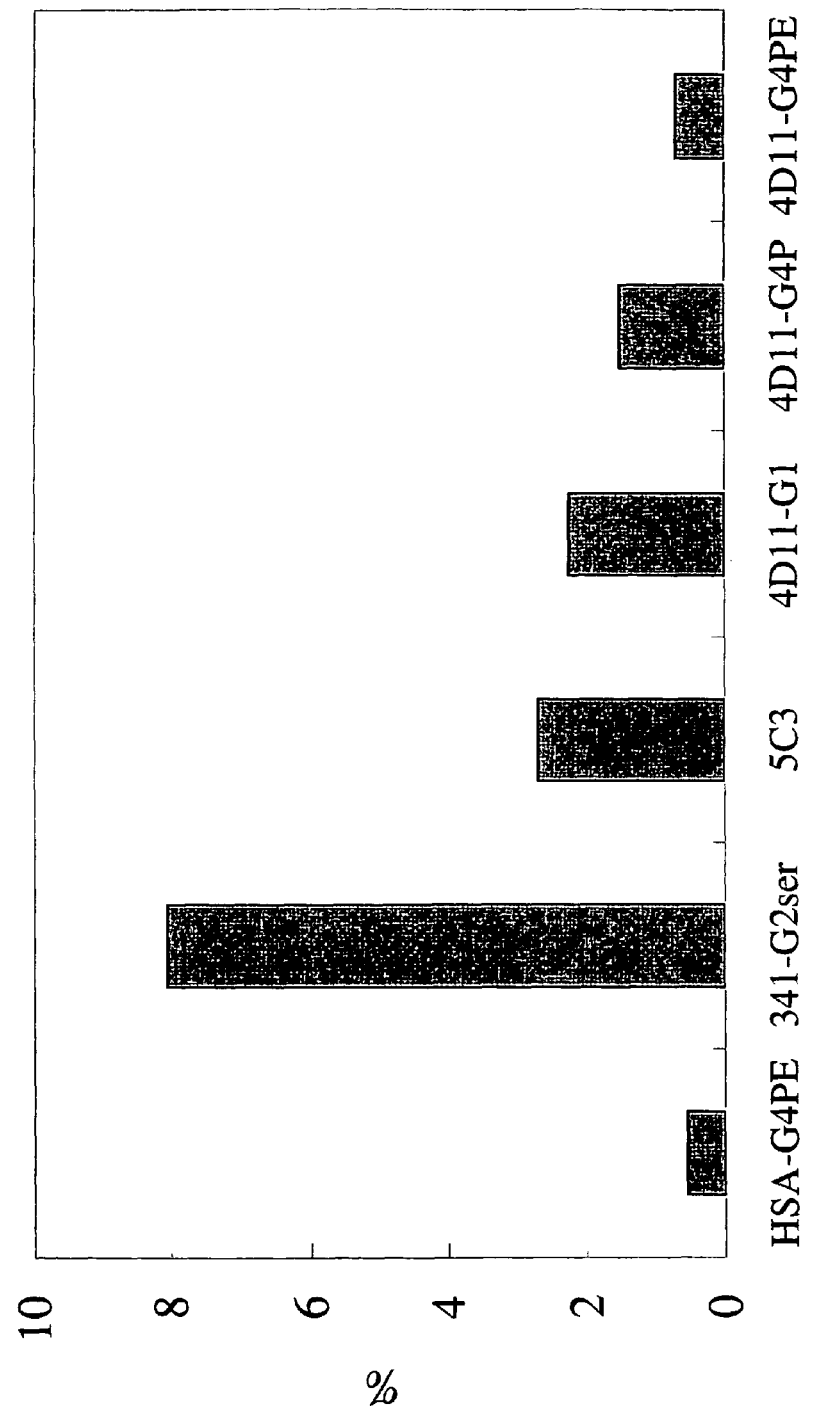
FIG. 12B illustrates a higher expression of CD86 of splenic B cells (CD86-positive cells among the splenic B cells) after each anti-CD40 antibody was administered into human CD40-transgenic mice.
Figure 12C:
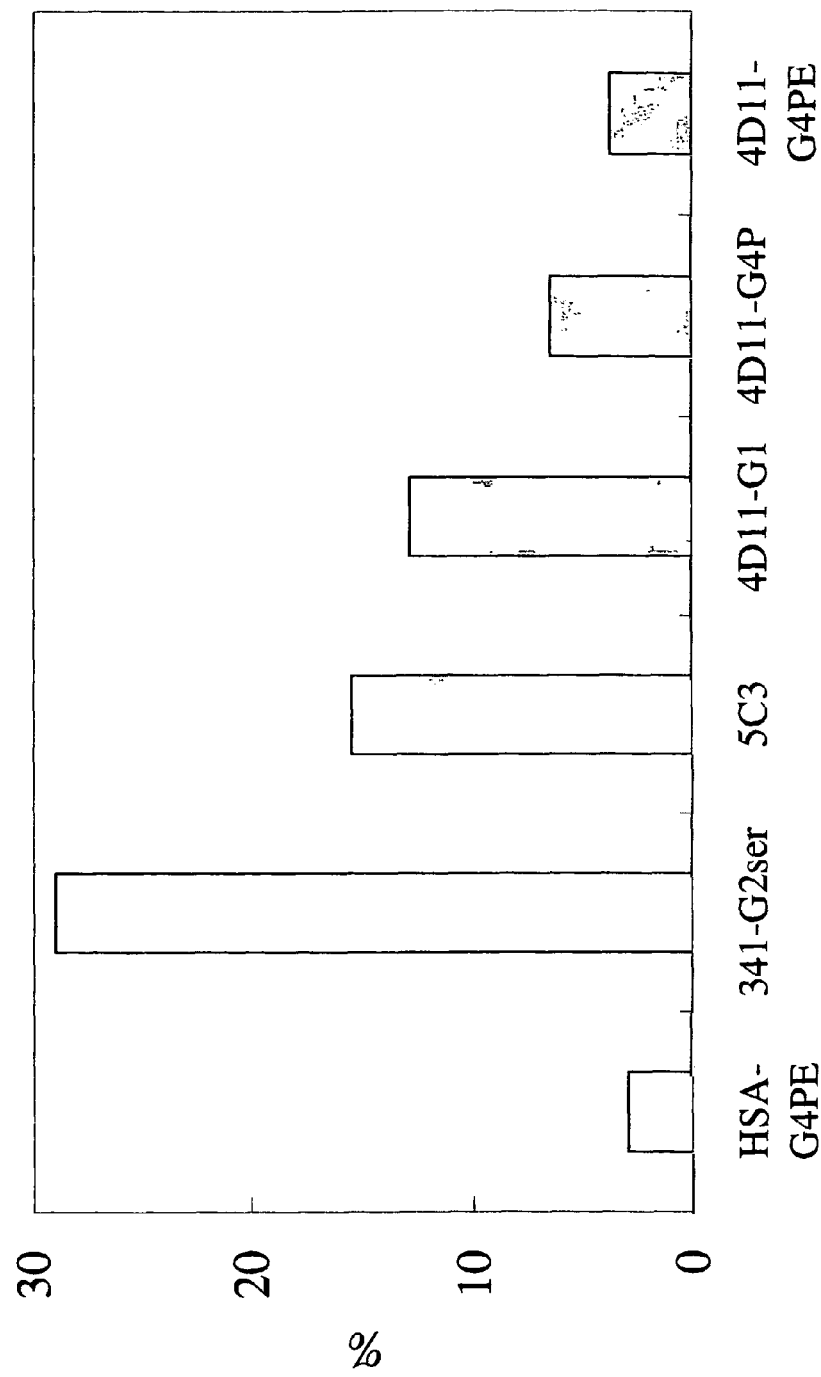
FIG. 12C illustrates a higher expression of CD95 of splenic B cells (CD95-positive cells among the splenic B cells) after each anti-CD40 antibody was administered into human CD40-transgenic mice.

100 μg each of IgG1, IgG4P and IgG4PE of the 4D11 antibody was administered to the tail vein of mice having a genetic background whereby they were homozygotes for mouse endogenous disrupted CD40 and harboring a transgene of a human CD40 gene (Yasui. et al. Int. Immunol. 2002 Vol 14: 319). 24 hours after the administration, blood was collected from the orbital venous plexus. After hemolysis with 0.16 mol/L of ammonium chloride, an FITC-labeled anti-B220 antibody was added to the hemolysate, and it was analyzed using FACS. The results are shown in FIG. 11. In the figure, the longitudinal axis indicates the ratio of B cells in the total lymphocytes. IgG1 reduced the ratio of B cells most, IgG4P reduced the ratio to a lesser extent, and IgG4PE reduced the ratio to a much lesser extent. 24 hours after the administration, the spleen was removed and crushed with a slide glass to prepare a cell suspension. After hemolysis of the cell suspension, a PE-labeled anti-B220 antibody and an FITC-labeled anti-CD23, CD86 or CD95 antibody were used for the hemolysate, and it was analyzed using FACS. The results are shown in FIGS. 12A, B and C. In the figures, the longitudinal axis indicates the ratio of B cells expressing each surface marker in the total lymphocytes. 4D11G1 was found to achieve the same level of increase in expression of each marker as in a commercially available mouse anti-human CD40 agonistic antibody 5C3 (Pharmingen). IgG4PE achieved a smaller increase in expression of each activation surface marker as compared with IgG1 and IgG4P.

EXAMPLE 14

Figure 13A:
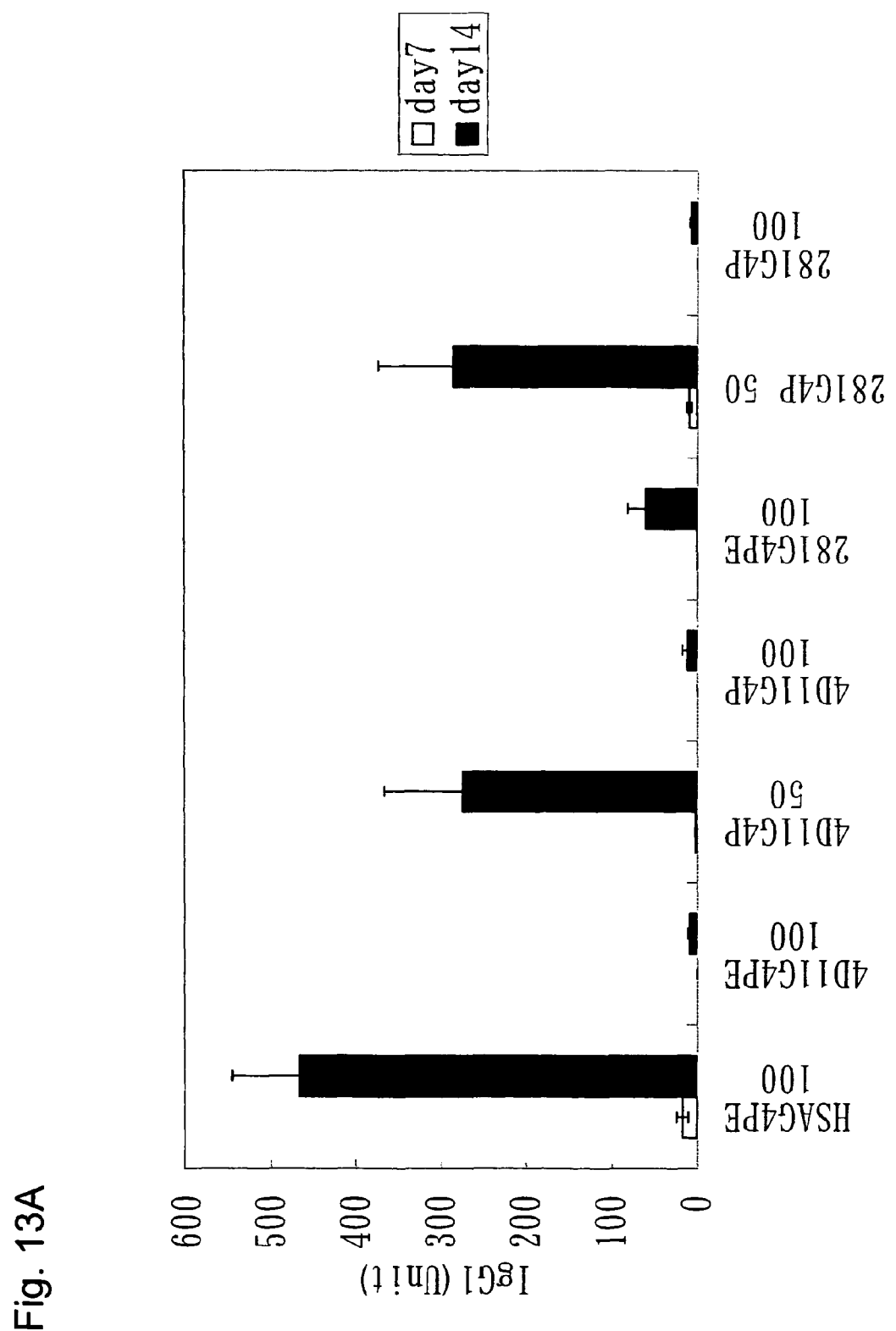
FIG. 13A illustrates the suppressive activity of the antigen-specific antibody (IgG1) production by 4D11 and 281-1-10 in human CD40-transgenic mice.
Figure 13B:
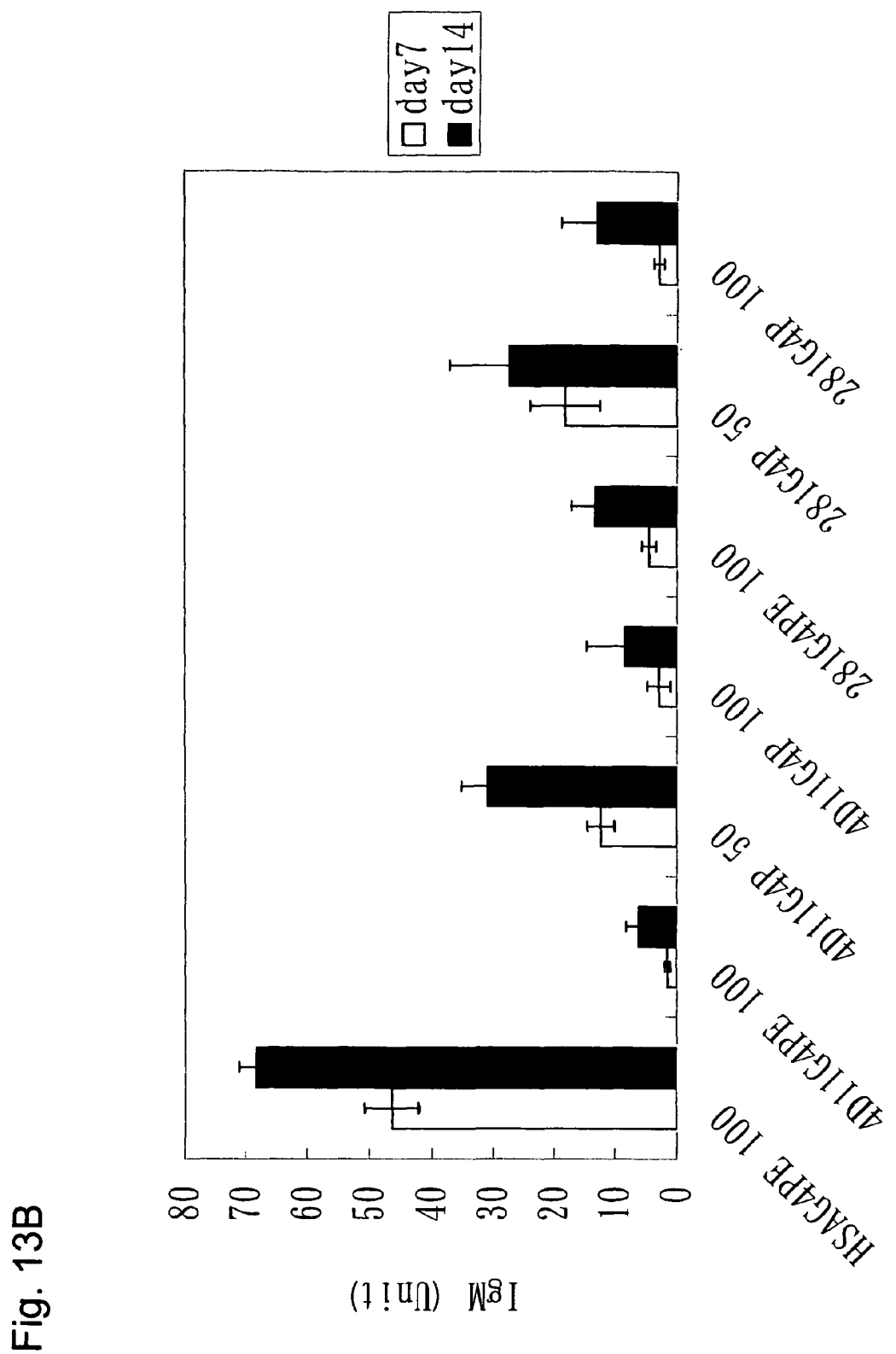
FIG. 13B illustrates the suppressive activity of the antigen-specific antibody (IgM) production by 4D11 and 281-1-10 in human CD40-transgenic mice.

Effect of Inhibiting Production of Antigen-Specific Antibody and Change In the Number of B Cells Caused by Anti-CD40 Antagonistic Antibody 100 μg (based on NP-CGG) of a complex of 4-hydroxy-3-nitrophenylacetyl-chiken γ-globulin conjugates (NP-CGG: distributed by Professor Hitoshi KIKUTANI, Research Institute for Microbial Diseases, Osaka University) and alum (aluminum hydroxide gel) was intraperitoneally administered to mice having a genetic background whereby they were homozygotes for mouse endogenous disrupted CD40 and harboring a transgene of a human CD40 gene (Yasui et al. Int. Immunol. 2002 Vol 14: 319) to sensitize the mice. Immediately before the antigen sensitization, 50 or 100 μg of each antibody was administered to the tail vein. 100 μg of an anti-human albumin human IgG4PE antibody was administered as a negative control. 7 and 14 days after the sensitization, blood was collected from the orbital venous plexus. The amounts of NP-specific IgG1 and IgM antibodies in the serum were measured by the ELISA method. The ELISA method was carried out as follows. 50 μl/well of NP-bound bovine serum albumin (NP-BSA: 2.5 μg/ml) was added to each well of a 96-well inicroplate for ELISA (Maxisorp, manufactured by Nunc A/S) and incubated at 4° C. to cause NP-BSA to be adsorbed thereon. Next, the supernatant was discarded, and a blocking reagent (SuperBlock, manufactured by Pierce Biotechnology, Inc.) was added to each well and incubated at room temperature to carry out blocking. Then, each well was washed with a phosphate buffer (PBS-T) containing 0.1% Tween 20 three times. Next, each serum diluted with PBS-T containing 10% Block Ace (50 μl/well) was added to each well, and incubated and reacted at 37° C. for two hours. The microplate was washed with PBS-T three times. Then, a 1,000-fold dilution of a goat anti-mouse IgG1 antibody or IgM antibody labeled with alkaline phosphatase (Cosmo Bio, 1070-04 or 1020-04) with PBS-T containing 10% Block Ace (50 μg/well) was added to each well, and incubated at 37° C. for two hours. Next, the microplate was washed with PBS-T, and then a coloring substrate solution (50 μl/well, Sigma 104, phosphatase substrate) was added to each well. The absorbance at a wavelength of 405 nm was measured using a microplate reader. The results are shown in FIGS. 13A and B. In the figures, the longitudinal axis indicates values obtained by converting a 10,000-fold dilution (in the case of IgG1) or 100-fold dilution (in the case of the IgM antibody) of serum collected from C57BL/6 mice, to which NP-CGG was injected twice, and pooled into one unit. The 4D11 antibody and the IgG4P or IgG4PE antibody of 281 inhibited production of NP-specific IgG1 and IgM antibodies equally strongly.

Figure 14A:
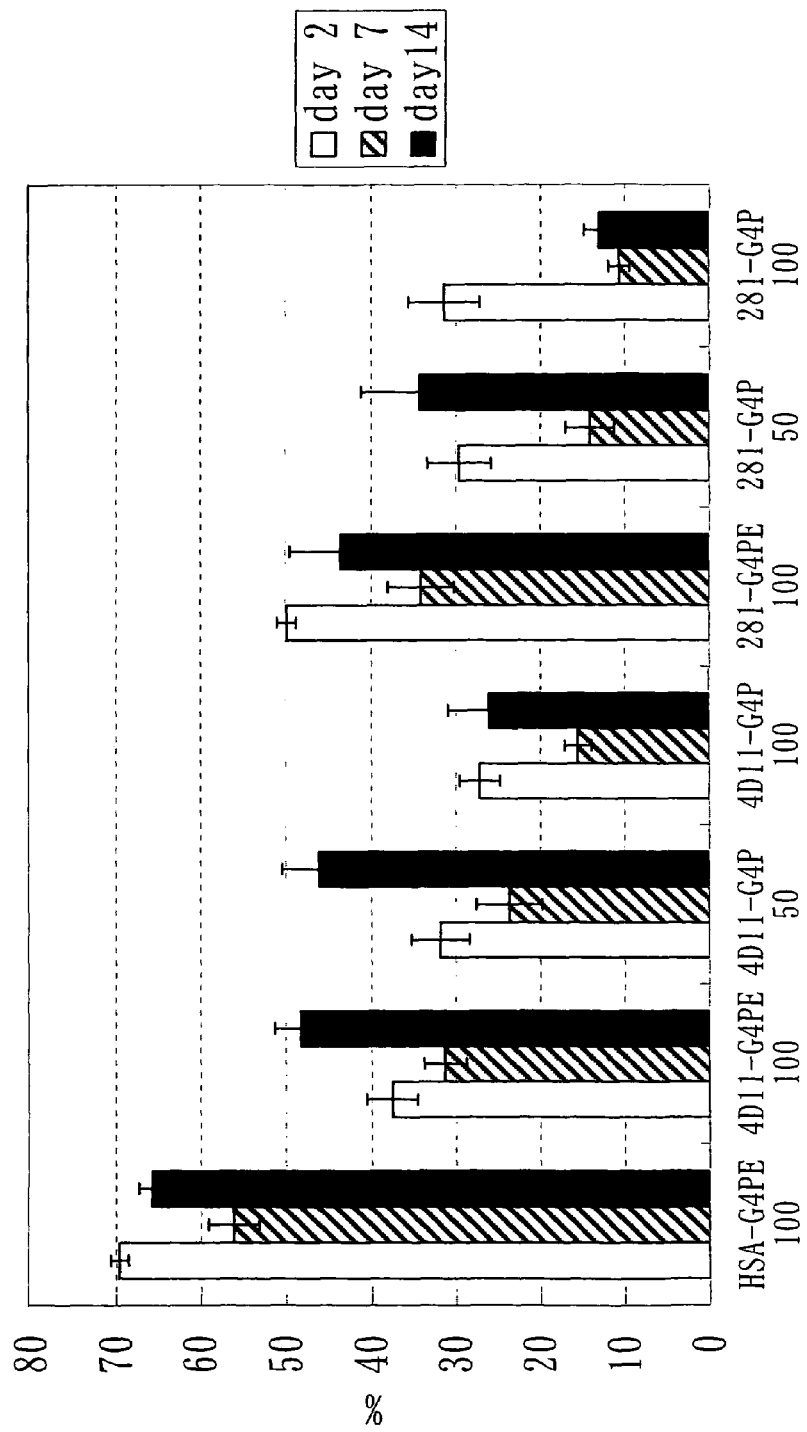
FIG. 14A illustrates the numbers of B cells in the blood (B220-positive cells among the peripheral blood lymphocytes) during the suppression assay of the antigen-specific antibody producing activity.
Figure 14B:
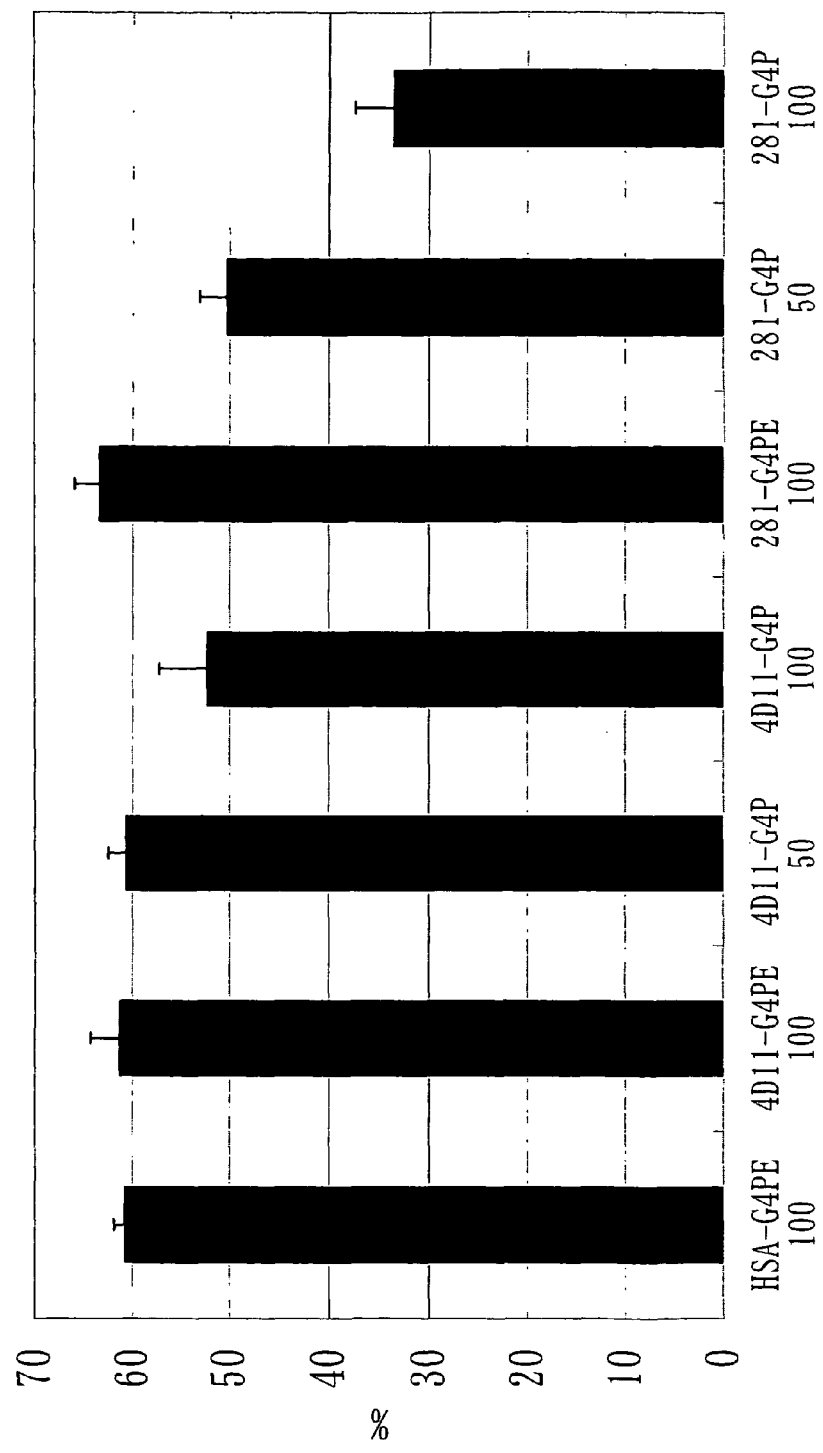
FIG. 14B illustrates the numbers of splenic B cells (B220-positive cells among the splenic lymphocytes) during the suppression assay of the antigen-specific antibody producing activity.

The change in the number of B cells in the peripheral blood and spleen in the mice used for examining the effect of inhibiting antibody production was measured according to the same method as in Example 1. The results are shown in FIGS. 14A and B. The 4D11 antibody and the IgG4P antibody of 281 reduced the ratio of B cells in peripheral blood significantly as compared with the IgG4PE antibody. Administration of 100 μg of the IgG4PE antibody did not change the ratio of B cells in the spleen removed 14 days after the antigen sensitization. However, administration of IgG4P changed or tended to change the ratio.

EXAMPLE 15

Figure 15:
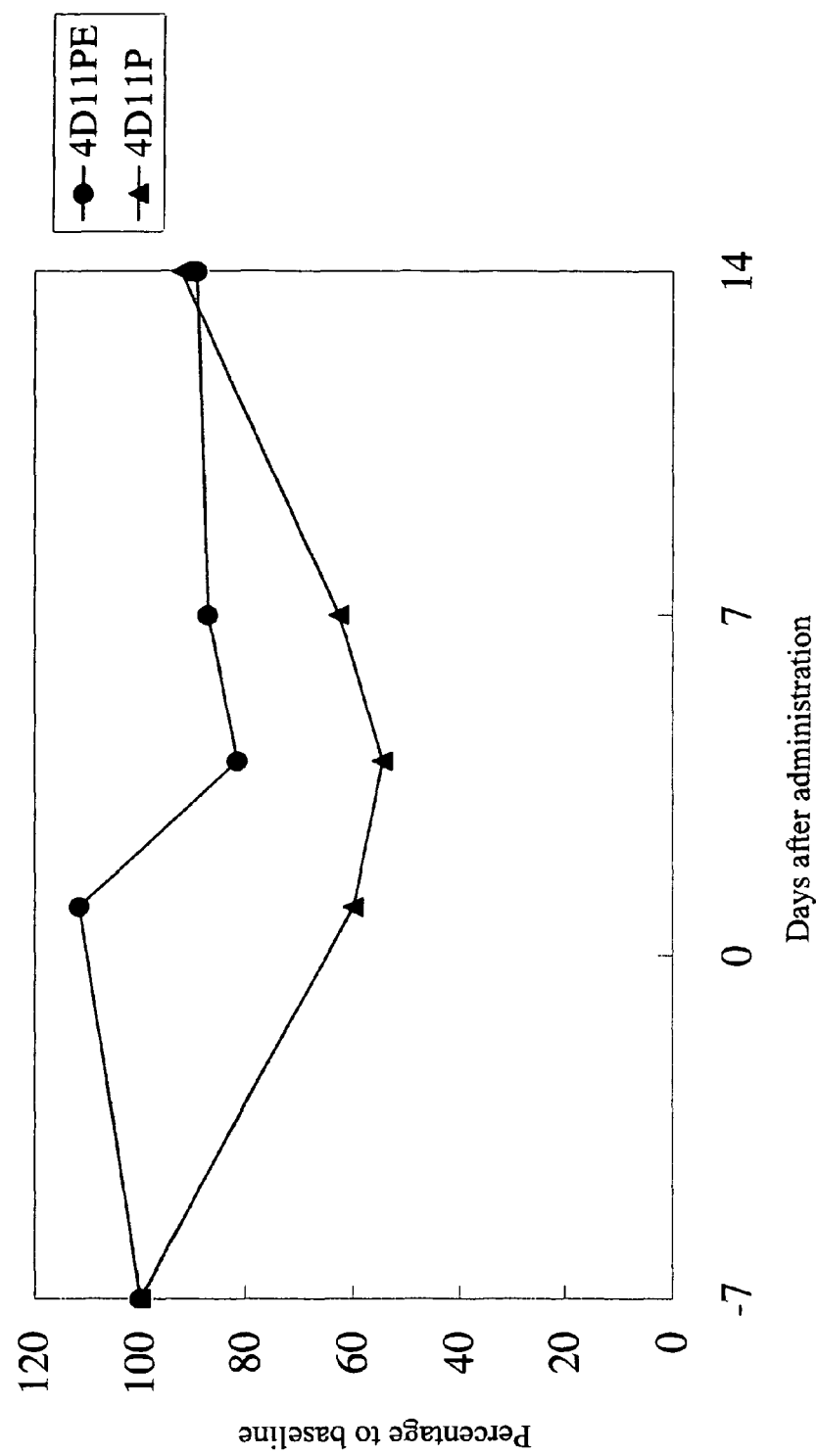
FIG. 15 illustrates a variation in number of B cells in the blood (B220-positive cells among the peripheral blood lymphocytes) over time after 4D11G4P or 4D11G4PE was administered at a dose of 30 mg/kg into cynomolgus monkeys.

Effect of anti-CD40 Antagonistic Antibody on Cynomolgus Monkeys 30 mg/kg of IgG4P or IgG4PE of a 4D11 antibody was administered to the forearm cephalic vein of cynomolgus monkeys, and blood was collected from the femoral vein after a certain period of time. In the subset analysis of peripheral blood lymphocytes, an FITC-labeled anti-CD3 antibody, PE-labeled anti-CD20 antibody and APC-labeled anti-CD45 antibody were used for each cell suspension, and the ratio of positive cells was measured using FACS to calculate the ratio of CD45 positive cells. The results are shown in FIG. 15. In the figure, the longitudinal axis indicates the ratio of CD20 positive cells at each time to CD20 positive cells before antibody administration. 1 to 7 days after the antibody administration, CD20 positive cells were reduced by about 40% in individuals to which the IgG4P antibody was administered. However, 4 days after the administration, CD20 positive cells were reduced by only about 20% in individuals to which the IgG4PE antibody was administered.

Figure 16:
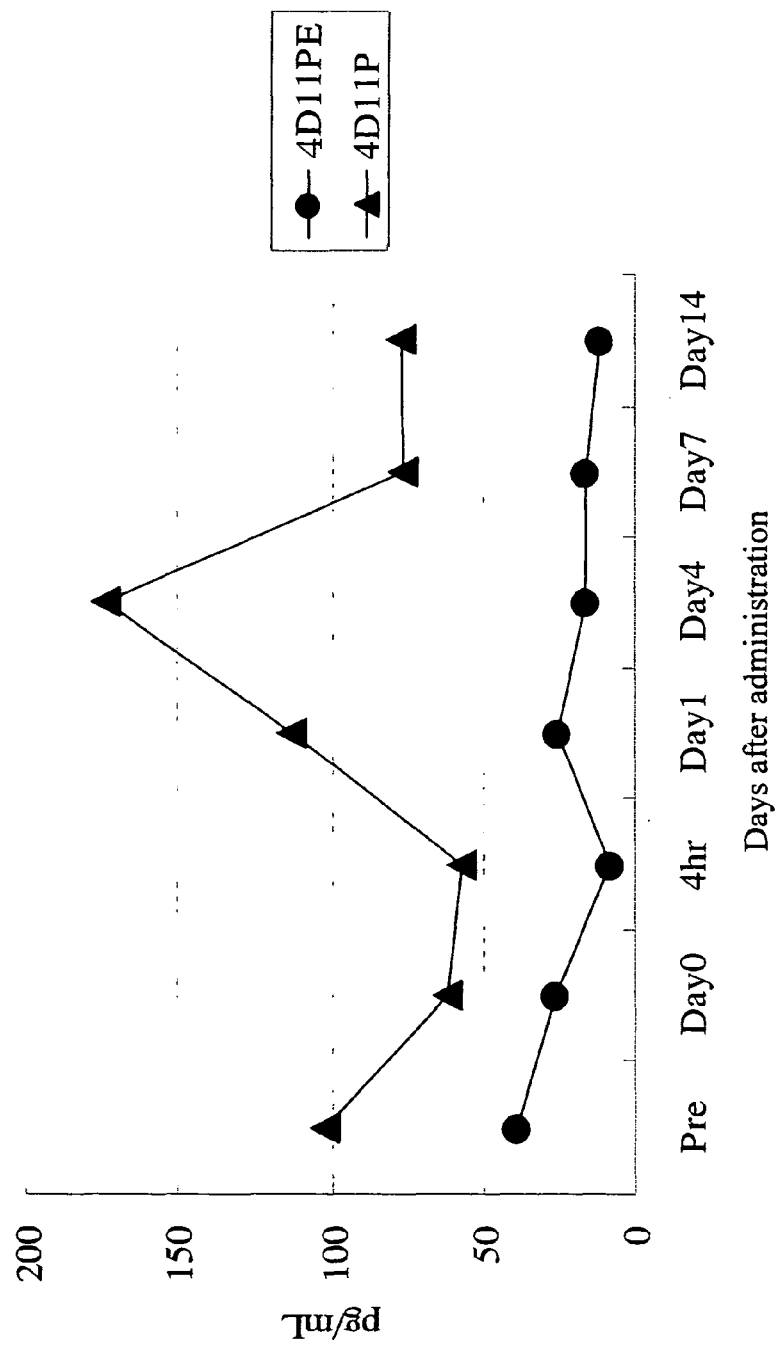
FIG. 16 illustrates blood IL-12 levels during the assay shown in FIG. 15.

The IL12 concentration in serum was measured by the ELISA method. Blood collected from the femoral vein was allowed to stand at room temperature for 20 to 60 minutes, and then centrifuged at 3,000 rpm at room temperature for 15 minutes. The IL12 concentration in the resulting serum was measured using a monkey IL12 ELISA kit (BioSource International Inc.). The results are shown in FIG. 16. No increase in IL12 production by the IgG4PE antibody was observed at any blood collection point. However, maximum IL12 production by the IgG4P antibody was observed on the 4th day.

EXAMPLE 16

Effect of Anti-CD40 Antagonistic Antibody on Cynomolgus Monkey Delayed Hypersensitivity Model Nine male cynomolgus monkeys were intradermally and intramuscularly sensitized with Tetanus toxoid (TTx) (10 Lf/ml; Denka Seiken Co., Ltd.) to induce delayed hypersensitivity to TTx. At the same time, 10 minutes before the start of sensitization, 0.1 and 10 mg/kg of a 4D11G4PE antibody was intravenously administered to each three animals three times (once a week) to examine the effect of 4D11G4PE on delayed hypersensitivity. Under anesthesia by intramuscular administration of ketamine, sensitization was carried out by intradermal administration of TTx to the back (50 µL/site×12 sites) and intramuscular administration of TTx to the femur (0.6 mL/body), and challenge was carried out by intradermal administration of TTx to the thorax (10 µL/site, 0 to 10 Lf/ml for each three sites) 21 days after the sensitization. 24 and 48 hours after the elicitation, skin reaction at the administration sites was observed and evaluated according to the Draize skin irritation score. The results of determining the TTx concentration in each three sites were respectively a mean value. The results are shown in FIG. 17. Administration of the 4D11G4PE antibody apparently inhibited the delayed hypersensitivity reaction observed 24 and 48 hours after the administration.

The effect of TTx on TTx-specific IgG and IgM antibody titers was examined. Blood collected from the femoral vein over time was allowed to stand at room temperature for 20 to 60 minutes, and then centrifuged at 3,000 rpm at room temperature for 15 minutes. The antibody titer in the resulting serum was measured using the ELISA method. The ELISA method was carried out as follows. 100 µp/well of TTx (0.5 Lf/ml) was added to each well of a 96-well microplate for ELISA (Maxisorp, manufactured by Nunc A/S) and incubated at 4° C. to cause TTx to be adsorbed thereon. Next, the supernatant was discarded, and a blocking reagent (phosphate buffer containing 0.5% BSA) was added to each well and incubated at room temperature to carry out blocking. Then, each well was washed with a phosphate buffer (PBS-T) containing 0.05% Tween 20 three times. Next, each serum diluted with PBS-T containing 0.5% BSA (100 to 819,200-fold dilution, dilution magnification: 2; 100 µl/well) was added to each well, and incubated and reacted at room temperature for two hours. The microplate was washed with PBS-T three times. Then, a 3,000-fold dilution of a goat anti-monkey IgG antibody or IgM antibody labeled with peroxidase (Nordic Immunology) with PBS-T containing 0.5% BSA (100 µg/well) was added to each well, and incubated at room temperature for one hour. Next, the microplate was washed with PBS-T, and then a coloring substrate solution (100 µl/well, o-phenylenediamine hydrochloride+aqueous hydrogen peroxide) was added to each well. The absorbance at a wavelength of 492 nm was measured using a microplate reader. The anti-TTx antibody titer was defined as a maximum dilution magnification to make the absorbance 0.1 and more. The antibody titer was 0 when the absorbance did not reach 0.1 even at 100-fold dilution. The results are shown in FIGS. 18 and 19. Administration of 1 mg/kg of 4D11G4PE suppressed the TTx-specific IgG and IgM antibody titers to about 1/10. When 10 mg/kg of 4D11G4PE was administered, the antibody titers were below the detection sensitivity at any blood collection point.

EXAMPLE 17

Effect of Anti-CD40 Antagonistic Antibody on Platelet Thrombus Formation

Figure 20B:
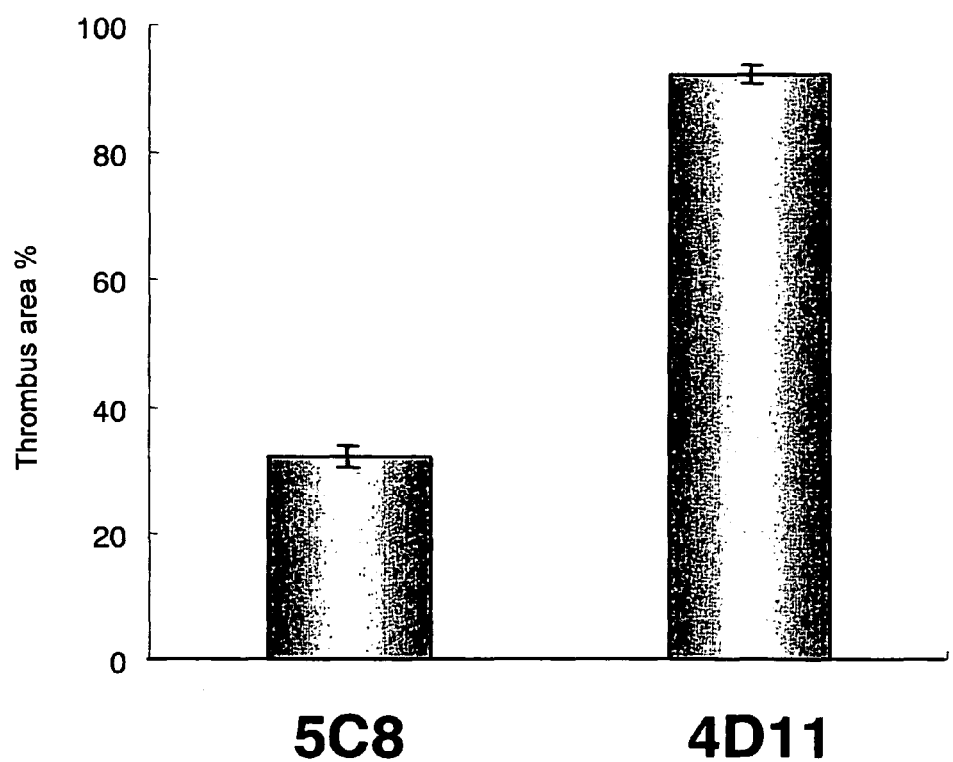
FIG. 20B shows the respective influences of 4D11G4PE and 5C8 (anti-CD4OLigand antibody) on platelet aggregation.

Blood collected from a healthy human was divided into four aliquots (each 6 ml). Control human IgG4PE, control mouse IgG2a, human anti-human CD40 IgG4PE (4D11) and mouse anti-human CD154 IgG2a (5C8) were respectively added to the fractions so that each fraction had a blood concentration of 100 µg/ml. A flat perfusion chamber (GlycoTech Corp.) and a collagen-coated Petri dish were assembled according to the attached instruction. The blood treated with various antibodies was caused to flow into the chamber at a rate that can apply a shear stress of 1,500/s to the blood for seven minutes. Thereafter, a 4% paraformaldehyde phosphate buffer was caused to flow into the chamber at a rate that can apply a shear stress of 1,500/s to the buffer for 10 minutes. The platelet aggregate formed on the Petri dish was fixed, stained with a platelet-specific PE-labeled CD41a antibody, and observed with a fluorescence microscope. The results are shown in FIGS. 20A and B. The blood treated with human anti-human CD40 IgG4PE (4D11) formed a platelet aggregate on the collagen-coated Petri dish, as the blood treated with the control antibodies did. However, the blood treated with mouse anti-human CD154 IgG2a did not form a platelet aggregate.

EXAMPLE 18

Evaluation of Stability of Anti-CD40 Antagonistic Antibody

Figure 21:
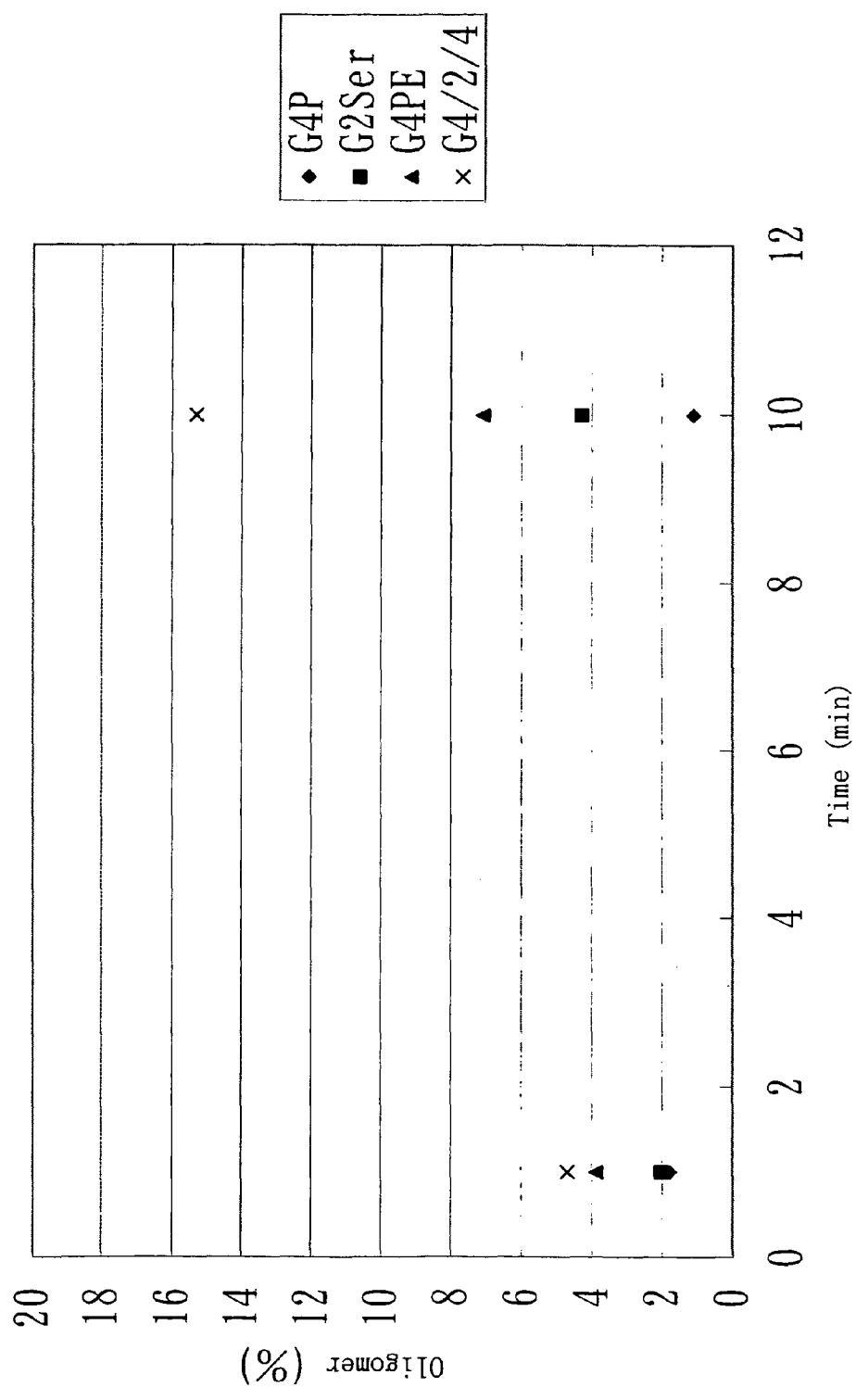
FIG. 21 illustrates a variation in oligomer content of 4D11G4P, 4D11G4PE, 4D11G2Ser or 4D11G4/2/4 over time after it was incubated at pH 2.7 and 37° C.

Constant region-modified antibodies of the 4D11 antibody were compared and examined in terms of stability. In the evaluation method, culture supernatants obtained by respectively transiently expressing G4P, G4PE, G2Ser and G4/2/4 in HEK293 cells were charged with a Protein A column (Amersham Pharmacia Biotech), eluted with a 0.1 M citrate buffer (pH 2.7), and then incubated at 37° C. for 1 minute and 10 minutes. Thereafter, they are neutralized with a 50 nM phosphate buffer (pH 7.0). The oligomer content in the resulting antibody solutions was measured using a gel filtration column (Tosoh Corp.). As a result, it was found that the oligomer content increases in proportion with the incubation time, and G4/2/4 produces an oligomer easiest, G4PE second easiest, G2Ser third easiest, and G4P fourth easiest (FIG. 21).

EXAMPLE 19

Effect of Inhibiting Skin Graft Rejection by Anti-CD40 Antagonistic Antibody

Figure 22:
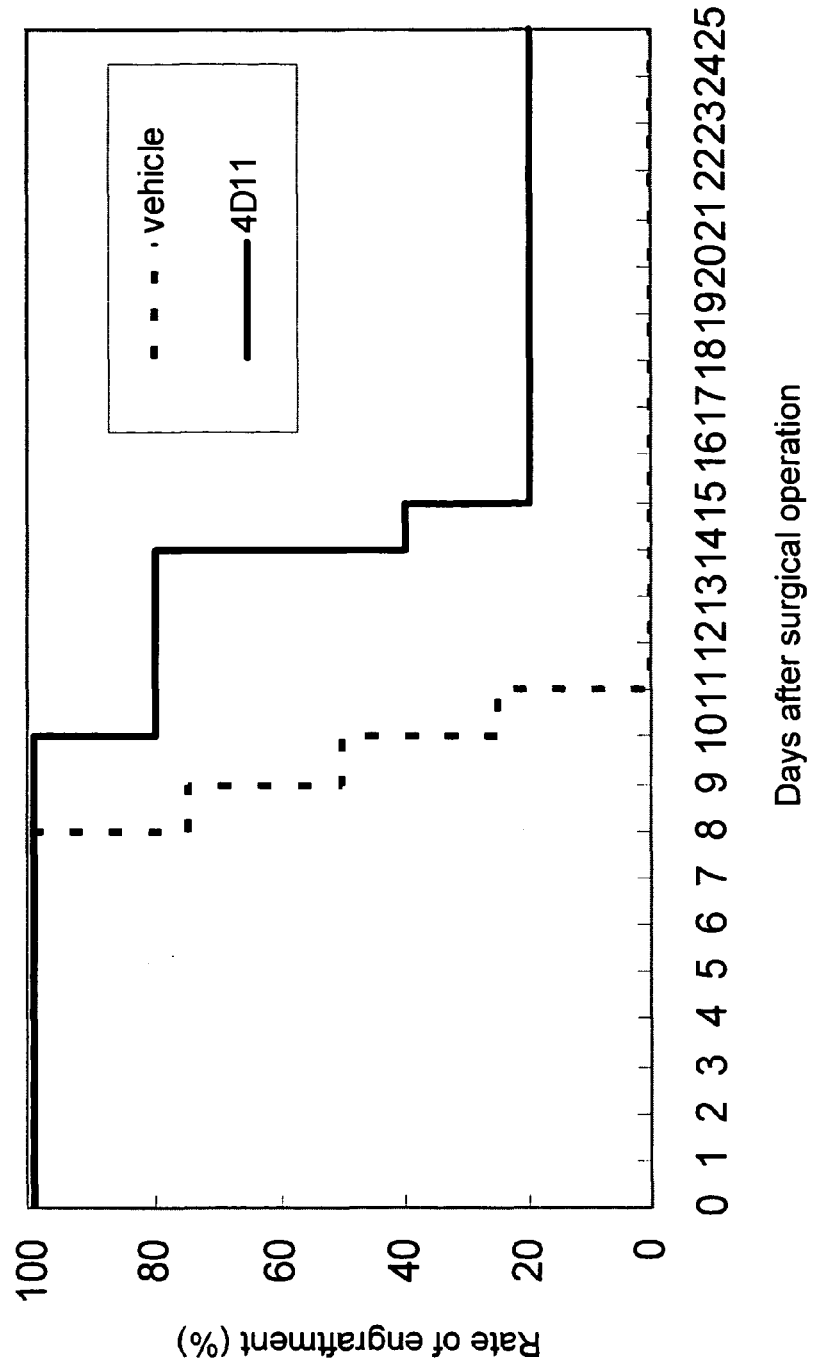
FIG. 22 illustrates suppression of rejection of skin grafts by the anti-CD40 antagonistic antibody.
Figure 23:
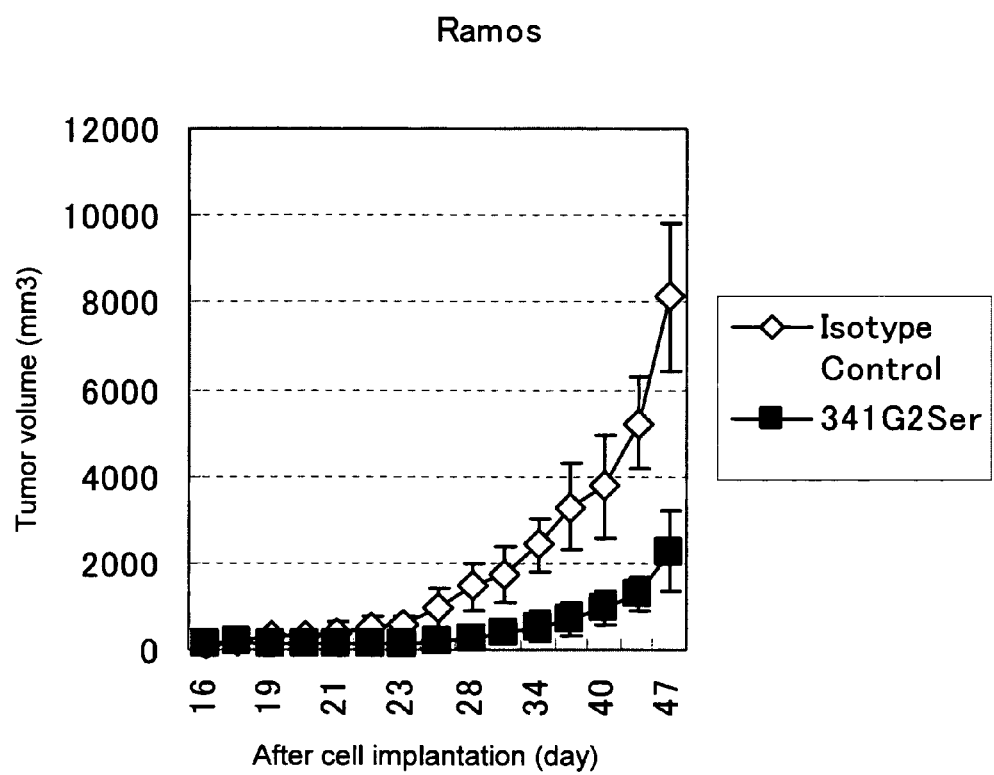
FIG. 23 illustrates the volume change of the tumor over time from cell implantation, in a case where 341G2Ser was administered to tumor bearing mice with Ramos cells implanted therein.
Figure 24:
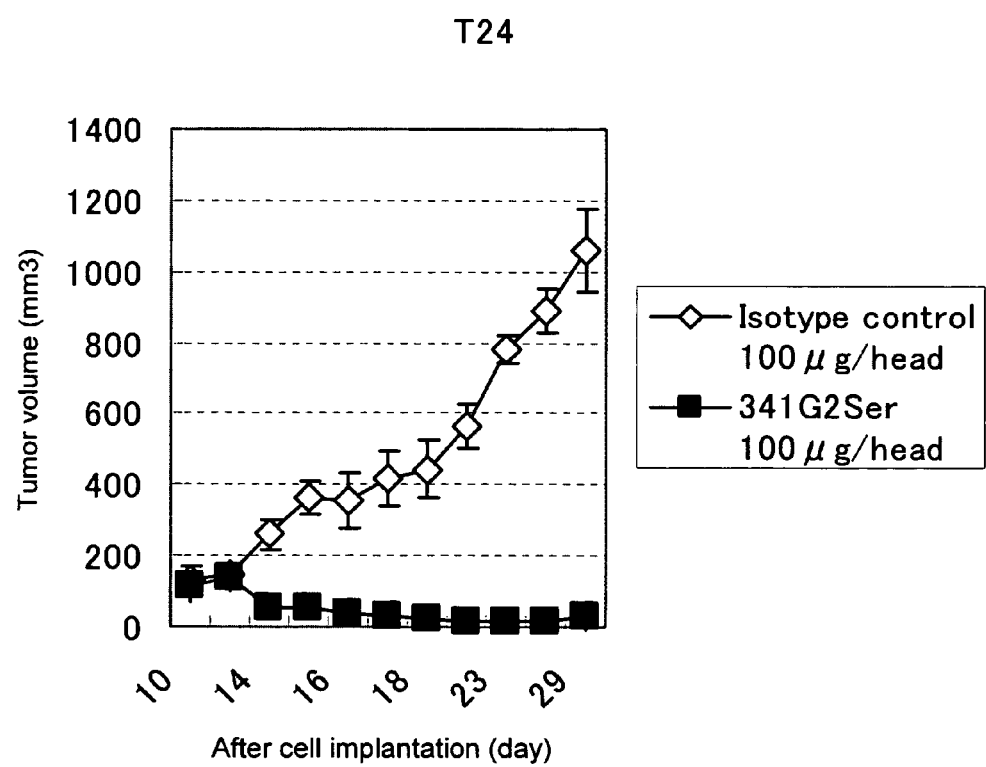
FIG. 24 illustrates the volume change of the tumor over time from cell implantation, in a case where 341G2Ser was administered to tumor bearing mice with T24 cells implanted therein.
Figure 25:
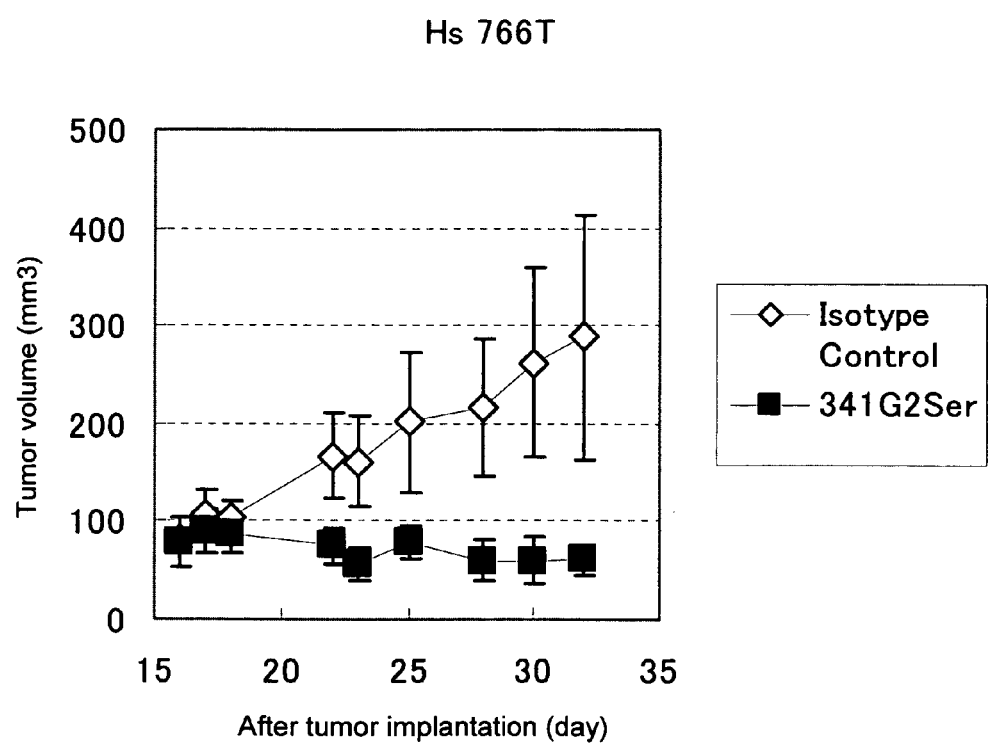
FIG. 25 illustrates the volume change of the tumor over time from cell implantation, in a case where 341G2Ser was administered to tumor bearing mice with Hs 766T cells implanted therein.
Figure 26:
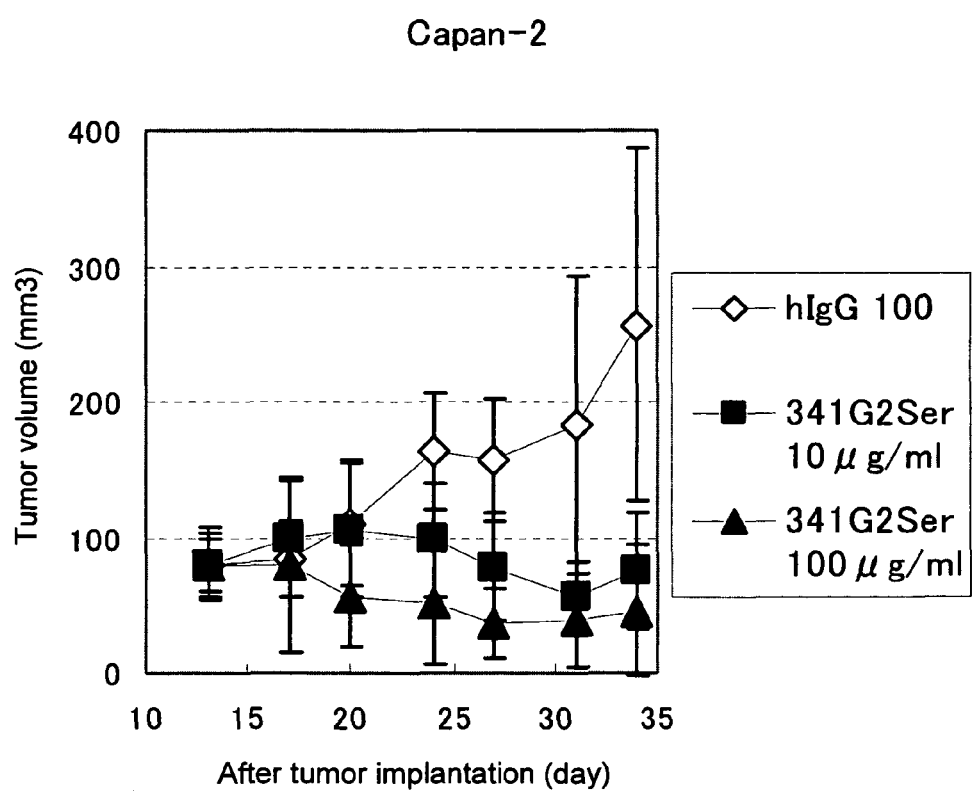
FIG. 26 illustrates the volume change of the tumor over time from cell implantation, in a case where 341G2Ser was administered to tumor bearing mice with Capan-2 cells implanted therein.

A graft collected from the tail of DBA/2 mice was grafted into the side dorsal thorax of C57BL/6 background mice having a genetic background whereby they were homozygotes for mouse endogenous disrupted CD40 and harboring a transgene of a human CD40 gene, and the graft was fixed with a plaster for seven days. 100 µg of a test substance 4D11G4PE or a vehicle was administered to the tail vein 0, 2, 4, 7, 9, 11 and 14 days after the skin graft, respectively. To inhibit graft rejection by NK cells, 100 µg of an anti-asialo GML antibody was intraperitoneally administered to all mice 3 days before the operation and 1, 4 and 9 days after the operation. The results are shown in FIG. 22. The delay in graft rejection was observed to be significant in the 4D11G4PE-administered group as compared with the vehicle-administered group.

EXAMPLE 20

Analysis of CD40 Expression in Human Tumor Cell Lines

Expression of CD40 in a Burkitt's lymphoma cell line Ramos, bladder cancer cell line T24 (ATCC, HTB-4), pancreatic cancer cell line Hs 766T (ATCC, HTB-134) and Capan-2 (ATCC, HTB-80) was confirmed by FACS analysis using 341G2Ser.

T24, Hs 766T and Capan-2 were digested with trypsin and harvested, and Ramos was harvested as is. The cell lines were washed with PBS, and then re-suspended in a staining buffer containing 1 µg/ml of 341G2Ser. The staining buffer was prepared by adding 0.05 mM EDTA, 0.05% sodium azide and 5% immobilized bovine serum to PBS. After incubation at 4° C. for 15 minutes, the cells were washed with the staining buffer twice, and re-suspended in a 1:250 dilution of PE-bound goat anti-human IgG (γ) (Southern Biotechnology Associates, Inc) with the staining buffer. After incubation at 4° C. for 15 minutes, the cells were washed with the staining buffer twice, and analyzed with FACSCalibur™ (manufactured by BD Biosciences). The same amount of a human anti-2,4-dinitrophenol (DNP) antibody was used as a negative control. The analysis was carried out using Cellquest™ (manufactured by BD Biosciences) as data analysis software to calculate the mean fluorescence intensity.

As a result, Ramos, T24, Hs766T and Capan-2 had a mean fluorescence intensity obviously higher than that of the negative control when stained with 341G2Ser, and thus expression of CD40 was confirmed.

EXAMPLE 21

Effect of Anti-CD40 Agonistic Antibody on Human Tumor Cell Lines $2.5 \times 10^3$ Ramos cells, $2.5 \times 10^2$ T24 cells, $5 \times 10^3$ Hs766T cells and $5 \times 10^3$ Capan-2 cells were respectively suspended in a medium to make the total volume of 100 µL in a flat bottom 96-well plate (manufactured by Falcon). Ramos and Hs766T, Capan-2 and T24 were cultured for 66 hours, 90 hours and 114 hours, respectively, together with 341G2Ser at a concentration of 1 ng/ml to 1,000 ng/ml at 37° C. in the presence of 5% $CO_2$.10 µL (3.7 MBq/mL) of $^3$H-labeled thymidine (manufactured by Amersham Biosciences) was added and cultured at 37° C. in the presence of 5% $CO_2$ for six hours. Ramos cells were harvested on Printed Filtermat A (manufactured by PerkinElmer, Inc.) using a 96 micro cell harvester (manufactured by Skatron Instruments, Inc.), and covered with a sample bag (manufactured by PerkinElmer, Inc.). 12 mL of Betaplate Scint (manufactured by PerkinElmer, Inc.) was added, and the β-ray dose was measured with a liquid scintillation counter (Pharmacia 1205 Betaplate: manufactured by Pharmacia Corp.). Hs 766T cells, T24 cells and Capan-2 cells were respectively harvested on Unifilter (manufactured by PerkinElmer, Inc.) using a harvester (manufactured by PerkinElmer, Inc.). A special seal was attached to the back of each filter, and 20 µL/well of MicroScint 20 (manufactured by PerkinElmer, Inc.) was added thereto. The β-ray dose was measured with a scintillation counter (TopCount: manufactured by Packard Instrument Co., Inc.). Data were expressed as cell survival rates (%) obtained by dividing a mean of triplicate measurements obtained in three independent tests by a value of non-treatment control.

As a result, the cell survival rates were reduced in all cell lines depending on the 341G2Ser concentration (Table 1). When adding 100 ng/ml of 341G2Ser, the Ramos cell survival rate was 58%, the T24 cell survival rate was 22%, the Hs 766T cell survival rate was 15%, and the Capan-2 cell survival rate was 77%. 341G2Ser was found to have activity of inhibiting growth of Ramos cells, T24 cells, Hs 766T cells and Capan-2 cells.

TABLE 1

| | Cell survival rate | | | |
|---|---|---|---|---|
| | 341G2Ser concentration (ng/ml) | | | |
| Cell line | 1 | 10 | 100 | 1000 |
| Ramos | 98.49% | 81.68% | 57.77% | 55.26% |
| T24 | 97.94% | 50.72% | 21.97% | 25.35% |
| Hs 766T | 34.67% | 21.50% | 14.67% | 15.18% |
| Capan-2 | 100.94% | 85.34% | 76.76% | 72.89% |

EXAMPLE 22

Effect of Anti-CD40 Agonistic Antibody on Mouse Cancer-Bearing Model (1) Ramos cells Six-week-old female Balb/c nude mice (purchased from CLEA Japan, Inc.) were irradiated with 3Gy radiation, and $2 \times 10^7$ cells/mouse of Ramos cells were subcutaneously grafted into the back thereof. 16 days after the graft, the size of tumors that took there was measured. Cancer-bearing mice having a tumor size of 50 to 170 mm$^3$ were classified into groups each consisting of five mice. 100 µg/mouse of 341G2Ser (a solution in 200 µl of PBS containing 1% nude mouse serum) was intravenously administered to the cancer-bearing mice once on the 16th day, and the tumor size was measured until the 47th day. A human anti-human serum albumin (HAS) antibody was used as a negative control.

(2) T24 Cells

A T24 cell mass that had undergone subcutaneous passage in the back of nude mice three times were removed, and subcutaneously grafted into the back of six-week-old female Balb/c nude mice (purchased from CLEA Japan, Inc.). The tumor cell mass to be grafted is appropriately about 3 mm square. 10 days after the graft, the size of engrafted tumors was measured. Cancer-bearing mice having a tumor size of 80 to 200 mm$^3$ were classified into groups each consisting of five mice. 100 μg/mouse of 341G2Ser (a solution in 200 μl of PBS containing 1% nude mouse serum) was intravenously administered to the cancer-bearing mice once on the 10th day, and the tumor size was measured until the 29th day. The same amount of a human anti-DNP antibody was used as a negative control.

(3) Hs 766T Cells

7×10$^5$ cells/mouse of Hs 766T cells were subcutaneously grafted into the back of eight-week-old female Balb/c nude mice (purchased from CLEA Japan, Inc.). 16 days after the graft, the size of engrafted tumors was measured. Cancer-bearing mice having a tumor size of 50 to 140 mm$^3$ were classified into groups each consisting of five mice. 100 μg/mouse of 341G2Ser (a solution in 200 μl of PBS containing 1% nude mouse serum) was intravenously administered to the cancer-bearing mice once on the 16th day, and the tumor size was measured until the 32nd day. The same amount of a human anti-DNP antibody was used as a negative control.

(4) Capan-2 Cells

2×10$^6$ cells/mouse of Capan-2 cells were subcutaneously grafted into the back of six-week-old female Balb/c nude mice (purchased from CLEA Japan, Inc.). 13 days after the graft, the size of engrafted tumors was measured. Cancer-bearing mice having a tumor size of 30 to 130 mm$^3$ were classified into groups each consisting of five mice. 10 or 100 μg/mouse of 341G2Ser (a solution in 200 μl of PBS containing 1% nude mouse serum) was intravenously administered to the cancer-bearing mice twice a week from the 13th day, and the tumor size was measured until the 34th day. A human polyclonal antibody (hIgG) (manufactured by Sigma Co.) was used as a negative control.

The tumor growth inhibition ratio (TGIR) was calculated from the following formula. 100−[{(mean tumor volume of 341G2Ser-administered group on the last measurement day−mean tumor volume of 341G2Ser-administered group on the day of start of antibody administration)/(mean tumor volume of negative control-administered group on the last measurement day−mean tumor volume of negative control-administered group on the day of start of antibody administration)}×100]

As a result, TGIR exceeded 100% in the T24, Hs766T and Capan-2 cancer-bearing mice, and a decrease in the tumor volume was observed in the mice. On the other hand, TGIR was 73.4% in the Ramos cancer-bearing mice, and an increase in the tumor volume was considerably suppressed in the mice (Table 2). FIGS. 23 to 26 respectively show the change in the tumor volume of cancer-bearing mice to which Ramos cells, T24 cells, Hs 766T cells and Capan-2 cells were respectively engrafted.

TABLE 2

| | Tumor growth inhibition ratio | |
| --- | --- | --- |
| | Amount of 341G2Ser administered | |
| Cell line | 10 μg/head | 100 μg/head |
| Ramos | — | 73.40% |
| T24 | — | 109.05% |
| Hs 766T | — | 108.55% |
| Capan-2 | 103.49% | 119.20% |

The inhibition ratio in each cell line is a value on the last measurement day.

Industrial Applicability

As shown in the Examples, the anti-CD40 antibody of the present invention having a constant region into which a mutation is introduced and an anti-CD40 antibody in which a part of the structure of the subclass is substituted with that of another subclass have reduced ADCC activity and CDC activity, while maintaining its activity. Accordingly, the antibody of the present invention has the reduced cytotoxicity to CD40-expressing cells when administered to a subject as a therapeutic antibody, and thus can be used with safety.

All publications, patents and patent applications cited in this specification are herein incorporated by reference in their entirety.

Sequence Listing Free Text

SEQ ID NOS: 2 to 36: Synthetic DNAs
SEQ ID NOS: 49 to 130: Synthetic peptides

The invention claimed is:

1. A method of treating or preventing transplant rejection that comprises administering a monoclonal antibody to a patient, wherein the antibody binds human CD40 and consists of two heavy chains, each consisting of an amino acid sequence ranging from Q at position 27 to K at position 474 of SEQ ID NO: 140, and two light chains, each consisting of an amino acid sequence ranging from A at position 23 to C at position 235 of SEQ ID NO: 142.

* * * * *

UNITED STATES PATENT AND TRADEMARK OFFICE
CERTIFICATE OF CORRECTION

| | | |
|---|---|---|
| PATENT NO. | : 8,568,725 B2 | Page 1 of 1 |
| APPLICATION NO. | : 10/584345 | |
| DATED | : October 29, 2013 | |
| INVENTOR(S) | : Takahashi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1984 days.

Signed and Sealed this
Twenty-seventh Day of December, 2016

Michelle K. Lee
*Director of the United States Patent and Trademark Office*

SEQUENCE LISTING

```
<160> NUMBER OF SEQ ID NOS: 142

<210> SEQ ID NO 1
<211> LENGTH: 175
<212> TYPE: PRT
<213> ORGANISM: Homo sapiens

<400> SEQUENCE: 1

Glu Pro Pro Thr Ala Cys Arg Glu Lys Gln Tyr Leu Ile Asn Ser Gln
 1               5                  10                  15

Cys Cys Ser Leu Cys Gln Pro Gly Gln Lys Leu Val Ser Asp Cys Thr
                20                  25                  30

Glu Phe Thr Glu Thr Glu Cys Leu Pro Cys Gly Glu Ser Glu Phe Leu
            35                  40                  45

Asp Thr Trp Asn Arg Glu Thr His Cys His Gln His Lys Tyr Cys Asp
        50                  55                  60
```

-continued

```
Pro Asn Leu Gly Leu Arg Val Gln Gln Lys Gly Thr Ser Glu Thr Asp
 65                  70                  75                  80

Thr Ile Cys Thr Cys Glu Glu Gly Trp His Cys Thr Ser Glu Ala Cys
                 85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg Ala Leu
                165                 170                 175

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
atatgctagc accaagggcc catcggtctt cccctggc                         39

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
atatggatcc tcatttaccc ggagacaggg agaggctc                         38

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
atatgctagc accaagggcc catcggtctt cccctggcg                        40

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
gttttctcga tggaggctgg gaggcc                                      26

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence:Synthetic
```

```
                            DNA

<400> SEQUENCE: 6
atatggatcc tcatttaccc ggagacaggg agaggctc                              38

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
ggcctcccag cctccatcga gaaaac                                          26

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
atatggatcc tcatttaccc ggagacaggg agaggc                               36

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
aggggtccgg gagatcatga gagtgtcctt                                      30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
aaggacactc tcatgatctc ccggacccct                                      30

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
tgatcatacg tagatatcac ggc                                             23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA
```

<400> SEQUENCE: 12
tgatcatacg tagatatcac ggc                                     23

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
gggtacgtcc tcacattcag tgatcag                                 27

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 14
tttgcgctca actgtcttgt ccaccttggt gttgctggg                    39

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 15
tgatcatacg tagatatcac ggc                                     23

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 16
acagttgagc gcaaatgttg tgtcgagtgc ccaccg                       36

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 17
gggtacgtcc tcacattcag tgatcag                                 27

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 18
ggtgttgctg ggcttgtgat ctacgttgca g         31

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
ctgcaacgta gatcacaagc ccagcaacac c         31

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 20
tgatcatacg tagatatcac ggc                  23

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 21
gggtacgtcc tcacattcag tgatcag              27

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 22
ggtgttgctg ggcttgtgat ctacgttgca g         31

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 23
ctgcaacgta gatcacaagc ccagcaacac c         31

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 24
tgatcatacg tagatatcac ggc                  23

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 25
gggtacgtcc tcacattcag tgatcag                                        27

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 26
cacaacattt ggactcaact ctcttgtcca cc                                  32

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 27
ggtggacaag agagttgagt ccaaatgttg tg                                  32

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 28
tgatcatacg tagatatcac ggc                                            23

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 29
gggtacgtcc tcacattcag tgatcag                                        27

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 30
ggcacggtgg gcatggggga ccatatttgc gctc                                34

<210> SEQ ID NO 31

```
<211> LENGTH: 34
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 31
gagcgcaaat atggtccccc atgcccaccg tgcc                              34

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 32
tgatcatacg tagatatcac ggc                                          23

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 33
gggtacgtcc tcacattcag tgatcag                                      27

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 34
gaagactgac ggtcccccca ggaactctgg tgctgggca                         39

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 35
tgcccagcac cagagttcct gggggggaccg tcagtcttc                        39

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 36
tgatcatacg tagatatcac ggc                                          23

<210> SEQ ID NO 37
<211> LENGTH: 1480
<212> TYPE: DNA
```

<213> ORGANISM: Homo sapiens

<400> SEQUENCE: 37

```
gtcgacgctg aattctggct gaccagggca gccaccagag ctccagacaa tgtctgtctc    60
cttcctcatc ttcctgcccg tgctgggcct cccatgcggt gtcctgtcac aggtccaact   120
gcagcagtca ggtccaggac tggtgaagcc ctcgcagacc ctctcactca cctgtgccat   180
ctccggggac agtgtctcta gcaacagtgc tacttggaac tggatcaggc agtccccatc   240
gagagacctt gagtggctgg gaaggacata ctacaggtcc aagtggtatc gtgattatgt   300
aggatctgtg aaaagtcgaa taatcatcaa cccagacaca tccaacaacc agttctccct   360
gcagctgaac tctgtgactc ccgaggacac ggctatatat tactgtacaa gagcacagtg   420
gctgggaggg gattacccct actactacag tatggacgtc tggggccaag gaccacggt    480
caccgtctct tcagcctcca ccaagggccc atcggtcttc cccctggcgc cctgctccag   540
gagcacctcc gagagcacag cggccctggg ctgcctggtc aaggactact ccccgaacc    600
ggtgacggtg tcgtggaact caggcgctct gaccagcggc gtgcacacct tcccagctgt   660
cctacagtcc tcaggactct actccctcag cagcgtggtg accgtgccct ccagcaactt   720
cggcacccag acctacacct gcaacgtaga tcacaagccc agcaacacca aggtggacaa   780
gacagttgag cgcaaatgtt gtgtcgagtg cccaccgtgc ccagcaccac ctgtggcagg   840
accgtcagtc ttcctcttcc ccccaaaacc caaggacacc ctcatgatct cccggacccc   900
tgaggtcacg tgcgtggtgg tggacgtgag ccacgaagac cccgaggtcc agttcaactg   960
gtacgtggac ggcgtggagg tgcataatgc caagacaaag ccacgggagg agcagttcaa  1020
cagcacgttc cgtgtggtca gcgtcctcac cgttgtgcac caggactggc tgaacggcaa  1080
ggagtacaag tgcaaggtct ccaacaaagg cctcccagcc cccatcgaga aaaccatctc  1140
caaaaccaaa gggcagcccc gagaaccaca ggtgtacacc ctgccccat cccgggagga   1200
gatgaccaag aaccaggtca gcctgacctg cctggtcaaa ggcttctacc ccagcgacat  1260
cgccgtggag tgggagagca atgggcagcc ggagaacaac tacaagacca cacctcccat  1320
gctggactca gacggctcct tcttcctcta cagcaagctc accgtggaca gagcaggtg    1380
gcagcagggg aacgtcttct catgctccgt gatgcatgag gctctgcaca accactacac  1440
gcagaagagc ctctccctgt ctccgggtaa atgaggatcc                          1480
```

<210> SEQ ID NO 38
<211> LENGTH: 474
<212> TYPE: PRT
<213> ORGANISM: Homo sapiens

<400> SEQUENCE: 38

```
Met Ser Val Ser Phe Leu Ile Phe Leu Pro Val Leu Gly Leu Pro Trp
  1               5                  10                  15

Gly Val Leu Ser Gln Val Gln Leu Gln Gln Ser Gly Pro Gly Leu Val
             20                  25                  30

Lys Pro Ser Gln Thr Leu Ser Leu Thr Cys Ala Ile Ser Gly Asp Ser
         35                  40                  45

Val Ser Ser Asn Ser Ala Thr Trp Asn Trp Ile Arg Gln Ser Pro Ser
     50                  55                  60

Arg Asp Leu Glu Trp Leu Gly Arg Thr Tyr Tyr Arg Ser Lys Trp Tyr
 65                  70                  75                  80

Arg Asp Tyr Val Gly Ser Val Lys Ser Arg Ile Ile Ile Asn Pro Asp
                 85                  90                  95
```

```
Thr Ser Asn Asn Gln Phe Ser Leu Gln Leu Asn Ser Val Thr Pro Glu
            100                 105                 110

Asp Thr Ala Ile Tyr Tyr Cys Thr Arg Ala Gln Trp Leu Gly Gly Asp
            115                 120                 125

Tyr Pro Tyr Tyr Tyr Ser Met Asp Val Trp Gly Gln Gly Thr Thr Val
130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
            195                 200                 205

Gly Leu Tyr Ser Leu Ser Ser Val Val Thr Val Pro Ser Ser Asn Phe
            210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
275                 280                 285

Val Val Val Asp Val Ser His Glu Asp Pro Glu Val Gln Phe Asn Trp
            290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350

Lys Gly Leu Pro Ala Pro Ile Glu Lys Thr Ile Ser Lys Thr Lys Gly
            355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
            450                 455                 460

Gln Lys Ser Leu Ser Leu Ser Pro Gly Lys
465                 470

<210> SEQ ID NO 39
<211> LENGTH: 406
<212> TYPE: DNA
<213> ORGANISM: Homo sapiens

<400> SEQUENCE: 39
```

```
actgctcagt taggacccag agggaaccat ggaagcccca gctcagcttc tcttcctcct    60
gctactctgg ctcccagata ccaccggaga aattgtgttg acacagtctc cagccaccct   120
gtctttgtct ccaggggaaa gagccaccct ctcctgcagg gccagtcaga gtgttagcag   180
ctacttagcc tggtaccaac agaaacctgg ccaggctccc aggctcctca tctatgatgc   240
atccaacagg gccactggca tcccagccag gttcagtggc agtgggtctg ggacagactt   300
cactctcacc atcagcagcc tagagcctga agattttgca gtttattact gtcagcagcg   360
tagcaacact ttcggccctg ggaccaaagt ggatatcaaa cgtacg              406
```

<210> SEQ ID NO 40
<211> LENGTH: 126
<212> TYPE: PRT
<213> ORGANISM: Homo sapiens

<400> SEQUENCE: 40

```
Met Glu Ala Pro Ala Gln Leu Leu Phe Leu Leu Leu Trp Leu Pro
 1               5                  10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
    65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
               100                 105                 110

Asn Thr Phe Gly Pro Gly Thr Lys Val Asp Ile Lys Arg Thr
           115                 120                 125
```

<210> SEQ ID NO 41
<211> LENGTH: 508
<212> TYPE: DNA
<213> ORGANISM: Homo sapiens

<400> SEQUENCE: 41

```
ctgaacacag acccgtcgac tcccaggtgt tccattcag tgatcagcac tgaacacaga     60
ggactcacca tggagttggg actgagctgg attttccttt tggctatttt aaaaggtgtc   120
cagtgtgaag tgcagctggt ggagtctggg ggaggcttgg tacagcctgg caggtccctg   180
agactctcct gtgcagcctc tggattcacc tttgatgatt atgccatgca ctgggtccgg   240
caagctccag ggaagggcct ggagtgggtc tcaggtatta gttggaatag tggtagcttg   300
gtgcatgcga ctctgtgaa gggccgattc accatctcca gagacaacgc caagaactcc   360
ctgtatctgc aaatgaacag tctgagagct gaggacacgg ccttgtatta ctgtgcaaga   420
gataggctat ttcggggagt taggtactac ggtatggacg tctggggcca agggaccacg   480
gtcaccgtct cctcagctag caccaagg                                      508
```

<210> SEQ ID NO 42
<211> LENGTH: 146
<212> TYPE: PRT
<213> ORGANISM: Homo sapiens

<400> SEQUENCE: 42

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Gly Ile Ser Trp Asn Ser Gly Ser Leu Val His Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Arg Leu Phe Arg Gly Val Arg Tyr Tyr Gly
        115                 120                 125

Met Asp Val Trp Gly Gln Gly Thr Thr Val Thr Val Ser Ser Ala Ser
    130                 135                 140

Thr Lys
145

<210> SEQ ID NO 43
<211> LENGTH: 414
<212> TYPE: DNA
<213> ORGANISM: Homo sapiens

<400> SEQUENCE: 43
ctgctcagtt aggacccaga gggaaccatg gaagccccag ctcagcttct cttcctcctg    60
ctactctggc tcccagatac caccggagaa attgtgttga cacagtctcc agccaccctg   120
tctttgtctc caggggaaag agccaccctc tcctgcaggg ccagtcagag tgttagcagc   180
tacttagcct ggtaccaaca gaaacctggc caggctccca ggctcctcat ctatgatgca   240
tccaacaggg ccactggcat cccagccagg ttcagtggca gtgggtctgg gacagacttc   300
actctcacca tcagcagcct agagcctgaa gattttgcag tttattactg tcagcagcgt   360
agccactggc tcactttcgg cggggggacc aaggtggaga tcaaacgtac ggtg         414

<210> SEQ ID NO 44
<211> LENGTH: 129
<212> TYPE: PRT
<213> ORGANISM: Homo sapiens

<400> SEQUENCE: 44

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

His Trp Leu Thr Phe Gly Gly Gly Thr Lys Val Glu Ile Lys Arg Thr
        115                 120                 125
Val

<210> SEQ ID NO 45
<211> LENGTH: 462
<212> TYPE: DNA
<213> ORGANISM: Homo sapiens

<400> SEQUENCE: 45

```
atatgtcgac gagtcatgga tctcatgtgc aagaaaatga agcacctgtg gttcttcctc      60
ctgctggtgg cggctcccag atgggtcctg tcccagctgc agctgcagga gtcgggccca    120
ggactactga agccttcgga gaccctgtcc ctcacctgca ctgtctctgg cggctccatc    180
agcagtcctg gttactacgg gggctggatc cgccagcccc cagggaaggg gctggagtgg    240
attgggagta tctataaaag tgggagcacc taccacaacc cgtccctcaa gagtcgagtc    300
accatatccg tagacacgtc caagaaccag ttctccctga agctgagctc tgtgaccgcc    360
gcagacacgg ctgtgtatta ctgtacgaga cctgtagtac gatattttgg gtggttcgac    420
ccctggggcc agggaaccct ggtcaccgtc tcctcagcta gc                       462
```

<210> SEQ ID NO 46
<211> LENGTH: 149
<212> TYPE: PRT
<213> ORGANISM: Homo sapiens

<400> SEQUENCE: 46

Met Asp Leu Met Cys Lys Lys Met Lys His Leu Trp Phe Phe Leu Leu
 1               5                  10                  15

Leu Val Ala Ala Pro Arg Trp Val Leu Ser Gln Leu Gln Leu Gln Glu
            20                  25                  30

Ser Gly Pro Gly Leu Leu Lys Pro Ser Glu Thr Leu Ser Leu Thr Cys
        35                  40                  45

Thr Val Ser Gly Gly Ser Ile Ser Ser Pro Gly Tyr Tyr Gly Gly Trp
    50                  55                  60

Ile Arg Gln Pro Pro Gly Lys Gly Leu Glu Trp Ile Gly Ser Ile Tyr
 65                  70                  75                  80

Lys Ser Gly Ser Thr Tyr His Asn Pro Ser Leu Lys Ser Arg Val Thr
                85                  90                  95

Ile Ser Val Asp Thr Ser Lys Asn Gln Phe Ser Leu Lys Leu Ser Ser
            100                 105                 110

Val Thr Ala Ala Asp Thr Ala Val Tyr Tyr Cys Thr Arg Pro Val Val
        115                 120                 125

Arg Tyr Phe Gly Trp Phe Asp Pro Trp Gly Gln Gly Thr Leu Val Thr
    130                 135                 140

Val Ser Ser Ala Ser
145

<210> SEQ ID NO 47
<211> LENGTH: 448
<212> TYPE: DNA
<213> ORGANISM: Homo sapiens

<400> SEQUENCE: 47

```
agatcttaag caagtgtaac aactcagagt acgcggggag acccactcag gacacagcat      60
ggacatgagg gtccccgctc agctcctggg gcttctgctg ctctggctcc caggtgccag    120
```

```
atgtgccatc cagttgaccc agtctccatc ctccctgtct gcatctgtag gagacagagt       180
caccatcact tgccgggcaa gtcagggcat tagcagtgct ttagcctggt atcagcagaa       240
accagggaaa gctcctaagc tcctgatcta tgatgcctcc aatttggaaa gtggggtccc       300
atcaaggttc agcggcagtg gatctgggac agatttcact ctcaccatca gcagcctgca       360
gcctgaagat tttgcaactt attactgtca acagtttaat agttacccga cgttcggcca       420
agggaccaag gtggaaatca aacgtacg                                           448
```

```
<210> SEQ ID NO 48
<211> LENGTH: 130
<212> TYPE: PRT
<213> ORGANISM: Homo sapiens

<400> SEQUENCE: 48

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Asn Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Thr Phe Gly Gln Gly Thr Lys Val Glu Ile Lys
        115                 120                 125

Arg Thr
    130

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 49

Glu Pro Pro Thr Ala Cys Arg Glu Lys Gln Tyr Leu Ile
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 50

Pro Thr Ala Cys Arg Glu Lys Gln Tyr Leu Ile Asn Ser
1               5                   10

<210> SEQ ID NO 51
<211> LENGTH: 13
<212> TYPE: PRT
<213> ORGANISM: Artificial Sequence
```

```
<220> FEATURE:
<223> OTHER INFORMATION: Description of Artificial Sequence:Synthetic
      peptide

<400> SEQUENCE: 51

Ala Cys Arg Glu Lys Gln Tyr Leu Ile Asn Ser Gln Cys
 1               5                  10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 52

Arg Glu Lys Gln Tyr Leu Ile Asn Ser Gln Cys Cys Ser
 1               5                  10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 53

Lys Gln Tyr Leu Ile Asn Ser Gln Cys Cys Ser Leu Cys
 1               5                  10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 54

Tyr Leu Ile Asn Ser Gln Cys Cys Ser Leu Cys Gln Pro
 1               5                  10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 55

Ile Asn Ser Gln Cys Cys Ser Leu Cys Gln Pro Gly Gln
 1               5                  10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 56

Ser Gln Cys Cys Ser Leu Cys Gln Pro Gly Gln Lys Leu
 1               5                  10
```

```
<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 57

Cys Cys Ser Leu Cys Gln Pro Gly Gln Lys Leu Val Ser
 1               5                  10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 58

Ser Leu Cys Gln Pro Gly Gln Lys Leu Val Ser Asp Cys
 1               5                  10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 59

Cys Gln Pro Gly Gln Lys Leu Val Ser Asp Cys Thr Glu
 1               5                  10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 60

Pro Gly Gln Lys Leu Val Ser Asp Cys Thr Glu Phe Thr
 1               5                  10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 61

Gln Lys Leu Val Ser Asp Cys Thr Glu Phe Thr Glu Thr
 1               5                  10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 62
```

Leu Val Ser Asp Cys Thr Glu Phe Thr Glu Thr Glu Cys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 63

Ser Asp Cys Thr Glu Phe Thr Glu Thr Glu Cys Leu Pro
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 64

Cys Thr Glu Phe Thr Glu Thr Glu Cys Leu Pro Cys Gly
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 65

Glu Phe Thr Glu Thr Glu Cys Leu Pro Cys Gly Glu Ser
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 66

Thr Glu Thr Glu Cys Leu Pro Cys Gly Glu Ser Glu Phe
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 67

Thr Glu Cys Leu Pro Cys Gly Glu Ser Glu Phe Leu Asp
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence:Synthetic -continued

```
      peptide

<400> SEQUENCE: 68

Cys Leu Pro Cys Gly Glu Ser Glu Phe Leu Asp Thr Trp
 1               5                  10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 69

Pro Cys Gly Glu Ser Glu Phe Leu Asp Thr Trp Asn Arg
 1               5                  10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 70

Gly Glu Ser Glu Phe Leu Asp Thr Trp Asn Arg Glu Thr
 1               5                  10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 71

Ser Glu Phe Leu Asp Thr Trp Asn Arg Glu Thr His Cys
 1               5                  10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 72

Phe Leu Asp Thr Trp Asn Arg Glu Thr His Cys His Gln
 1               5                  10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 73

Asp Thr Trp Asn Arg Glu Thr His Cys His Gln His Lys
 1               5                  10

<210> SEQ ID NO 74
<211> LENGTH: 13
```

```
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 74

Trp Asn Arg Glu Thr His Cys His Gln His Lys Tyr Cys
 1               5                  10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 75

Arg Glu Thr His Cys His Gln His Lys Tyr Cys Asp Pro
 1               5                  10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 76

Thr His Cys His Gln His Lys Tyr Cys Asp Pro Asn Leu
 1               5                  10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 77

Cys His Gln His Lys Tyr Cys Asp Pro Asn Leu Gly Leu
 1               5                  10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 78

Gln His Lys Tyr Cys Asp Pro Asn Leu Gly Leu Arg Val
 1               5                  10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 79

Lys Tyr Cys Asp Pro Asn Leu Gly Leu Arg Val Gln Gln
 1               5                  10
```

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 80

Cys Asp Pro Asn Leu Gly Leu Arg Val Gln Gln Lys Gly
 1               5                  10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 81

Pro Asn Leu Gly Leu Arg Val Gln Gln Lys Gly Thr Ser
 1               5                  10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 82

Leu Gly Leu Arg Val Gln Gln Lys Gly Thr Ser Glu Thr
 1               5                  10

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 83

Leu Arg Val Gln Gln Lys Gly Thr Ser Glu Thr Asp Thr
 1               5                  10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 84

Val Gln Gln Lys Gly Thr Ser Glu Thr Asp Thr Ile Cys
 1               5                  10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

```
<400> SEQUENCE: 85

Gln Lys Gly Thr Ser Glu Thr Asp Thr Ile Cys Thr Cys
  1               5                  10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 86

Gly Thr Ser Glu Thr Asp Thr Ile Cys Thr Cys Glu Glu
  1               5                  10

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 87

Ser Glu Thr Asp Thr Ile Cys Thr Cys Glu Glu Gly Trp
  1               5                  10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 88

Thr Asp Thr Ile Cys Thr Cys Glu Glu Gly Trp His Cys
  1               5                  10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 89

Thr Ile Cys Thr Cys Glu Glu Gly Trp His Cys Thr Ser
  1               5                  10

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 90

Cys Thr Cys Glu Glu Gly Trp His Cys Thr Ser Glu Ala
  1               5                  10

<210> SEQ ID NO 91
<211> LENGTH: 13
<212> TYPE: PRT
<213> ORGANISM: Artificial Sequence
```

```
<220> FEATURE:
<223> OTHER INFORMATION: Description of Artificial Sequence:Synthetic
      peptide

<400> SEQUENCE: 91

Cys Glu Glu Gly Trp His Cys Thr Ser Glu Ala Cys Glu
 1               5                   10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 92

Glu Gly Trp His Cys Thr Ser Glu Ala Cys Glu Ser Cys
 1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 93

Trp His Cys Thr Ser Glu Ala Cys Glu Ser Cys Val Leu
 1               5                   10

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 94

Cys Thr Ser Glu Ala Cys Glu Ser Cys Val Leu His Arg
 1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 95

Ser Glu Ala Cys Glu Ser Cys Val Leu His Arg Ser Cys
 1               5                   10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 96

Ala Cys Glu Ser Cys Val Leu His Arg Ser Cys Ser Pro
 1               5                   10
```

```
<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 97

Glu Ser Cys Val Leu His Arg Ser Cys Ser Pro Gly Phe
 1               5                  10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 98

Cys Val Leu His Arg Ser Cys Ser Pro Gly Phe Gly Val
 1               5                  10

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 99

Leu His Arg Ser Cys Ser Pro Gly Phe Gly Val Lys Gln
 1               5                  10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 100

Arg Ser Cys Ser Pro Gly Phe Gly Val Lys Gln Ile Ala
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 101

Cys Ser Pro Gly Phe Gly Val Lys Gln Ile Ala Thr Gly
 1               5                  10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 102
```

```
Pro Gly Phe Gly Val Lys Gln Ile Ala Thr Gly Val Ser
 1               5                  10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 103

Phe Gly Val Lys Gln Ile Ala Thr Gly Val Ser Asp Thr
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 104

Val Lys Gln Ile Ala Thr Gly Val Ser Asp Thr Ile Cys
 1               5                  10

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 105

Gln Ile Ala Thr Gly Val Ser Asp Thr Ile Cys Glu Pro
 1               5                  10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 106

Ala Thr Gly Val Ser Asp Thr Ile Cys Glu Pro Cys Pro
 1               5                  10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 107

Gly Val Ser Asp Thr Ile Cys Glu Pro Cys Pro Val Gly
 1               5                  10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence:Synthetic
```

```
                peptide

<400> SEQUENCE: 108

Ser Asp Thr Ile Cys Glu Pro Cys Pro Val Gly Phe Phe
  1               5                  10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 109

Thr Ile Cys Glu Pro Cys Pro Val Gly Phe Phe Ser Asn
  1               5                  10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 110

Cys Glu Pro Cys Pro Val Gly Phe Phe Ser Asn Val Ser
  1               5                  10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 111

Pro Cys Pro Val Gly Phe Phe Ser Asn Val Ser Ser Ala
  1               5                  10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 112

Pro Val Gly Phe Phe Ser Asn Val Ser Ser Ala Phe Glu
  1               5                  10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 113

Gly Phe Phe Ser Asn Val Ser Ser Ala Phe Glu Lys Cys
  1               5                  10

<210> SEQ ID NO 114
<211> LENGTH: 13
```

```
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 114

Phe Ser Asn Val Ser Ser Ala Phe Glu Lys Cys His Pro
 1               5                  10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 115

Asn Val Ser Ser Ala Phe Glu Lys Cys His Pro Trp Thr
 1               5                  10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 116

Ser Ser Ala Phe Glu Lys Cys His Pro Trp Thr Ser Cys
 1               5                  10

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 117

Ala Phe Glu Lys Cys His Pro Trp Thr Ser Cys Glu Thr
 1               5                  10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 118

Glu Lys Cys His Pro Trp Thr Ser Cys Glu Thr Lys Asp
 1               5                  10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 119

Cys His Pro Trp Thr Ser Cys Glu Thr Lys Asp Leu Val
 1               5                  10
```

```
<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 120

Pro Trp Thr Ser Cys Glu Thr Lys Asp Leu Val Val Gln
  1               5                  10

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 121

Thr Ser Cys Glu Thr Lys Asp Leu Val Val Gln Gln Ala
  1               5                  10

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 122

Cys Glu Thr Lys Asp Leu Val Val Gln Gln Ala Gly Thr
  1               5                  10

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 123

Thr Lys Asp Leu Val Val Gln Gln Ala Gly Thr Asn Lys
  1               5                  10

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 124

Asp Leu Val Val Gln Gln Ala Gly Thr Asn Lys Thr Asp
  1               5                  10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide
```

```
<400> SEQUENCE: 125

Val Val Gln Gln Ala Gly Thr Asn Lys Thr Asp Val Val
  1               5                  10

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 126

Gln Gln Ala Gly Thr Asn Lys Thr Asp Val Val Cys Gly
  1               5                  10

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 127

Ala Gly Thr Asn Lys Thr Asp Val Val Cys Gly Pro Gln
  1               5                  10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 128

Thr Asn Lys Thr Asp Val Val Cys Gly Pro Gln Asp Arg
  1               5                  10

<210> SEQ ID NO 129
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 129

Lys Thr Asp Val Val Cys Gly Pro Gln Asp Arg Leu Arg
  1               5                  10

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 130

Asp Val Val Cys Gly Pro Gln Asp Arg Leu Arg Ala Leu
  1               5                  10

<210> SEQ ID NO 131
<211> LENGTH: 1425
<212> TYPE: DNA
<213> ORGANISM: Homo sapiens
```

<400> SEQUENCE: 131

```
atgtctgtct ccttcctcat cttcctgccc gtgctgggcc tcccatgggg tgtcctgtca        60
caggtccaac tgcagcagtc aggtccagga ctggtgaagc cctcgcagac cctctcactc       120
acctgtgcca tctccgggga cagtgtctct agcaacagtg ctacttggaa ctggatcagg       180
cagtccccat cgagagacct tgagtggctg gaaggacat actacaggtc caagtggtat        240
cgtgattatg taggatctgt gaaaagtcga ataatcatca acccagacac atccaacaac       300
cagttctccc tgcagctgaa ctctgtgact cccgaggaca cggctatata ttactgtaca       360
agagcacagt ggctgggagg ggattacccc tactactaca gtatggacgt ctggggccaa       420
gggaccacgg tcaccgtctc ctcagctagc accaagggcc catcggtctt ccccctggcg       480
ccctgctcca ggagcacctc cgagagcaca gcggccctgg gctgcctggt caaggactac       540
ttccccgaac cggtgacggt gtcgtggaac tcaggcgctc tgaccagcgg cgtgcacacc       600
ttcccagctg tcctacagtc ctcaggactc tactccctca gcagcgtggt gaccgtgccc       660
tccagcaact tcggcaccca gacctacacc tgcaacgtag atcacaagcc cagcaacacc       720
aaggtggaca agacagttga gcgcaaatgt tgtgtcgagt gcccaccgtg cccagcacca       780
cctgtggcag gaccgtcagt cttcctcttc cccccaaaac ccaaggacac cctcatgatc       840
tcccggaccc ctgaggtcac gtgcgtggtg gtggacgtga gccacgaaga ccccgaggtc       900
cagttcaact ggtacgtgga cggcgtggag gtgcataatg ccaagacaaa gccacgggag       960
gagcagttca acagcacgtt ccgtgtggtc agcgtcctca ccgttgtgca ccaggactgg      1020
ctgaacggca aggagtacaa gtgcaaggtc tccaacaaag gcctcccagc tccatcgag       1080
aaaaccatct ccaaaaccaa agggcagccc cgagaaccac aggtgtacac cctgcccca       1140
tcccgggagg agatgaccaa gaaccaggtc agcctgacct gcctggtcaa aggcttctac      1200
cccagcgaca tcgccgtgga gtgggagagc aatgggcagc cggagaacaa ctacaagacc      1260
acacctccca tgctggactc cgacggctcc ttcttcctct acagcaagct caccgtggac      1320
aagagcaggt ggcagcaggg gaacgtcttc tcatgctccg tgatgcatga ggctctgcac      1380
aaccactaca cgcagaagag cctctccctg tctccgggta aatga                      1425
```

<210> SEQ ID NO 132
<211> LENGTH: 474
<212> TYPE: PRT
<213> ORGANISM: Homo sapiens

<400> SEQUENCE: 132

```
Met Ser Val Ser Phe Leu Ile Phe Leu Pro Val Leu Gly Leu Pro Trp
  1               5                  10                  15

Gly Val Leu Ser Gln Val Gln Leu Gln Gln Ser Gly Pro Gly Leu Val
             20                  25                  30

Lys Pro Ser Gln Thr Leu Ser Leu Thr Cys Ala Ile Ser Gly Asp Ser
         35                  40                  45

Val Ser Ser Asn Ser Ala Thr Trp Asn Trp Ile Arg Gln Ser Pro Ser
     50                  55                  60

Arg Asp Leu Glu Trp Leu Gly Arg Thr Tyr Tyr Arg Ser Lys Trp Tyr
 65                  70                  75                  80

Arg Asp Tyr Val Gly Ser Val Lys Ser Arg Ile Ile Ile Asn Pro Asp
                 85                  90                  95

Thr Ser Asn Asn Gln Phe Ser Leu Gln Leu Asn Ser Val Thr Pro Glu
            100                 105                 110
```

```
Asp Thr Ala Ile Tyr Tyr Cys Thr Arg Ala Gln Trp Leu Gly Gly Asp
            115                 120                 125
Tyr Pro Tyr Tyr Tyr Ser Met Asp Val Trp Gly Gln Gly Thr Thr Val
    130                 135                 140
Thr Val Ser Ser Ala Ser Thr Lys Gly Pro Ser Val Phe Pro Leu Ala
145                 150                 155                 160
Pro Cys Ser Arg Ser Thr Ser Glu Ser Thr Ala Ala Leu Gly Cys Leu
                165                 170                 175
Val Lys Asp Tyr Phe Pro Glu Pro Val Thr Val Ser Trp Asn Ser Gly
            180                 185                 190
Ala Leu Thr Ser Gly Val His Thr Phe Pro Ala Val Leu Gln Ser Ser
        195                 200                 205
Gly Leu Tyr Ser Leu Ser Ser Val Val Thr Val Pro Ser Ser Asn Phe
    210                 215                 220
Gly Thr Gln Thr Tyr Thr Cys Asn Val Asp His Lys Pro Ser Asn Thr
225                 230                 235                 240
Lys Val Asp Lys Thr Val Glu Arg Lys Cys Val Glu Cys Pro Pro
                245                 250                 255
Cys Pro Ala Pro Pro Val Ala Gly Pro Ser Val Phe Leu Phe Pro Pro
            260                 265                 270
Lys Pro Lys Asp Thr Leu Met Ile Ser Arg Thr Pro Glu Val Thr Cys
        275                 280                 285
Val Val Val Asp Val Ser His Glu Asp Pro Glu Val Gln Phe Asn Trp
    290                 295                 300
Tyr Val Asp Gly Val Glu Val His Asn Ala Lys Thr Lys Pro Arg Glu
305                 310                 315                 320
Glu Gln Phe Asn Ser Thr Phe Arg Val Val Ser Val Leu Thr Val Val
                325                 330                 335
His Gln Asp Trp Leu Asn Gly Lys Glu Tyr Lys Cys Lys Val Ser Asn
            340                 345                 350
Lys Gly Leu Pro Ala Ser Ile Glu Lys Thr Ile Ser Lys Thr Lys Gly
        355                 360                 365
Gln Pro Arg Glu Pro Gln Val Tyr Thr Leu Pro Pro Ser Arg Glu Glu
    370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Met Leu Asp Ser Asp Gly Ser Phe Phe
            420                 425                 430
Leu Tyr Ser Lys Leu Thr Val Asp Lys Ser Arg Trp Gln Gln Gly Asn
        435                 440                 445
Val Phe Ser Cys Ser Val Met His Glu Ala Leu His Asn His Tyr Thr
    450                 455                 460
Gln Lys Ser Leu Ser Leu Ser Pro Gly Lys
465                 470

<210> SEQ ID NO 133
<211> LENGTH: 696
<212> TYPE: DNA
<213> ORGANISM: Homo sapiens

<400> SEQUENCE: 133
atggaagccc cagctcagct tctcttcctc ctgctactct ggctcccaga taccaccgga    60
gaaattgtgt tgacacagtc tccagccacc ctgtctttgt ctccagggga aagagccacc   120
```

```
ctctcctgca gggccagtca gagtgttagc agctacttag cctggtacca acagaaacct      180
ggccaggctc ccaggctcct catctatgat gcatccaaca gggccactgg catcccagcc      240
aggttcagtg gcagtgggtc tgggacagac ttcactctca ccatcagcag cctagagcct      300
gaagattttg cagtttatta ctgtcagcag cgtagcaaca ctttcggccc tgggaccaaa      360
gtggatatca aacgtacggt ggctgcacca tctgtcttca tcttcccgcc atctgatgag      420
cagttgaaat ctggaactgc ctctgttgtg tgcctgctga ataacttcta tcccagagag      480
gccaaagtac agtggaaggt ggataacgcc ctccaatcgg gtaactccca ggagagtgtc      540
acagagcagg acagcaagga cagcacctac agcctcagca gcaccctgac gctgagcaaa      600
gcagactacg agaaacacaa agtctacgcc tgcgaagtca cccatcaggg cctgagctcg      660
cccgtcacaa agagcttcaa caggggagag tgttga                                696
```

<210> SEQ ID NO 134
<211> LENGTH: 231
<212> TYPE: PRT
<213> ORGANISM: Homo sapiens

<400> SEQUENCE: 134

```
Met Glu Ala Pro Ala Gln Leu Leu Phe Leu Leu Leu Leu Trp Leu Pro
 1               5                  10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Thr Phe Gly Pro Gly Thr Lys Val Asp Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230
```

<210> SEQ ID NO 135
<211> LENGTH: 1407
<212> TYPE: DNA
<213> ORGANISM: Homo sapiens -continued

```
<400> SEQUENCE: 135
atggagttgg gactgagctg gattttcctt ttggctattt taaaaggtgt ccagtgtgaa      60
gtgcagctgg tggagtctgg gggaggcttg gtacagcctg gcaggtccct gagactctcc    120
tgtgcagcct ctggattcac ctttgatgat tatgccatgc actgggtccg gcaagctcca    180
gggaagggcc tggagtgggt ctcaggtatt agttggaata gtggtagctt ggtgcatgcg    240
gactctgtga agggccgatt caccatctcc agagacaacg ccaagaactc cctgtatctg    300
caaatgaaca gtctgagagc tgaggacacg gccttgtatt actgtgcaag agataggcta    360
tttcggggag ttaggtacta cggtatggac gtctggggcc aagggaccac ggtcaccgtc    420
tcctcagcta gcaccaaggg cccatcggtc ttccccctgg cgcctgctc caggagcacc     480
tccgagagca gcggcccct gggctgcctg gtcaaggact acttccccga accggtgacg     540
gtgtcgtgga actcaggcgc tctgaccagc ggcgtgcaca ccttcccagc tgtcctacag    600
tcctcaggac tctactccct cagcagcgtg gtgaccgtgc cctccagcaa cttcggcacc    660
cagacctaca cctgcaacgt agatcacaag cccagcaaca ccaaggtgga caagacagtt    720
gagcgcaaat gttgtgtcga gtgcccaccg tgcccagcac cacctgtggc aggaccgtca    780
gtcttcctct tccccccaaa acccaaggac accctcatga tctcccggac ccctgaggtc    840
acgtgcgtgg tggtggacgt gagccacgaa gaccccgagg tccagttcaa ctggtacgtg    900
gacggcgtgg aggtgcataa tgccaagaca aagccacggg aggagcagtt caacagcacg    960
ttccgtgtgg tcagcgtcct caccgttgtg caccaggact ggctgaacgg caaggagtac   1020
aagtgcaagg tctccaacaa aggcctccca gcctccatcg agaaaaccat ctccaaaacc   1080
aaagggcagc cccgagaacc acaggtgtac accctgcccc catcccggga ggagatgacc   1140
aagaaccagg tcagcctgac ctgcctggtc aaaggcttct accccagcga catcgccgtg   1200
gagtgggaga gcaatgggca gccggagaac aactacaaga ccacacctcc catgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                       1407

<210> SEQ ID NO 136
<211> LENGTH: 468
<212> TYPE: PRT
<213> ORGANISM: Homo sapiens

<400> SEQUENCE: 136

Met Glu Leu Gly Leu Ser Trp Ile Phe Leu Leu Ala Ile Leu Lys Gly
  1               5                  10                  15
Val Gln Cys Glu Val Gln Leu Val Glu Ser Gly Gly Gly Leu Val Gln
                 20                  25                  30
Pro Gly Arg Ser Leu Arg Leu Ser Cys Ala Ala Ser Gly Phe Thr Phe
             35                  40                  45
Asp Asp Tyr Ala Met His Trp Val Arg Gln Ala Pro Gly Lys Gly Leu
         50                  55                  60
Glu Trp Val Ser Gly Ile Ser Trp Asn Ser Gly Ser Leu Val His Ala
 65                  70                  75                  80
Asp Ser Val Lys Gly Arg Phe Thr Ile Ser Arg Asp Asn Ala Lys Asn
                 85                  90                  95
Ser Leu Tyr Leu Gln Met Asn Ser Leu Arg Ala Glu Asp Thr Ala Leu
            100                 105                 110
Tyr Tyr Cys Ala Arg Asp Arg Leu Phe Arg Gly Val Arg Tyr Tyr Gly
```

```
                115                 120                 125
Met Asp Val Trp Gly Gln Gly Thr Thr Val Thr Val Ser Ser Ala Ser
130                     135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Ser
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 137
<211> LENGTH: 702
<212> TYPE: DNA
<213> ORGANISM: Homo sapiens

<400> SEQUENCE: 137
atggaagccc cagctcagct tctcttcctc ctgctactct ggctcccaga taccaccgga     60
gaaattgtgt tgacacagtc tccagccacc ctgtctttgt ctccagggga aagagccacc    120
```

```
ctctcctgca gggccagtca gagtgttagc agctacttag cctggtacca acagaaacct    180
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagtttatta ctgtcagcag cgtagccact ggctcacttt cggcggggg    360 accaaggtgg agatcaaacg tacggtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ga    702
```

<210> SEQ ID NO 138
<211> LENGTH: 233
<212> TYPE: PRT
<213> ORGANISM: Homo sapiens

<400> SEQUENCE: 138

```
Met Glu Ala Pro Ala Gln Leu Leu Phe Leu Leu Leu Leu Trp Leu Pro
 1               5                  10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

His Trp Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 139
<211> LENGTH: 1425
<212> TYPE: DNA
<213> ORGANISM: Homo sapiens

<400> SEQUENCE: 139

```
atggatctca tgtgcaagaa aatgaagcac ctgtggttct tcctcctgct ggtggcggct      60
cccagatggg tcctgtccca gctgcagctg caggagtcgg gcccaggact actgaagcct     120
tcggagaccc tgtccctcac ctgcactgtc tctggcggct ccatcagcag tcctggttac     180
tacgggggct ggatccgcca gccccagggg aaggggctgg agtggattgg agtatctat     240 aaaagtggga gcacctacca caacccgtcc ctcaagagtc gagtcaccat atccgtagac     300
acgtccaaga accagttctc cctgaagctg agctctgtga ccgccgcaga cacggctgtg     360
tattactgta cgagacctgt agtacgatat tttggtggt tcgacccctg gggccaggga     420
accctggtca ccgtctcctc agctagcacc aaggggccat ccgtcttccc cctggcgccc     480
tgctccagga gcacctccga gagcacagcg gccctgggct gcctggtcaa ggactacttc     540
cccgaaccgg tgacggtgtc gtggaactca ggcgccctga ccagcggcgt gcacaccttc     600
ccggctgtcc tacagtcctc aggactctac tccctcagca gcgtggtgac cgtgccctcc     660
agcagcttgg gcacgaagac ctacacctgc aacgtagatc acaagcccag caacaccaag     720
gtggacaaga gagttgagtc caaatatggt ccccatgcc caccatgccc agcacctgag     780
ttcgaggggg gaccatcagt cttcctgttc cccccaaaac ccaaggacac tctcatgatc     840
tcccggaccc ctgaggtcac gtgcgtggtg gtggacgtga gccaggaaga ccccgaggtc     900
cagttcaact ggtacgtgga tggcgtggag gtgcataatg ccaagacaaa gccgcgggag     960
gagcagttca acagcacgta ccgtgtggtc agcgtcctca ccgtcctgca ccaggactgg    1020
ctgaacggca aggagtacaa gtgcaaggtc tccaacaaag gcctcccgtc ctccatcgag    1080
aaaaccatct ccaaagccaa agggcagccc cgagagccac aggtgtacac cctgcccca    1140 tcccaggagg agatgaccaa gaaccaggtc agcctgacct gcctggtcaa aggcttctac    1200
cccagcgaca tcgccgtgga gtgggagagc aatgggcagc cggagaacaa ctacaagacc    1260
acgcctcccg tgctggactc cgacggctcc ttcttcctct acagcaggct aaccgtggac    1320
aagagcaggt ggcaggaggg gaatgtcttc tcatgctccg tgatgcatga ggctctgcac    1380
aaccactaca cacagaagag cctctccctg tctctgggta aatga                    1425
```

<210> SEQ ID NO 140
<211> LENGTH: 474
<212> TYPE: PRT
<213> ORGANISM: Homo sapiens

<400> SEQUENCE: 140

```
Met Asp Leu Met Cys Lys Lys Met Lys His Leu Trp Phe Phe Leu Leu
  1               5                  10                  15

Leu Val Ala Ala Pro Arg Trp Val Leu Ser Gln Leu Gln Leu Gln Glu
             20                  25                  30

Ser Gly Pro Gly Leu Leu Lys Pro Ser Glu Thr Leu Ser Leu Thr Cys
         35                  40                  45

Thr Val Ser Gly Gly Ser Ile Ser Ser Pro Gly Tyr Tyr Gly Gly Trp
     50                  55                  60

Ile Arg Gln Pro Pro Gly Lys Gly Leu Glu Trp Ile Gly Ser Ile Tyr
 65                  70                  75                  80

Lys Ser Gly Ser Thr Tyr His Asn Pro Ser Leu Lys Ser Arg Val Thr
                 85                  90                  95

Ile Ser Val Asp Thr Ser Lys Asn Gln Phe Ser Leu Lys Leu Ser Ser
            100                 105                 110

Val Thr Ala Ala Asp Thr Ala Val Tyr Tyr Cys Thr Arg Pro Val Val
        115                 120                 125
```

```
Arg Tyr Phe Gly Trp Phe Asp Pro Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Lys Thr Tyr Thr Cys Asn Val Asp His Lys Pro Ser Asn Thr Lys
225                 230                 235                 240

Val Asp Lys Arg Val Glu Ser Lys Tyr Gly Pro Pro Cys Pro Pro Cys
                245                 250                 255

Pro Ala Pro Glu Phe Glu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys
465                 470

<210> SEQ ID NO 141
<211> LENGTH: 708
<212> TYPE: DNA
<213> ORGANISM: Homo sapiens

<400> SEQUENCE: 141
atggacatga gggtccccgc tcagctcctg gggcttctgc tgctctggct cccaggtgcc      60
agatgtgcca tccagttgac ccagtctcca tcctccctgt ctgcatctgt aggagacaga    120
gtcaccatca cttgccgggc aagtcagggc attagcagtg ctttagcctg gtatcagcag    180
```

-continued

```
aaaccaggga aagctcctaa gctcctgatc tatgatgcct ccaatttgga aagtggggtc    240
ccatcaaggt tcagcggcag tggatctggg acagatttca ctctcaccat cagcagcctg    300
cagcctgaag attttgcaac ttattactgt caacagttta atagttaccc gacgttcggc    360
caagggacca aggtggaaat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgttga                708
```

```
<210> SEQ ID NO 142
<211> LENGTH: 235
<212> TYPE: PRT
<213> ORGANISM: Homo sapiens

<400> SEQUENCE: 142
```

```
Met Asp Met Arg Val Pro Ala Gln Leu Leu Gly Leu Leu Leu Leu Trp
 1               5                  10                  15

Leu Pro Gly Ala Arg Cys Ala Ile Gln Leu Thr Gln Ser Pro Ser Ser
             20                  25                  30

Leu Ser Ala Ser Val Gly Asp Arg Val Thr Ile Thr Cys Arg Ala Ser
         35                  40                  45

Gln Gly Ile Ser Ser Ala Leu Ala Trp Tyr Gln Lys Pro Gly Lys
     50                  55                  60

Ala Pro Lys Leu Leu Ile Tyr Asp Ala Ser Asn Leu Glu Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Phe Asn Ser Tyr Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```